(12) United States Patent
Alila et al.

(10) Patent No.: US 9,586,996 B2
(45) Date of Patent: Mar. 7, 2017

(54) LYTIC-PEPTIDE-HER2/NEU (HUMAN EPIDERMAL GROWTH FACTOR RECEPTOR 2) LIGAND CONJUGATES AND METHODS OF USE

(75) Inventors: Hector Alila, Baton Rouge, LA (US); Carola Leuschner, Baton Rouge, LA (US)

(73) Assignee: ESPERANCE PHARMACEUTICALS, INC., Houston, TX (US)

( * ) Notice: Subject to any disclaimer, the term of this patent is extended or adjusted under 35 U.S.C. 154(b) by 170 days.

(21) Appl. No.: 13/695,390

(22) PCT Filed: Apr. 28, 2011

(86) PCT No.: PCT/US2011/034338
§ 371 (c)(1),
(2), (4) Date: Feb. 27, 2013

(87) PCT Pub. No.: WO2011/137245
PCT Pub. Date: Nov. 3, 2011

(65) Prior Publication Data
US 2013/0157961 A1 Jun. 20, 2013

Related U.S. Application Data

(60) Provisional application No. 61/330,005, filed on Apr. 30, 2010, provisional application No. 61/362,603, filed on Jul. 8, 2010.

(51) Int. Cl.
| | |
|---|---|
| C07K 16/00 | (2006.01) |
| C07K 7/08 | (2006.01) |
| A61K 39/00 | (2006.01) |
| A61K 38/03 | (2006.01) |
| C07K 14/00 | (2006.01) |
| A61K 47/48 | (2006.01) |
| A61K 38/10 | (2006.01) |
| A61K 38/16 | (2006.01) |
| A61K 45/00 | (2006.01) |

(52) U.S. Cl.
CPC .............. *C07K 14/00* (2013.01); *A61K 38/10* (2013.01); *A61K 38/16* (2013.01); *A61K 45/00* (2013.01); *A61K 47/48438* (2013.01); *A61K 47/48569* (2013.01); *C07K 7/08* (2013.01)

(58) Field of Classification Search
None
See application file for complete search history.

(56) References Cited

U.S. PATENT DOCUMENTS

| | | | | |
|---|---|---|---|---|
| 5,821,337 | A * | 10/1998 | Carter et al. | 530/387.3 |
| 6,987,088 | B2 * | 1/2006 | Dennis | C07K 7/08 |
| | | | | 435/252.3 |
| 8,318,899 | B2 * | 11/2012 | Leuschner et al. | 530/350 |
| 8,436,137 | B2 * | 5/2013 | Kawakami et al. | 530/324 |
| 2004/0018967 | A1 * | 1/2004 | Enright et al. | 514/8 |
| 2009/0269341 | A1 * | 10/2009 | Leuschner et al. | 424/134.1 |
| 2010/0239575 | A1 * | 9/2010 | Banchereau | C07K 14/005 |
| | | | | 424/133.1 |
| 2011/0124564 | A1 * | 5/2011 | Alila | C07K 14/43563 |
| | | | | 514/13.3 |
| 2012/0156134 | A1 * | 6/2012 | Squires | 424/9.1 |

FOREIGN PATENT DOCUMENTS

| | | |
|---|---|---|
| JP | H08507749 A | 8/1996 |
| JP | 2000-514836 A | 11/2000 |
| JP | 2010-154842 A | 7/2010 |
| WO | 2007/115033 A2 | 10/2007 |
| WO | 2009/036082 A2 | 3/2009 |
| WO | 2009/042618 A1 | 4/2009 |
| WO | 2009094634 A1 | 7/2009 |
| WO | 2009/114641 A1 | 9/2009 |
| WO | 2010064207 A2 | 6/2010 |

OTHER PUBLICATIONS

Lu et al (Journal of Biological Chemistry, 2001, 276:34913-34917).*
Marks et al (Cancer Research, 2005, 65:2373-2377).*
Nahta, et al., The HER-2 Targeting Antibodies Trastuzumab and Pertuzumab Synergistically Inhibit the Survival of Breast Cancer Cells, Cancer Res., 2004, 64(7):2343-6.
Viani, et al., Adjuvant Trastuzumab in the Treatment of HER-2-Postitive Early Breast Cancer: a Meta-Analysis of Published Randomized Trials, BMC Cancer, 2007, 7(153):1-11.
Wikipedia_Receptor-Antagonist, Receptor Antagonist, Last Modified on Sep. 27, 2011, [online]. [Retrieved on Oct. 18, 2011] Retrieved from the Internet: <URL: http//en.wikipedia.org/wiki/Receptor_antagonist>.
Wikipedia_Trastuzumab, Trastuzumab, Last modified on Oct. 13, 2011, [online]. [Retrieved on Oct. 18, 2011]. Retrieved from the Internet: <URL: http://en.wikipedia.org/wiki/Trastuzumab>.
Young, L. W., International Search Authority/US, PCT International Search Report, International Application No. PCT/US11/34338, mailed Apr. 9, 2012.
Hansel, W., et al., Destruction of Breast Cancers and Their Metastases by Lytic Peptide Conjugates in vitro and in vivo, Molecular and Cellular Endocrinology, 2007, 260-262:183-189.
Japanese Patent Application No. 2013-508251, Non-final Office Action dated Jun. 16, 2015.
Olafsen, T., et al., Characterization of Engineered Anti-p185HER-2 (scFv-CH3)2 Antibody Fragments (Minibodies) for Tumor Targeting, Protein Engineering Design & Selection, 2004, 17(4):315-323.

* cited by examiner

*Primary Examiner* — Julie Wu
(74) *Attorney, Agent, or Firm* — Robert M. Bedgood; Pillsbury Winthrop Shaw Pittman LLP

(57) ABSTRACT

The invention relates to conjugates that bind to Her2/neu, methods of using conjugates that bind to Her2/neu and methods of treating undesirable or aberrant cell proliferation or hyperproliferative disorders, such as tumors, cancers, neoplasia and malignancies that express Her2/neu.

47 Claims, 2 Drawing Sheets

Figures 1A and 1B
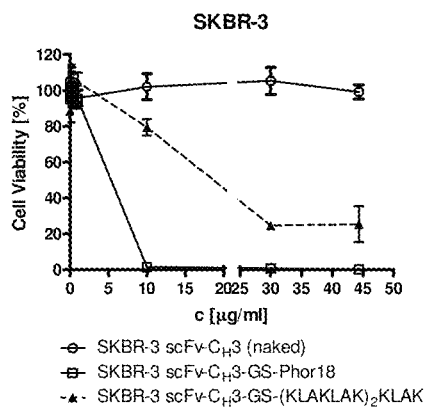
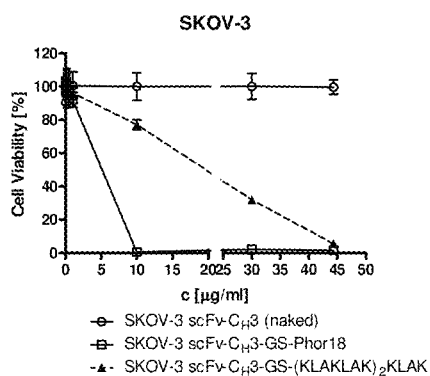
Figures 2A and 2B
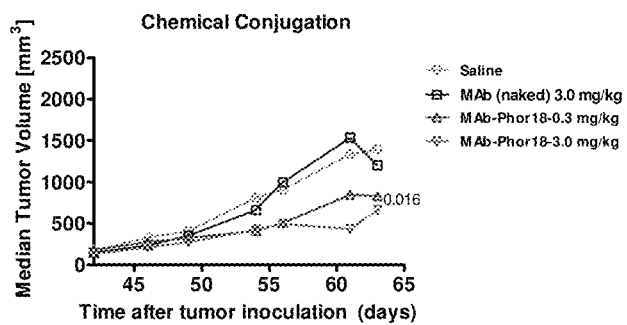
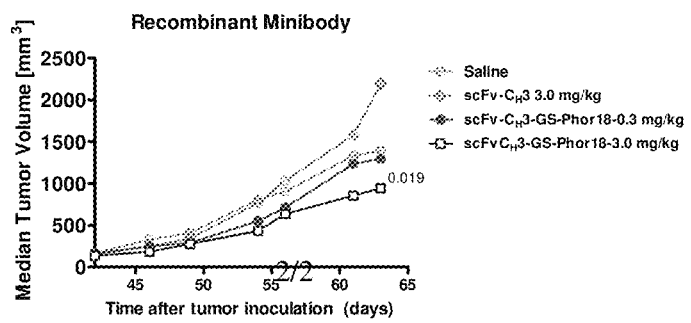

LYTIC-PEPTIDE-HER2/NEU (HUMAN EPIDERMAL GROWTH FACTOR RECEPTOR 2) LIGAND CONJUGATES AND METHODS OF USE

RELATED APPLICATIONS

This application claims priority to application Ser. No. 61/330,005, filed Apr. 30, 2010, and application Ser. No. 61/362,603, filed Jul. 8, 2010, each of which applications are incorporated herein by reference in their entirety.

TECHNICAL FIELD

The invention relates to lytic peptide and Her2/neu (Human Epidermal growth factor Receptor 2, also known as ErbB-2) ligand conjugates, methods of using conjugates, for example, in methods of treating undesirable or aberrant cell proliferation or hyperproliferative disorders, such as non-metastatic and metastatic neoplasias, cancers, tumors and malignancies that express Her2/neu.

INTRODUCTION

The need to develop new therapeutics for treatment of primary tumors and metastases is clearly evident when the five year survival rate of cancer patients is considered: Only 10-40% for patients with lung, colorectal, breast and prostate cancer survive if diagnosed with distant metastatic disease.

SUMMARY

The invention is based, at least in part on lytic domains fused or conjugated to a ligand that binds to Her2/neu (Human Epidermal growth factor Receptor 2, also known as ErbB-2), referred to herein as conjugates or fusion constructs. Contact of a cell with a lytic domain is believed to cause disruption of the cell membrane which results in cell death. The ligand that binds to Her2/neu targets cells that express Her2/neu for destruction by the ligand that binds to Her2/neu and/or lytic domain, including undesirable or aberrant proliferating cells or hyperproliferating cells, such as non-metastatic and metastatic neoplasias, cancers, tumors and malignancies. A number of non-metastatic and metastatic neoplastic, cancer, tumor and malignant cells overexpress receptors or ligands. For example, many non-metastatic and metastatic neoplasias, cancers, tumors and malignancies, express Her2/neu that can be used as a target of the conjugate or fusion construct.

Conjugates can be designed to target any cell or cell population that expresses Her2/neu. Ligands that bind to Her2/neu which include antibodies and fragments thereof, hormones, growth factors, cytokines, etc., can be linked to a lytic domain to provide targeted killing of cells that express or contain Her2/neu thereby reducing or inhibiting cell proliferation or growth.

Conjugates do not require cells to divide in order to kill the target cells. Furthermore, the conjugates are not likely to be immunogenic because they can be made to be relatively small in size. In addition, the conjugates kill multi-drug resistant cells.

In accordance with the invention, there are provided conjugates that include a first and a second domain. In one embodiment, a conjugate includes or consists of a ligand that binds to Her2/neu consisting and a second domain consisting of a 10-120 amino acid fragment, such as a L- or D-amino acid sequence that includes a peptide sequence selected from for example, KFAKFAKKFAKFAKK (SEQ. ID NO. 1), KFAKFAKKFAKFAKKF (SEQ. ID NO. 2), KFAKFAKKFAKFAKKFA (SEQ. ID NO. 3), KFAKFAK-KFAKFAKKFAK (SEQ. ID NO. 4), KFAKFAKKFAK-FAKKFAKF (SEQ. ID NO. 5), KFAKFAKKFAKFAK-KFAKFA (SEQ. ID NO.6) and KFAKFAKKFAKFAKKFAKFAKKFAKFAK (SEQ. ID NO. 7), or a sequence that includes a peptide selected from KFAKFAKKFAKFAKK (SEQ. ID NO. 8), KFAKFAK-KFAKFAKKF (SEQ. ID NO. 9), KFAKFAKKFAKFAK-KFA (SEQ. ID NO. 10), KFAKFAKKFAKFAKKFAK (SEQ. ID NO. 11), KFAKFAKKFAKFAKKFAKF (SEQ. ID NO. 12) and KFAKFAKKFAKFAKKFAKFA (SEQ. ID NO. 13) having one or more of the K residues substituted with any of an F or L residue, one or more of the F residues substituted with any of a K, A or L residue, or one or more of the A residues substituted with any of a K, F or L residue. In another embodiment, a conjugate includes or consists of a ligand that binds to Her2/neu and a second domain consisting of an L- or D-amino acid sequence selected from KFAKFAKKFAKFAKK (SEQ. ID NO. 1), KFAKFAK-KFAKFAKKF (SEQ. ID NO. 2), KFAKFAKKFAKFAK-KFA (SEQ. ID NO. 3), KFAKFAKKFAKFAKKFAK (SEQ. ID NO. 4), KFAKFAKKFAKFAKKFAKF (SEQ. ID NO. 5), KFAKFAKKFAKFAKKFAKFA (SEQ. ID NO.6) and KFAKFAKKFAKFAKKFAKFAKKFAKFAK (SEQ. ID NO. 7), or a sequence that includes a peptide selected from KFAKFAKKFAKFAKK (SEQ. ID NO. 8), KFAKFAK-KFAKFAKKF (SEQ. ID NO. 9), KFAKFAKKFAKFAK-KFA (SEQ. ID NO. 10), KFAKFAKKFAKFAKKFAK (SEQ. ID NO. 11), KFAKFAKKFAKFAKKFAKF (SEQ. ID NO. 12) and KFAKFAKKFAKFAKKFAKFA (SEQ. ID NO. 13) having one or more of the K residues substituted with any of an F or L residue, one or more of the F residues substituted with any of a K, A or L residue, or one or more of the A residues substituted with any of a K, F or L residue. In a further embodiment, a conjugate includes a ligand that binds to Her2/neu and a second domain consisting of an L- or D-amino acid sequence selected from, KFAKFAKKFAK-FAKK_(SEQ. ID NO. 1), KFAKFAKKFAKFAKKF (SEQ. ID NO. 2), KFAKFAKKFAKFAKKFA (SEQ. ID NO. 3), KFAKFAKKFAKFAKKFAK (SEQ. ID NO. 4), KFAK-FAKKFAKFAKKFAKF (SEQ. ID NO. 5), KFAKFAK-KFAKFAKKFAKFA (SEQ. ID NO.6) and KFAKFAK-KFAKFAKKFAKFAKKFAKFAK (SEQ. ID NO. 7), or a sequence that includes a peptide selected from KFAKFAK-KFAKFAKK (SEQ. ID NO. 8), KFAKFAKKFAKFAKKF (SEQ. ID NO. 9), KFAKFAKKFAKFAKKFA (SEQ. ID NO. 10), KFAKFAKKFAKFAKKFAK (SEQ. ID NO. 11), KFAKFAKKFAKFAKKFAKF (SEQ. ID NO. 12) and KFAKFAKKFAKFAKKFAKFA (SEQ. ID NO. 13) having one or more of the K residues substituted with any of an F or L residue, one or more of the F residues substituted with any of a K, A or L residue, or one or more of the A residues substituted with any of a K, F or L residue.

In accordance with the invention, there are also provided isolated and purified peptides that include or consist of a ligand that binds to Her2/neu and a second domain. In various embodiments, a second domain is KFAKFAK-KFAKFAKK (SEQ. ID NO. 1), KFAKFAKKFAKFAKKF (SEQ. ID NO. 2), KFAKFAKKFAKFAKKFA (SEQ. ID NO. 3), KFAKFAKKFAKFAKKFAK (SEQ. ID NO. 4), KFAK-FAKKFAKFAKKFAKF (SEQ. ID NO. 5) or KFAKFAK-KFAKFAKKFAKFA (SEQ. ID NO.6). In additional embodiments, a second domain is KFAKFAKKFAKFAKK (SEQ. ID NO. 1), KFAKFAKKFAKFAKKF (SEQ. ID NO.

2), KFAKFAKKFAKFAKKFA (SEQ. ID NO. 3), KFAK-FAKKFAKFAKKFAK (SEQ. ID NO. 4), KFAKFAK-KFAKFAKKFAKF (SEQ. ID NO. 5) or KFAKFAKKFAK-FAKKFAKFA (SEQ. ID NO. 6) having one or more of the K residues substituted with any of an F or L residue, one or more of the F residues substituted with any of a K, A or L residue, or one or more of the A residues substituted with any of a K, F or L residue.

Conjugates include a ligand that binds to Her2/neu. Ligands include or consist of a molecule that binds to a Her2/neu (Human Epidermal growth factor Receptor 2, also known as ErbB-2), which can be an agonist or antagonist. A ligand or lytic peptide can include or consist of a linear or cyclic structure. A ligand includes an antibody and antibody fragments.

Specific non-limiting examples of ligands include one or more amino acids (e.g., peptides, polypeptides, proteins), nucleic acids and carbohydrates. Specific non-limiting classes of ligands include hormones, growth factors, hormone and growth factor analogues, and fragments of hormones, hormone analogs, growth factors, growth factor analogues, and fragments of growth factors and analogues, antibodies and fragments of antibodies that bind to a Her2/neu. Specific non-limiting examples of antibody fragments include Fab, Fab', F(ab')$_2$, Fv, Fd, single-chain Fv (scFv), disulfide-linked Fvs (sdFv), $V_L$, $V_H$, Camel Ig, V-NAR, VHH, trispecific (Fab$_3$), bispecific (Fab$_2$), diabody ($V_L$-$V_H$)$_2$ or ($V_H$-$V_L$)$_2$), triabody (trivalent), tetrabody (tetravalent), minibody ((scF$_v$-C$_H$3)$_2$), bispecific single-chain Fv (Bis-scFv), IgGdeltaCH2, scFv-Fc, (scFv)$_2$-Fc, affibody (e.g., ZHer2-neu:2, ZHer2-neu:4 ZHer2-neu:7 ZHer2-neu:8), affibody, aptamer, avimer or nanobody.

Her2/neu and/or ligands can be optionally expressed on a cell. Cells that express Her2/neu or that can be targeted in accordance with methods of the invention include hyperproliferative cells. Cells that express Her2/neu or that can be targeted in accordance with methods of the invention for example include breast, ovarian, uterine, cervical, stomach, lung, gastric, colon, bladder, glial, hematologic and endometrial cells.

A ligand that binds to Her2/neu and second domain can include or consist of an amino acid, or an amino acid sequence. In particular aspects, a first or second domain has about 1 to 10, 10 to 20, 15 to 20 (i.e., 15, 16, 17, 18, 19 or 20 amino acids), 20 to 30, 30 to 40, 40 to 50, 60 to 70, 70 to 80, 80 to 90, 90 to 100 or more amino acid residues.

Her2/neu binding ligands and second domains can be positioned at either (or both) the NH$_2$-terminus or the C-terminus relative to each other. Thus, in one embodiment the first (binding ligand) domain is positioned at the NH-terminus relative to the second (lytic peptide) domain, and in another embodiment, the second (lytic peptide) domain is positioned at the C-terminus relative to the first (binding ligand) domain, and in a further embodiment, a first (binding ligand) domain is positioned at the C-terminus relative to the second (lytic peptide) domain, and in still another embodiment, a second (lytic peptide) domain is positioned at the NH-terminus relative to the first (binding ligand) domain. Such second (lytic peptide) domains can be positioned at the C-terminus, the NH-terminus, or both the C-terminus and the NH-terminus. Accordingly, multiple such second (lytic peptide) domains can be included in a conjugate of the invention.

Her2/neu binding ligands and second domains can include or consist of one or more D-amino acids. In particular aspects, a first domain has a D-amino acid, for example, at any K, F or A residue.

Her2/neu binding ligands and second domains can be joined by a covalent (e.g., peptide or nonpeptide) bond. For example, a first and a second domain can be joined by a peptide or a non-peptide linker. In particular aspects, Her2/neu binding ligands and second domains are joined by a peptide sequence having from about 1 to 25 amino acid residues, or having a linear carbon chain. In more particular aspects, Her2/neu binding ligands and second domains are joined by a peptide sequence that includes or consist of one or more A, S or G amino acid residues. In further particular aspects, Her2/neu binding ligands and second domains are joined by a peptide sequence a first and second domain is joined by peptide sequence including or consisting of GSGGS (SEQ. ID NO. 14), ASAAS (SEQ. ID NO. 15), or a linear carbon chain such as CCCCCC (SEQ. ID NO. 16). Other peptide linkers include but are not limited to GS, AF, FK, VK, FFK, FA, GSGRSA (SEQ. ID NO. 17), RVRRSV (SEQ. ID NO. 18), SS, Cit-V, F-Cit, at various length. Thioether, N-succinidyl-3-(2-pyridylothio)propionate, thio ether bonds such as SIAB [N-succinimidyl (4-iodoacetyl) aminobenzoate], SMCC [succinimidyl-4-(N-maleimidomethyl)cyclohexane-1-carboxylate], MBS (m-Maleimidobenzoyl-N-hydroxysuccinimide) and SMPB [succinimidyl-4-(p-maleimidophenyl)butyrate], maleimide and hydrazone linkers.

Her2/neu binding ligands and second domains can further include or consist of additional domains. Thus, in various aspects, a conjugate includes a third, fourth, fifth, sixth, seventh domain, etc.

Conjugates include or consist of isolated and purified forms. Conjugates also include or consist of a mixture. Such mixtures include compositions, such as a mixture of conjugate and a pharmaceutically acceptable carrier or excipient appropriate for administration to or in vivo contact with a subject, or a mixture of conjugate and an anti-cell proliferative or immune stimulating agent.

Conjugates include or consist of a unit dosage form. In one embodiment, a conjugate is a unit dosage in an amount effective to treat a subject having undesirable cell proliferation or a hyperproliferative disorder. In another embodiment, a conjugate is a unit dosage in an amount effective to treat a subject having a neoplasia, tumor or cancer. In an additional embodiment, a conjugate is a unit dosage in an amount effective to reduce fertility of a subject.

Conjugates can be included within kits, optionally with instructions for practicing a method. In one embodiment, a kit includes a conjugate and instructions for reducing or inhibiting proliferation of a cell, reducing or inhibiting proliferation of a hyperproliferating cell, reducing or inhibiting proliferation of a neoplastic, tumor or cancer cell, treating a subject having a hyperproliferative disorder, treating a subject having a neoplasia, tumor or cancer, or reducing fertility of an animal.

In accordance with the invention, there are also provided nucleic acids that encode conjugates. In one embodiment, a nucleic acid encodes a conjugate including or consisting of a ligand that binds to Her2/neu and a second domain and a peptide sequence selected from for example, KFAKFAK-KFAKFAKK (SEQ. ID NO. 1), KFAKFAKKFAKFAKKF (SEQ. ID NO. 2), KFAKFAKKFAKFAKKFA (SEQ. ID NO. 3), KFAKFAKKFAKFAKKFAK (SEQ. ID NO. 4), KFAK-FAKKFAKFAKKFAKF (SEQ. ID NO. 5), KFAKFAK-KFAKFAKKFAKFA (SEQ. ID NO. 6) and KFAKFAK-KFAKFAKKFAKFAKKFAKFAK (SEQ. ID NO. 7), or a sequence that includes a peptide selected from KFAKFAK-KFAKFAKK (SEQ. ID NO. 8), KFAKFAKKFAKFAKKF (SEQ. ID NO. 9), KFAKFAKKFAKFAKKFA (SEQ. ID NO.

10), KFAKFAKKFAKFAKKFAK (SEQ. ID NO. 11), KFAKFAKKFAKFAKKFAKF (SEQ. ID NO. 12) and KFAKFAKKFAKFAKKFAKFA (SEQ. ID NO. 13) having one or more of the K residues substituted with any of an F or L residue, one or more of the F residues substituted with any of a K, A or L residue, or one or more of the A residues substituted with any of a K, F or L residue. In another embodiment, a nucleic acid encodes a conjugate including or consisting of a ligand that binds to Her2/neu and a second domain and a peptide consisting of an L- or D-amino acid sequence selected from KFAKFAKKFAKFAKK (SEQ. ID NO. 1), KFAKFAKKFAKFAKKF (SEQ. ID NO. 2), KFAKFAKKFAKFAKKFA (SEQ. ID NO. 3), KFAKFAKKFAKFAKKFAK (SEQ. ID NO. 4), KFAKFAKKFAKFAKKFAKF (SEQ. ID NO. 5), KFAKFAKKFAKFAKKFAKFA (SEQ. ID NO. 6) and KFAKFAKKFAKFAKKFAKFAKKFAKFAK (SEQ. ID NO. 7).

Nucleic acids can be included in a vector, such as an expression vector that when expressed in a cell encodes a conjugate. Host cells can be transformed with a nucleic acid in a vector, such that the cell expresses a conjugate encoded by the nucleic acid.

Conjugates are useful for, among other things, reducing or inhibiting proliferation of a cell, reducing or inhibiting cell proliferation, reducing or inhibiting proliferation of a hyperproliferating cell, reducing or inhibiting proliferation of a neoplastic, tumor, cancer or malignant cell and treating undesirable or aberrant cell proliferation, such as hyperproliferating cells or hyperproliferative disorders. Non-limiting examples of hyperproliferative disorders include benign hyperplasia, non-metastatic and metastatic neoplasias, cancers tumors and malignancies.

In accordance with the invention, there are further provided methods of reducing or inhibiting proliferation of a cell; methods of reducing or inhibiting cell proliferation; methods of reducing or inhibiting proliferation of a hyperproliferating cell; and methods of reducing or inhibiting proliferation of a neoplastic, tumor, cancer or malignant cell. In various embodiments, a method includes contacting a cell with a conjugate in an amount sufficient to reduce or inhibit proliferation of the cell; contacting a cell with a conjugate in an amount sufficient to reduce or inhibit cell proliferation; contacting a cell with a conjugate in an amount sufficient to reduce or inhibit proliferation of the hyperproliferating cell; and contacting a cell with a conjugate in an amount sufficient to reduce or inhibit proliferation of the neoplastic, tumor, cancer or malignant cell.

In accordance with the invention, there are moreover provided methods of selectively reducing or inhibiting proliferation of a cell that expresses Her2/neu; selectively reducing or inhibiting proliferation of a hyperproliferating cell that expresses Her2/neu; and selectively reducing or inhibiting proliferation of a neoplastic, tumor, cancer or malignant cell that expresses Her2/neu. In various embodiments, a method includes contacting a cell with a conjugate in an amount sufficient to reduce or inhibit proliferation of the cell; contacting a cell with the conjugate in an amount sufficient to reduce or inhibit proliferation of the hyperproliferating cell; and contacting a cell with a conjugate in an amount sufficient to reduce or inhibit proliferation of the neoplastic, tumor, cancer or malignant cell, wherein the ligand of the conjugate binds to the Her2/neu expressed by the cell.

Cells targeted in accordance with the invention methods include cells that express Her2/neu. Cells targeted in accordance with the invention methods therefore include, for example, breast, ovarian, uterine, cervical, stomach, lung, gastric, colon, bladder, glial, hematologic and endometrial cells.

Methods performed include, among others, contacting a subject in need of inhibiting, reducing or preventing proliferation, survival, differentiation, death, or activity of a cells, such as a hyperproliferative cell or an undesirably proliferating cell. Exemplary subjects include a subject having or at risk of having undesirable or aberrant cell proliferation; a subject having or at risk of having a benign hyperplasia; or a non-metastatic or metastatic neoplasia, cancer, tumor or malignancy (e.g., a solid or liquid tumor, in any of breast, ovarian, uterine, cervical, stomach, lung, gastric, colon, bladder, glial, hematologic or endometrial cells).

In accordance with the invention, there are additionally provided methods of treating a subject having a hyperproliferative disorder and methods of treating a subject having a neoplasia, tumor, cancer or malignancy (metastatic, non-metastatic or benign). In various embodiments, a method includes, administering to a subject an amount of the conjugate sufficient to treat the hyperproliferative disorder; and administering to a subject an amount of the conjugate sufficient to reduce or inhibit proliferation of the neoplasia, tumor, cancer or malignancy.

Methods include treating a subject having or at risk of having a metastasis. For example, an amount of a conjugate effective to reduce or inhibit spread or dissemination of a tumor, cancer or neoplasia to other sites, locations or regions within the subject. In various embodiments, a method reduces or inhibits metastasis of a primary tumor or cancer to one or more other sites, formation or establishment of a metastasis at one or more other sites, locations or regions thereby reducing or inhibiting tumor or cancer relapse or tumor or cancer progression. In further embodiments, a method reduces or inhibits growth, proliferation, mobility or invasiveness of tumor or cancer cells that potentially or do develop metastases (e.g., disseminated tumor cells); reduces or inhibits formation or establishment of metastases arising from a primary tumor or cancer to one or more other sites, locations or regions distinct from the primary tumor or cancer; reduces or inhibits growth or proliferation of a metastasis at one or more other sites, locations or regions distinct from the primary tumor or cancer after the metastasis has formed or has been established; or reduces or inhibits formation or establishment of additional metastasis after the metastasis has been formed or established. In yet another embodiment, a method reduces or inhibits relapse or progression of the neoplasia, tumor, cancer or malignancy.

In accordance with the invention, there are still further provided methods of reducing or inhibiting metastasis of a neoplasia, tumor, cancer or malignancy to other sites, or formation or establishment of metastatic neoplasia, tumor, cancer or malignancy at other sites distal from a primary neoplasia, tumor, cancer or malignancy. In various embodiments, a method includes administering to a subject an amount of the conjugate sufficient to reduce or inhibit metastasis of the neoplasia, tumor, cancer or malignancy to other sites, or formation or establishment of metastatic neoplasia, tumor, cancer or malignancy at other sites distal from the primary neoplasia, tumor, cancer or malignancy.

Neoplasia, tumor, cancer and malignancy treatable in accordance with the invention include solid cellular mass, hematopoietic cells, or a carcinoma, sarcoma (e.g. lymphosarcoma, liposarcoma, osteosarcoma, chondrosarcoma, leiomyosarcoma, rhabdomyosarcoma or fibrosarcoma), lymphoma, leukemia, adenoma, adenocarcinoma, melanoma, glioma, glioblastoma, meningioma, neuroblastoma, retinoblastoma, astrocytoma, oligodendrocytoma, mesothelioma, reticuloendothelial, lymphatic or haematopoietic (e.g., myeloma, lymphoma or leukemia) neoplasia, tumor, cancer or malignancy.

Neoplasia, tumor, cancer and malignancy treatable in accordance with the invention can be present in or affect a lung (small cell lung or non-small cell lung cancer), breast, ovarian, uterine, cervical, stomach, lung, gastric, colon, bladder, glial, hematologic, endometrial, lymph, blood, muscle, or skin cell neoplasia, tumor, cancer, or malignancy.

Methods may be practiced with other treatments or therapies (e.g., surgical resection, radiotherapy, ionizing or chemical radiation therapy, chemotherapy, immunotherapy, local or regional thermal (hyperthermia) therapy, or vaccination). Such treatments or therapies can be administered prior to, substantially contemporaneously with (separately or in a mixture), or following administration of a conjugate. In one embodiment, a method includes administering an anti-cell proliferative, anti-neoplastic, anti-tumor, anti-cancer or immune-enhancing treatment or therapy. In further embodiments, a method includes administering an alkylating agent, anti-metabolite, plant extract, plant alkaloid, nitrosourea, hormone, nucleoside or nucleotide analog; cyclophosphamide, azathioprine, cyclosporin A, prednisolone, melphalan, chlorambucil, mechlorethamine, busulphan, methotrexate, 6-mercaptopurine, thioguanine, 5-fluorouracil, cytosine arabinoside, 5-azacytidine (5-AZC) and 5-azacytidine related compounds, bleomycin, actinomycin D, mithramycin, mitomycin C, carmustine, lomustine, semustine, streptozotocin, hydroxyurea, cisplatin, carboplatin, oxiplatin, mitotane, procarbazine, dacarbazine, taxol, vinblastine, vincristine, doxorubicin or dibromomannitol, topoisomerase inhibitors, (irinotecan, topotecan, etoposide, teniposide), gemcitabine, pemetrexed etc. Cell or immunotherapies include lymphocytes, plasma cells, macrophages, dendritic cells, T-cells, NK cells or B-cells; an antibody, a cell growth factor, a cell survival factor, a cell differentiative factor, a cytokine or a chemokine (examples are interleukins IL-2, IL-1α, IL-1β, IL-3, IL-6, IL-7, granulocyte-macrophage-colony stimulating factor (GMCSF), IFN-γ, IL-12, TNF-α, TNFβ, MIP-1α, MIP-1β, RANTES, SDF-1, MCP-1, MCP-2, MCP-3, MCP-4, eotaxin, eotaxin-2, I-309/TCA3, ATAC, HCC-1, HCC-2, HCC-3, LARC/MIP-3α, PARC, TARC, CKβ, CKβ6, CKβ7, CKβ8, CKβ9, CKβ11, CKβ12, C10, IL-8, GROα, GROβ, ENA-78, GCP-2, PBP/CTAPIIIβ-TG/NAP-2, Mig, PBSF/SDF-1, or lymphotactin) etc.

Additional agents that are applicable with conjugates are targeted drugs or biologicals such as antibodies or small molecules. Non-limiting examples of monoclonal antibodies include rituximab (Rituxan®), trastuzumab (Herceptin), pertuzumab, cetuximab (Erbitux), ipilimumab, zalutumumab, dalotuzumab, figitumumab, ramucirumab, galiximab, farletuzumab, ocrelizumab, ofatumumab, alemtuzumab (Campath), panitumumab (Vectibix), ibritumomab tiuxetan (Zevalin), tositumomab (Bexxar) etc. which can be used in combination with, inter alia, a conjugate in accordance with the invention. Other targeted drugs that are applicable for use with conjugates are imatinib (Gleevec), gefitinib (Iressa), bortezomib (Velcade), lapatinib (Tykerb), sunitinib (Sutent), sorafenib (Nevaxar), nilotinib (Tasigna) etc.

Methods of the invention include providing a subject with a benefit. In particular embodiments, a method of treatment results in partial or complete destruction of the neoplastic, tumor, cancer or malignant cell mass, volume, size or numbers of cells, stimulating, inducing or increasing neoplastic, tumor, cancer or malignant cell necrosis, lysis or apoptosis, reducing neoplasia, tumor, cancer or malignancy volume size, cell mass, inhibiting or preventing progression or an increase in neoplasia, tumor, cancer or malignancy volume, mass, size or cell numbers, or prolonging lifespan; results in reducing or decreasing severity, duration or frequency of an adverse symptom or complication associated with or caused by the neoplasia, tumor, cancer or malignancy; results in reducing or decreasing pain, discomfort, nausea, weakness or lethargy; or results in increased energy, appetite, improved mobility or psychological well being.

Subjects treatable in accordance with the methods include mammals. In particular embodiments, a subject is a human.

DESCRIPTION OF DRAWINGS

FIGS. 1A and 1B show cytotoxicity of recombinantly scFv-CH3 (naked antibody), scFv-$C_H3$-GS-Phor18 and scFv-$C_H3$-GS-(KLAKLAK)$_2$KLAK (SEQ. ID NO. 66) to Her2-neu receptor positive A) breast (SKBR-3); and B) ovarian (SKOV-3) cancer cell lines determined after 48 hours.

FIGS. 2A and 2B show median tumor volumes from mice treated with MAb (naked), A) MAb-Phor18 and B) recombinant scFv-$C_H3$ naked antibody and scFv-$C_H3$-Phor-18 conjugates during the study period of 64 days in SKOV-3 xenografted mice in comparison with saline injected mice.

DETAILED DESCRIPTION

Figure 3:
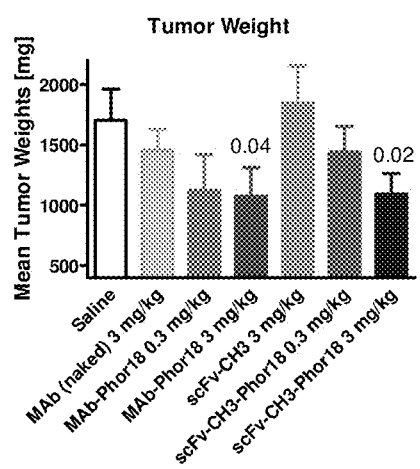
FIG. 3 shows mean tumor weights from mice treated with MAb (naked), MAb-Phor18 and recombinantly scFv-$C_H3$ naked antibody and scFv-$C_H3$-Phor-18 conjugates on day 64 in SKOV-3 xenografted mice in comparison with saline injected mice.

The invention is based at least in part on a conjugate that includes a ligand that binds to Her2/neu joined or fused to a second lytic domain. In a typical configuration, a conjugate first domain includes a ligand that binds to Her2/neu and a second domain that includes lytic portion, which is directly or indirectly toxic to a cell, which can thereby reduce cell proliferation or survival, or stimulate, induce, increase or enhance cell death, killing or apoptosis.

In accordance with the invention, there are provided conjugates that include or consist of a first ligand that binds to Her2/neu domain and include or consist of a second lytic or toxic domain. In one embodiment, a conjugate includes a ligand that binds to Her2/neu and a second domain consisting of a 12-100 residue L- or D-amino acid sequence that includes a peptide sequence (selected from amino acids such as Lysine=K, Phenylalanine=F and Alanine=A), for example, KFAKFAKKFAKFAKK (SEQ. ID NO. 1), KFAKFAKKFAKFAKKF (SEQ. ID NO. 2), KFAKFAKKFAKFAKKFA (SEQ. ID NO. 3), KFAKFAKKFAKFAKKFAK (SEQ. ID NO. 4), KFAKFAKKFAKFAKKFAKF (SEQ. ID NO. 5), KFAKFAKKFAKFAKKFAKFA (SEQ. ID NO.6) and KFAKFAKKFAKFAKKFAKFAKKFAKFAK (SEQ. ID NO. 7). In another embodiment, a conjugate includes a first ligand that binds to Her2/neu domain and a second domain consisting of an L- or D-amino acid sequence selected from KFAKFAKKFAKFAKK (SEQ. ID NO. 1), KFAKFAKKFAKFAKKF (SEQ. ID NO. 2), KFAKFAKKFAKFAK- KFA (SEQ. ID NO. 3), KFAKFAKKFAKFAKKFAK (SEQ. ID NO. 4), KFAKFAKKFAKFAKKFAKF (SEQ. ID NO. 5), KFAKFAKKFAKFAKKFAKFA (SEQ. ID NO.6) and KFAKFAKKFAKFAKKFAKFAKKFAKFAK (SEQ. ID NO. 7).

As used herein, the term "conjugate" or "fusion construct" and grammatical variations thereof, means that the construct contains portions or sections that are derived from, obtained or isolated from, or are based upon or modeled after two different molecular entities that are distinct from each other and do not typically exist together in nature. That is, for example, one portion of the conjugate includes or consists of a ligand that binds to Her2/neu and a second portion of the conjugate includes or consists of a lytic portion, each of first and second domains structurally distinct. A conjugate can also be referred to as a "fusion construct," wherein the conjugate includes or consists of a second domain ligand that binds to Her2/neu and a second domain lytic portion.

First domains and or second domains of conjugates include or consist of amino acid sequences (peptides, polypeptides, proteins, lectins), nucleic acids (DNA, RNA) and carbohydrates (saccharides, sialic acid, galactose, mannose, fucose, acetylneuraminic acid, etc.). The terms "amino acid sequence," "protein," "polypeptide" and "peptide" are used interchangeably herein to refer to two or more amino acids, or "residues," covalently linked by an amide bond or equivalent. Amino acid sequences can be linked by non-natural and non-amide chemical bonds including, for example, those formed with glutaraldehyde, N-hydroxysuccinimide esters, bifunctional maleimides, or N,N'-dicyclohexylcarbodiimide (DCC). Non-amide bonds include, for example, ketomethylene, aminomethylene, olefin, ether, thioether and the like (see, e.g., Spatola in *Chemistry and Biochemistry of Amino Acids, Peptides and Proteins*, Vol. 7, pp 267-357 (1983), "Peptide and Backbone Modifications," Marcel Decker, NY).

First and second domains of a conjugate or fusion construct include L-amino acid sequences, D-amino acid sequences and amino acid sequences with mixtures of L-amino acids and D-amino acids. Amino acid sequences of first and second domains can be a linear or a cyclic structure, conjugated to a distinct moiety (e.g., third, fourth, fifth, sixth, seventh, etc. domains), form intra or intermolecular disulfide bonds, and also form higher order multimers or oligomers with the same or different amino acid sequence, or other molecules.

Exemplary lengths of conjugates are from about 5 to 15, 20 to 25, 25 to 50, 50 to 100, 100 to 150, 150 to 200, or 200 to 300 or more amino acid residues in length. In particular embodiments, a first or second domain includes or consists of an amino acid sequence of about 1 to 10, 10 to 20, 15 to 20, 20 to 30, 30 to 40, 40 to 50, 60 to 70, 70 to 80, 80 to 90, 90 to 100 or more residues. In more particular embodiments, a first domain consists of a 15, 16, 17, 18, 19, 20, 28 or more residue amino acid sequence.

Conjugate with first and a second domain, optionally the ligand that binds to Her2/neu lytic domain or second lytic domain form an amphipathic alpha-helix. An amphipathic alpha-helix contains mostly hydrophilic amino acids on one side of the alpha-helix and the other side contains mostly hydrophobic amino acids. Since the alpha helix makes a complete turn for every 3.6 residues, the amino acid sequence of an amphipathic alpha helix alternates between hydrophilic and hydrophobic residues every 3 to 4 residues. A PNNPNNP (SEQ. ID NO. 19) repeat pattern or motif is predicted to form an amphipathic alpha-helix where P represents a positively charged amino acid residue and N a neutral amino acid residue. A PNNPNNP (SEQ. ID NO. 19) repeat pattern provides a cationic binding site for the lytic peptide to a negatively charged cell membrane and a hydrophobic site for membrane interaction/penetration. Conjugates therefore include second domains with one or more uninterrupted PNNPNNP (SEQ. ID NO. 19) repeat patterns or motifs, or one or more interrupted PNNPNNP (SEQ. ID NO. 19) repeat patterns or motifs, which can form an amphipathic alpha-helix. For example, a 15 or 18 residue amino acid sequence, such as KFAKFAKKFAKFAKK (SEQ. ID NO. 4) and KFAKFAKKFAKFAKKFAK (SEQ. ID NO. 1), has uninterrupted and interrupted PNNPNNP (SEQ. ID NO. 19)_repeat motifs.

A conjugate first domain, such as a ligand that binds to Her2/neu, includes or consists of a ligand, antibody, hormone, growth factor, or an analogue or fragment thereof.

Her2/neu is typically expressed by or present on (e.g., a membrane receptor) or within a cell. Her2/neu may associate with the cell membrane surface or traverse the cell membrane. For example, Her2/neu can have a transmembrane domain that traverses the cell membrane, optionally with a portion that is cytoplasmic or extracellular, or both. Her2/neu therefore include full length intact native Her2/neu containing an extracellular, transmembrane or cytoplasmic portion, as well as truncated forms or fragments thereof (e.g., an extracellular, transmembrane or cytoplasmic portion or subsequence of Her2/neu alone, or in combination). For example, a soluble Her2/neu typically lacks a transmembrane and may optionally also lack all or a part of the native extracellular or cytoplasmic region (if present in native Her2/neu). Such truncated forms and fragments can retain at least partial binding to a ligand.

Ligands that bind to Her2/neu of conjugates include or consist of any entity that binds to Her2/neu, specifically or non-specifically. Non-limiting examples of ligands therefore include antibodies, antibody fragments, hormones, hormone analogues, fragments of a hormone or hormone analogue that binds to Her2/neu, growth factors, growth factor analogues, fragments of a growth factor or growth factor analogue that binds to Her2/neu, etc.

Exemplary ligands that bind to Her2/neu include affibodies, such as ZHer2-neu:2, ZHer2-neu:4 ZHer2-neu:7 ZHer2-neu:8 and Fab63. Exemplary affibody sequences are as follows:

|  |  | (SEQ ID NO: 20) |
|---|---|---|
| $Z_{wt}$ | VDNKFNK EQQNAFYEILH LPNLNE EQRNAFIQS-LKD DPSQ SANLLAEAKKLNDA QAPK | |

|  |  | (SEQ ID NO: 21) |
|---|---|---|
| $Z_{her2:4}$ | VDNKFNK ELRQAYWEIQA LPNLNW TQSRA-FIRSLYD DPSQ SANLLAEAKKLNDA QAPK | |

|  |  | (SEQ ID NO: 22) |
|---|---|---|
| $Z_{her2:7}$ | VDNKFNK EPKTAYWEIVK LPNLNP EQRRA-FIRSLYD DPSQ SANLLAEAKKLNDA QAPK | |

|  |  | (SEQ ID NO: 23) |
|---|---|---|
| $Z_{her2:24}$ | VDNKFNK EPREAYWEIQR LPNLNN KQKAAF-IRSLYD DPSQ SANLLAEAKKLNDA QAPK | |

|  |  | (SEQ ID NO: 24) |
|---|---|---|
| $Z_{her2:79}$ | VDNKFNK EWMTAGKEIYR LPN-LNG TQVRAFIQSLSD DPSQ SANLLAEAKKLNDA QAPK | |

```
Z_her2:2   VDNKFNK EWVQAGSEIYN LPNLNR AQMRA-         (SEQ ID NO: 25)
           FIRSLSD DPSQ
           SANLLAEAKKLNDA QAPK Z_her2:8   VDNKFNK EIKQAFHEIVR LPNLNA DQVRAFIYS-     (SEQ ID NO: 26)
           LGD DPSQ
           SANLLAEAKKLNDA QAPK Z_her2:25  VDNKFNK EMVDAGAEIWR LPN-                  (SEQ ID NO: 27)
           LNA KQM*AFIDSLGD DPSQ
           SANLLAEAKKLNDA QAPK
```

Exemplary growth factors useful as ligands that bind to Her2/neu include epidermal growth factor and epidermal growth factor analogues.

Her2/neu ligands and binding moieties further include antibodies, and antibody fragments. An "antibody" refers to any monoclonal or polyclonal immunoglobulin molecule, such as IgM, IgG, IgA, IgE, IgD, and any subclass thereof. Exemplary subclasses for IgG are $IgG_1$, $IgG_2$, $IgG_3$ and $IgG_4$ including engineered antibody subclasses and recombinant antibodies with various glycosylation patterns. Antibodies include those produced by or expressed on cells, such as B cells, or synthesized or engineered to be produced by other cells, e.g., CHO cells. Such antibodies include those with improved characteristics, such as increased serum stability and/or half life in vivo, PK, etc. (e.g., as described in Antibody Engineering Vol 1, Konterman R and Duebel S, eds., 2010, Springer, WO 2006/130834 and Horton et al., Cancer Res 68:8049 (2008)).

Non-limiting mutations in the Fc include, for example, I253A, H310A, H435 R, H435Q, G236R, L328 R, S239D, I332E. Non-limiting mutations in IgG1 can beat residues 238, 252, 253, 254, 255, 256, 265, 272, 289, 288, 303, 305, 307, 309, 311, 312, 317, 340, 356, 360, 362, 376, 378, 380, 382, 386, 388, 400, 413, 415, 424, 433, 434, 435, 439 and/or 477 of the Fc region.

An antibody fragment or subsequence refers to a portion of a full length antibody that retains at least partial antigen binding capability of a comparison full length antibody. Exemplary antibody fragments include Fab, Fab', $F(ab')_2$, Fv, Fd, single-chain Fv (scFv), disulfide-linked Fvs (sdFv), $V_L$, $V_H$, Camel Ig, V-NAR, VHH, trispecific ($Fab_3$), bispecific ($Fab_2$), diabody (($V_L$-$V_H$)$_2$ or ($V_H$-$V_L$)$_2$), triabody (trivalent), tetrabody (tetravalent), minibody ((scFv-$C_H3$)$_2$), bispecific single-chain Fv (Bis-scFv), IgGdelta$C_H2$, scFv-Fc, (scFv)$_2$-Fc, affibody, aptamer, avimer, nanobody or other antigen binding fragment.

Exemplary antibodies bind to epitopes present on Her2/neu. Exemplary Her2/neu epitopes (the amino acid position numbers of Her2 epitope is referred to by a "p" followed by arabic numbers) include HER-2 (p5-13) A2, HER-2 (p8-16) A24, HER-2 (p48-56) A2, HER-2 (p63-71) A24, HER-2 (p106-114) A2, HER-2 (p369-377) A2, A3, A26, HER-2 (p435-443) A2, HER-2 (p654-662) A2, HER-2 (p665-673) A2, HER-2 (p689-697) A2, HER-2 (p754-762) A3, All, A33, HER-2 (p773-782) A2, HER-2 (p780-788) A24, HER-2 (p785-794) A2, HER-2 (p789-797) A2, HER-2 (p799-807) A2, HER-2 (p952-961) A2 and HER-2 (p1023-1032) A2.

Exemplary antibodies include humanized anti-ErbB2 antibodies huMAb4D1-1, huMAb4D5-1, huMAb4D5-2, huMAb4D5-3, huMAb4D5-4, huMAb4D5-5, huMAb4D5-6, huMAb4D5-7 and huMAb4D5-8 (HERCEPTIN™) as described in U.S. Pat. No. 5,821,337; humanized 520C9 (WO 93/21319) and humanized 2C4 (pertuzumab) as described in U.S. Pat. No. 7,097,840 and pertuzumab variants as described in US2009/0285837A1.

huMAb4D5-1:

```
V_L (Light chain)(SEQ ID NO: 28):
1               10                  20                  30                  40
D I Q M T Q S P S S L S A S V G D R V T I T C R A S Q D V N T A V A W Y Q Q K P G 50                  60                  70                  80
K A P K L L I Y S A S F L E S G V P S R F S G S G S G T D F T L T I S S L Q P E D F 90                  100
A T Y Y C Q Q H Y T T P P T F G Q G T K V E I K V_H (heavy chain)(SEQ ID NO: 29):
1               10                  20                  30                  40
E V Q L V E S G G G L V Q P G G S L R L S C A A S G F N I K D T Y I H W V R Q A P 50                  60                  70                  80
G K G L E W V A R I Y P T N G Y T R Y A D S V K G R F T I S R D D S K N T L Y L Q 90                  100                 110                 120
M N S L R A E D T A V Y Y C A R W G G D G F Y A M D V W G Q G T L V T V S S
``` huMAb4D5-2:

```
V_L (Light chain)(SEQ ID NO: 30):
1               10                  20                  30                  40
D I Q M T Q S P S S L S A S V G D R V T I T C R A S Q D V N T A V A W Y Q Q K P G 50                  60                  70                  80
K A P K L L I Y S A S F L E S G V P S R F S G S G S G T D F T L T I S S L Q P E D F 90                  100
A T Y Y C Q Q H Y T T P P T F G Q G T K V E I K
```

V_H (heavy chain)(SEQ ID NO: 31):
```
1              10              20              30              40
E V Q L V E S G G G L V Q P G G S L R L S C A A S G F N I K D T Y I H W V R Q A P
              50              60              70              80
G K G L E W V A R I Y P T N G Y T R Y A D S V K G R F T I S A D D S K N T L Y L Q
              90             100             110             120
M N S L R A E D T A V Y Y C A R W G G D G F Y A M D V W G Q G T L V T V S S
``` huMAb4D5-3:

V_L (Light chain)(SEQ ID NO: 32):
```
1              10              20              30              40
D I Q M T Q S P S S L S A S V G D R V T I T C R A S Q D V N T A V A W Y Q Q K P G
              50              60              70              80
K A P K L L I Y S A S F L E S G V P S R F S G S G S T D F T L T I S S L Q P E D F
              90             100
A T Y Y C Q Q H Y T T P P T F G Q G T K V E I K
```

V_H (heavy chain)(SEQ ID NO: 33):
```
1              10              20              30              40
E V Q L V E S G G G L V Q P G G S L R L S C A A S G F N I K D T Y I H W V R Q A P
              50              60              70              80
G K G L E W V A R I Y P T N G Y T R Y A D S V K G R F T I S A D T S K N T A Y L Q
              90             100             110             120
M N S L R A E D T A V Y Y C S R W G G D G F Y A M D V W G Q G T L V T V S S
``` huMAb4D5-4:

V_L (Light chain)(SEQ ID NO: 34):
```
1              10              20              30              40
D I Q M T Q S P S S L S A S V G D R V T I T C R A S Q D V N T A V A W Y Q Q K P G
              50              60              70              80
K A P K L L I Y S A S F L E S G V P S R F S G S R S G T D F T L T I S S L Q P E D F
              90             100
A T Y Y C Q Q H Y T T P P T F G Q G T K V E I K
```

V_H (heavy chain)(SEQ ID NO: 35):
```
1              10              20              30              40
E V Q L V E S G G G L V Q P G G S L R L S C A A S G F N I K D T Y I H W V R Q A P
              50              60              70              80
G K G L E W V A R I Y P T N G Y T R Y A D S V K G R F T I S A D T S K N T L Y L Q
              90             100             110             120
M N S L R A E D T A V Y Y C S R W G G D G F Y A M D V W G Q G T L V T V S S
``` huMAb4D5-5:

V_L (Light chain)(SEQ ID NO: 36):
```
1              10              20              30              40
D I Q M T Q S P S S L S A S V G D R V T I T C R A S Q D V N T A V A W Y Q Q K P G
              50              60              70              80
K A P K L L I Y S A S F L E S G V P S R F S G S R S G T D F T L T I S S L Q P E D F
              90             100
A T Y Y C Q Q H Y T T P P T F G Q G T K V E I K
```

V_H (heavy chain)(SEQ ID NO: 37):
```
1              10              20              30              40
E V Q L V E S G G G L V Q P G G S L R L S C A A S G F N I K D T Y I H W V R Q A P
```

-continued

```
                50                  60                  70                  80
          G K G L E W V A R I Y P T N G Y T R Y A D S V K G R F T I S A D T S K N T A Y L Q
                90                 100                 110                 120
          M N S L R A E D T A V Y Y C S R W G G D G F Y A M D V W G Q G T L V T V S S
``` huMAb4D5-6:

V_L (Light chain) (SEQ ID NO: 38):
```
          1                  10                  20                  30                  40
          D I Q M T Q S P S S L S A S V G D R V T I T C R A S Q D V N T A V A W Y Q Q K P G
                50                  60                  70                  80
          K A P K L L I Y S A S F L Y S G V P S R F S G S R S G T D F T L T I S S L Q P E D F
                90                 100
          A T Y Y C Q Q H Y T T P P T F G Q G T K V E I K
```

V_H (heavy chain) (SEQ ID NO: 39):
```
          1                  10                  20                  30                  40
          E V Q L V E S G G G L V Q P G G S L R L S C A A S G F N I K D T Y I H W V R Q A P
                50                  60                  70                  80
          G K G L E W V A R I Y P T N G Y T R Y A D S V K G R F T I S A D T S K N T A Y L Q
                90                 100                 110                 120
          M N S L R A E D T A V Y Y C S R W G G D G F Y A M D V W G Q G T L V T V S S
``` huMAb4D5-7:

V_L (Light chain) (SEQ ID NO: 40):
```
          1                  10                  20                  30                  40
          D I Q M T Q S P S S L S A S V G D R V T I T C R A S Q D V N T A V A W Y Q Q K P G
                50                  60                  70                  80
          K A P K L L I Y S A S F L E S G V P S R F S G S R S G T D F T L T I S S L Q P E D F
                90                 100
          A T Y Y C Q Q H Y T T P P T F G Q G T K V E I K
```

V_H (heavy chain) (SEQ ID NO: 41):
```
          1                  10                  20                  30                  40
          E V Q L V E S G G G L V Q P G G S L R L S C A A S G F N I K D T Y I H W V R Q A P
                50                  60                  70                  80
          G K G L E W V A R I Y P T N G Y T R Y A D S V K G R F T I S A D T S K N T A Y L Q
                90                 100                 110                 120
          M N S L R A E D T A V Y Y C S R W G G D G F Y A M D Y W G Q G T L V T V S S
``` huMAb4D5-8:

V_L (Light chain) (SEQ ID NO: 42):
```
          1                  10                  20                  30                  40
          D I Q M T Q S P S S L S A S V G D R V T I T C R A S Q D V N T A V A W Y Q Q K P G
                50                  60                  70                  80
          K A P K L L I Y S A S F L Y S G V P S R F S G S R S G T D F T L T I S S L Q P E D F
                90                 100
          A T Y Y C Q Q H Y T T P P T F G Q G T K V E I K
```

V_H (heavy chain) (SEQ ID NO: 43):
```
          1                  10                  20                  30                  40
          E V Q L V E S G G G L V Q P G G S L R L S C A A S G F N I K D T Y I H W V R Q A P
                50                  60                  70                  80
          G K G L E W V A R I Y P T N G Y T R Y A D S V K G R F T I S A D T S K N T A Y L Q
                90                 100                 110                 120
          M N S L R A E D T A V Y Y C S R W G G D G F Y A M D Y W G Q G T L V T V S S
``` huMAb4D5:

V_L (Light chain) (SEQ ID NO: 44):
```
1           10          20          30          40
D I Q M T Q S P S S L S A S V G D R V T I T C R A S Q D V N T A V A W Y Q Q K P G
            50          60          70          80
K A P K L L I Y S A S F L Y S G V P S R F S G S R S G T D F T L T I S S L Q P E D F
            90          100
A T Y Y C Q Q H Y T T P P T F G Q G T K V E I K
```

V_H (heavy chain) (SEQ ID NO: 45):
```
1           10          20          30          40
E V Q L V E S G G G L V Q P G G S L R L S C A A S G F N I K D T Y I H W V R Q A P
            50          60          70          80
G K G L E W V A R I Y P T N G Y T R Y A D S V K G R F T I S A D T S K N T A Y L Q
            90          100         110         120
M N S L R A E D T A V Y Y C S R W G G D G F Y A M D Y W G Q G T L V T V S S
```

Antibody sequence permutations(U.S. Pat. No. 7,435,797 [20] SQ 1 and 2))
huMAb4D5:

V_L (Light chain) (SEQ ID NO: 46):
```
1           10          20          30          40
D I Q M T Q S P S S L S A S V G D R V T I T C R A S Q D V N T A V A W Y Q Q K P G
            50          60          70          80
K A P K L L I Y S A S F L Y S G V P S R F S G S R S G T D F T L T I S S L Q P E D F
            90          100
A T Y Y C Q Q H Y T T P P T F G Q G T K V E I K
```

V_H (heavy chain) (SEQ ID NO: 47):
```
1           10          20          30          40
E V Q L V E S G G G L V Q P G G S L R L S C A A S G F N I K D T Y I H W V R Q A P
            50          60          70          80
G K G L E W V A R I Y P T N G Y T R Y A D S V K G R F T I S A D T S K N T A Y L Q
            90          100         110         120
M N S L R A E D T A V Y Y C S R W G G D G F Y A M D Y W G Q G T L V T V S S
                                            40
``` huMAb4D5-8
(for VL: Q27, D28, N30, T31, A32, Y49, F53, Y55, R66 H91, Y92, T94; for VH: W95, D98, F100, Y100, Y102):

V_L (Light chain): Claim 1 mutation (SEQ ID NO: 48):
```
1           10          20          30          40
D I Q M T Q S P S S L S A S V G D R V T I T C R A S Q D V S S A V A W Y Q Q K P G
            50          60          70          80
K A P K L L I D/W S A S F L Y S G V P S R F S G S R S G T D F T L T I S S L Q P E D F
            90          100
A T Y Y C Q Q H Y T T P P T F G Q G T K V E I K
```

V_H (heavy chain) (SEQ ID NO: 49):
```
1           10          20          30          40
E V Q L V E S G G G L V Q P G G S L R L S C A A S G F N I K D T Y I H W V R Q A P
            50          60          70          80
G K G L E W V A R I Y P T N G Y T R Y A D S V K G R F T I S A D T S K N T A Y L Q
            90          100         110         120
M N S L R A E D T A V Y Y C S R W G G W G P K/L A M D Y W G Q G T L V T V S S
```

Pertuzumab Sequences (US 2010/0015157A1)

$V_L$ (Light chain) (SEQ ID NO: 50):
```
          10            20           30          40
D I Q M T Q S P S S L S A S V G D R V T I T C K A S Q D V S I G V A W Y Q Q K P G
          50            60           70          80
K A P K L L I Y S A S Y R Y T G V P S R F S G S G S T D F T L T I S S L Q P E D
          90           100          110         120
F A T Y Y C Q Q Y Y I Y P Y T F G Q G T K V E I K R T V A A P S V F I F P P S D E Q
         130           140          150         160
L K S G T A S V V C L L N N N F Y P R E A K V Q W K V D N A L Q S G E N S Q E S
         170           180          190         200
V T E Q D S K D S T Y S L S S T L T L S K A D Y E K H K V Y A C E V T H Q G L S S
         210
P V T K S F N R G E C
```

$V_H$ (heavy chain) (SEQ ID NO: 51):
```
          10            20           30          40
E V Q L V E S G G G L V Q P G G S L R L S C A A S G F T F T D Y T M D W V R Q A
          50            60           70          80
P G K G L E W V A D V N P N S G G S I Y N Q R F K G R F T L S V D R S K N T L Y L
          90           100          110         120
Q M N S L R A E D T A V Y Y C A R N L G P S F Y F D Y W G Q G T L V T V S S A S T
         130           140          150         160
K G P S V F P L A P S S K S T S G G T A A L G C L V K D Y F P E P V T V S W N S G
         170           180          190         200
A L T S G V H T F P A V L Q S S G L Y S L S S V V T V P S S S L G T Q T Y I C N V N
         210           220          230         240
H K P S N T K V D K K V E P K S C D K T H T C P P C P A P E L L G G P S V F L F P
         250           260          270         280
P K P K D T L M I S R T P E V T C V V V D V S H E D P E V K F N W Y V D G V E V H
         290           300          310         320
N A K T K P R E E Q Y N S T Y R V V S V L T V L H Q D W L N G K E Y K C K V S N
         330           340          350         360
K A L P A P I E K T I S K A K G Q P R E P Q V Y T L P P S R E E M T K N Q V S L T C
370           380          390          400         410
L V K G F Y P S D I A V E W E S N G Q P E N N Y K T T P P V L D S D G S F F L Y S
         420           430          440
K L T V D K S R W Q Q G N V F S C S V M H E A L H N H Y T Q K S L S L S P G
```

Pertuzumab variants (US2009/0285837 A1)

$V_L$ (Light chain) (SEQ ID NO: 52):
```
          10            20           30          40
V H S D I Q M T Q S P S S L S A S V G D R V T I T C K A S Q D V S I G V A W Y Q Q
          50            60           70          80
K P G K A P K L L I Y S A S Y R Y T G V P S R F S G S G S G T D F T L T I S S L Q P
          90           100          110         120
E D F A T Y Y C Q Q Y Y I Y P Y T F G Q G T K V E I K R T V A A P S V F I F P P S D
         130           140          150         160
E Q L K S G T A S V V C L L N N F Y P R E A K V Q W K V D N A L Q S G N S Q E S
         170           180          190         200
V T E Q D S K D S T Y S L S S T L T L S K A D Y E K H K V Y A C E V T H Q G L S S
         210
P V T K S F N R G E C
```

$V_H$ (Heavy chain) (SEQ ID NO: 53):
```
          10            20           30          40
E V Q L V E S G G G L V Q P G G S L R L S C A A S G F T F T D Y T M D W V R Q A
```

-continued

```
               50                  60                  70                  80
P G K G L E W V A D V N P N S G G S I Y N Q R F K G R F T L S V D R S K N T L Y L
               90                  100                 110                 120
Q M N S L R A E D T A V Y Y C A R N L G P S F Y F D Y W G Q G T L V T V S S A S
               130                 140                 150                 160
T K G P S V F P L A P S S K S T S G G T A A L G C L V K D Y F P E P V T V S W N S
               170                 180                 190                 200
G A L T S G V H T F P A V L Q S S G L Y S L S S V V T V P S S S L G T Q T Y I C N V
               210                 220                 230                 240
N H K P S N T K V D K K V E P K S C D K T H T C P P C P A P E L L G G P S V F L V
               250                 260                 270                 280
P P K P K D T L M I S R T P E V T C V V V D V S H E D P E V K F N W Y V D G V E V
               290                 300                 310                 320
H N A K T K P R E E Q Y N S T Y R V V S V L T V L H Q D W L N G K E Y K C K V S
               330                 340                 350                 360
N K A L P A P I E K T I S K A K G Q P R E P Q V Y T L P P S R E E M T K N Q V S L T
               370                 380                 390                 400
C L V K G F Y P S D I A V E W E S N G Q P E N N Y K T T P P V L D S D G S F F L Y
               410                 420                 430                 440
S K L T V D K S R W Q Q G N V F S C S V M H E A L N H Y T Q K S L S L S P G K
```

Pertuzumab Sequences: humanized 2C4, 7C2, 7F3, 7D3, 3 E 8, 4D5, 2H11, 3 H4 (U.S. Pat. No. 7,097,840)

$V_L$ (Light chain) (SEQ ID NO: 54):
```
1              10                  20                  30                  40
D I Q M T Q S P S S L S A S V G D R V T I T C K A S Q D V S I G V A W Y Q Q K P G
               50                  60                  70                  80
K A P K L L I Y S A S Y R Y T G V P S R F S G S G S G T D F T L T I S S L Q P E D
               90                  100                 110                 120
F A T Y Y C Q Q Y Y I Y P Y T E G Q G T K V E I K R T V A A P S V F I F P P S D E Q
               130                 140                 150                 160
L K S G T A S V V C L L N N N F Y P R E A K V Q W K V D N A L Q S G E N S Q E S
               170                 180                 190                 200
V T E Q D S K D S T Y S L S S T L T L S K A D Y E K H K V Y A C E V T H Q G L S S
               210
P V T K S F N R G E C
```

$V_H$ (heavy chain) (SEQ ID NO: 55):
```
1              10                  20                  30                  40
E V Q L V E S G G G L V Q P G G S L R L S C A A S G F T F T D Y T M D W V R Q A
               50                  60                  70                  80
P G K G L E W V A D V N P N S G G S I Y N Q R F K G R F T L S V D R S K N T L Y L
               90                  100                 110                 120
Q M N S L R A E D T A V Y Y C A R N L G P S F Y F D Y W G Q G T L V T V S S A S T
               130                 140                 150                 160
K G P S V F P L A P S S K S T S G G T A A L G C L V K D Y F P E P V T V S W N S G
               170                 180                 190                 200
A L T S G V H T F P A V L Q S S G L Y S L S S V V T V P S S S L G T Q T Y I C N V N
               210                 220                 230                 240
H K P S N T K V D K K V E P K S C D K T H T C P P C P A P E L L G G P S V F L F P
               250                 260                 270                 280
P K P K D T L M I S R T P E V T C V V V D V S H E D P E V K F N W Y V D G V E V H
               290                 300                 310                 320
N A K T K P R E E Q Y N S T Y R V V S V L T V L H Q D W L N G K E Y K C K V S N
```

```
              330                 340                 350                 360
K A L P A P I E K T I S K A K G Q P R E P Q V Y T L P P S R E E M T K N Q V S L T C 370                 380                 390                 400                 410
L V K G F Y P S D I A V E W E S N G Q P E N N Y K T T P P V L D S D G S F F L Y S 420                 430                 440
K L T V D K S R W Q Q G N V F S C S V M H E A L H N H Y T Q K S L S L S P G
```

Additional anti-ErbB2 antibodies with various properties have been described in Tagliabue et al. *Int. J. Cancer* 47:933-937 (1991); McKenzie et al. *Oncogene* 4:543 (1989); Maier et al. *Cancer Res.* 51:5361 (1991); Bacus et al. *Molecular Carcinogenesis* 3:350 (1990); Stancovski et al. *PNAS* (USA) 88:8691 (1991); Bacus et al. *Cancer Research* 52:2580 (1992); Xu et al. *Int. J Cancer* 53:401-408 (1993); WO 94/00136; Kasprzyk et al. *Cancer Research* 52:2771 (1992); Hancock et al. *Cancer Res.* 51:4575 (1991); Shawver et al. *Cancer Res.* 54:1367 (1994); Arteaga et al. *Cancer Res.* 54:3758 (1994); Harwerth et al. *J Biol Chem.* 267:15160 (1992); U.S. Pat. No. 5,783,186; and Mapper et al. *Oncogene* 14:2099 (1997).

Conjugates include those with a first domain at the amino-terminus and a second domain at the carboxyl-terminus. Conjugates also include those with a first domain at the carboxyl-terminus and a second domain at the amino-terminus. Where additional domains are present (e.g., third, fourth, fifth, sixth, seventh, etc. domains), a first domain is positioned at the NH$_2$-terminus relative to a second domain, or a second domain is positioned at the NH$_2$-terminus relative to a first domain.

Subsequences and amino acid substitutions of the various sequences set forth herein, such as, KFAKFAKKFAKFAKK (SEQ. ID NO. 1), KFAKFAKKFAKFAKKF (SEQ. ID NO. 2), KFAKFAKKFAKFAKKFA (SEQ. ID NO. 3), KFAKFAKKFAKFAKKFAK (SEQ. ID NO. 4), KFAKFAKKFAKFAKKFAKF (SEQ. ID NO. 5), KFAKFAKKFAKFAKKFAKFA (SEQ. ID NO.6) and KFAKFAKKFAKFAKKFAKFAKKFAKFAK (SEQ. ID NO. 7), or a ligand that binds to Her2/neu, are also included. In particular embodiments, a subsequence of a first or second domain has at least 5 to 10, 10 to 15, 15 to 20, 20 to 25, 25 to 30, 30 to 35, 35 to 40, 40 to 50, 50 to 60, 60 to 70, 70 to 80, 80 to 90, 90 to 100, or more amino acid residues.

The invention therefore includes modifications or variations, such as substitutions, additions or deletions of a first or second domain, or both first and second domains. Thus, a conjugate that includes a peptide sequence first or second domain can incorporate any number of conservative or non-conservative amino acid substitutions, as long as such substitutions do not destroy activity (Her2/neu binding or lytic) of first or second domains. Thus, for example, a modified ligand that binds to Her2/neu or a second lytic portion domain can retain at least partial Her2/neu binding or lytic activity, such as cell killing or apoptosis, of an unmodified second domain.

A "conservative substitution" is a replacement of one amino acid by a biologically, chemically or structurally similar residue. Biologically similar means that the substitution is compatible with a biological activity, e.g., lytic activity. Structurally similar means that the amino acids have side chains with similar length, such as alanine, glycine and serine, or having similar size, or the structure of a first, second or additional domain is maintained, such as an amphipathic alpha helix. Chemical similarity means that the residues have the same charge or are both hydrophilic and hydrophobic. Particular examples include the substitution of one hydrophobic residue, such as isoleucine, valine, leucine or methionine for another, or the substitution of one polar residue for another, such as the substitution of arginine for lysine, glutamic for aspartic acids, or glutamine for asparagine, serine for threonine, etc. Routine assays can be used to determine whether a conjugate variant has activity, e.g., binding activity or lytic activity.

Specific examples include a substitution or deletion of one or more amino acid (e.g., 1-3, 3-5, 5-10, 10-20, or more) residues of a peptide first or second domain. A modified conjugate can have a peptide sequence with 50%, 60%, 70%, 75%, 80%, 85%, 90%, 95%, 96%, 97%, 98%, or more identity to a reference sequence (e.g., a first domain, such as a ligand that binds to Her2/neu or a second domain such as KFAKFAKKFAKFAKK (SEQ. ID NO. 1), KFAKFAKKFAKFAKKF (SEQ. ID NO. 2), KFAKFAKKFAKFAKKFA (SEQ. ID NO. 3), KFAKFAKKFAKFAKKFAK (SEQ. ID NO. 4), KFAKFAKKFAKFAKKFAKF (SEQ. ID NO. 5), KFAKFAKKFAKFAKKFAKFA (SEQ. ID NO.6) or KFAKFAKKFAKFAKKFAKFAKKFAKFAK) (SEQ. ID NO. 7).

In a particular embodiment, a conjugate includes a peptide first domain that includes or consists of a ligand that binds to Her2/neu and a second lytic domain that includes or consists of an L- or D-amino acid sequence that includes a peptide selected from KFAKFAKKFAKFAKK (SEQ. ID NO. 1), KFAKFAKKFAKFAKKF (SEQ. ID NO. 2), KFAKFAKKFAKFAKKFA (SEQ. ID NO. 3), KFAKFAKKFAKFAKKFAK (SEQ. ID NO. 4), KFAKFAKKFAKFAKKFAKF (SEQ. ID NO. 5), KFAKFAKKFAKFAKKFAKFA (SEQ. ID NO.6) and KFAKFAKKFAKFAKKFAKFAKKFAKFAK (SEQ. ID NO. 7) having one or more of the K residues substituted with an F or L residue, one or more of the F residues substituted with a K, A or L residue, or one or more of the A residues substituted with a K, F or L residue. In another particular embodiment, a conjugate includes a ligand that binds to Her2/neu and a second domain consisting of an L- or D-amino acid sequence selected from KFAKFAKKFAKFAKK (SEQ. ID NO. 1), KFAKFAKKFAKFAKKF (SEQ. ID NO. 2), KFAKFAKKFAKFAKKFA (SEQ. ID NO. 3), KFAKFAKKFAKFAKKFAK (SEQ. ID NO. 4), KFAKFAKKFAKFAKKFAKF (SEQ. ID NO. 5), KFAKFAKKFAKFAKKFAKFA (SEQ. ID NO.6) and KFAKFAKKFAKFAKKFAKFAKKFAKFAK (SEQ. ID NO. 7) having one or more of the K residues substituted with an F or L residue, one or more of the F residues substituted with a K, A or L residue, or one or more of the A residues substituted with a K, F or L residue (e.g., 12, 13, 15, 16, 17, 18, 19, 20, 22, 23, 24, 25, 26, 27 or 28 residues in length).

The term "identity" and "homology" and grammatical variations thereof mean that two or more referenced entities are the same. Thus, where two amino acid sequences are identical, they have the same amino acid sequence. "Areas, regions or domains of identity" mean that a portion of two or more referenced entities are the same. Thus, where two amino acid sequences are identical or homologous over one or more sequence regions, they share identity in these regions. The term "complementary," when used in reference to a nucleic acid sequence means the referenced regions are 100% complementary, i.e., exhibit 100% base pairing with no mismatches.

Due to variation in the amount of sequence conservation between structurally and functionally related proteins, the amount of sequence identity required to retain a function or activity (e.g., Her2/neu binding or lytic) depends upon the protein, the region and the function or activity of that region. For example, for a lytic peptide sequence multiple PNNPNNP (SEQ. ID NO. 19) sequence repeat patterns or motifs can be present, but one or more interrupted or non-interrupted PNNPNNP (SEQ. ID NO. 19) sequence repeat patterns or motifs need not be present.

The extent of identity between two sequences can be ascertained using a computer program and mathematical algorithm known in the art. Such algorithms that calculate percent sequence identity (homology) generally account for sequence gaps and mismatches over the comparison region. For example, a BLAST (e.g., BLAST 2.0) search algorithm (see, e.g., Altschul et al., *J. Mol. Biol.* 215:403 (1990), publicly available through NCBI) has exemplary search parameters as follows: Mismatch-2; gap open 5; gap extension 2. For polypeptide sequence comparisons, a BLASTP algorithm is typically used in combination with a scoring matrix, such as PAM100, PAM 250, BLOSUM 62 or BLOSUM 50. FASTA (e.g., FASTA2 and FASTA3) and SSEARCH sequence comparison programs are also used to quantitate the extent of identity (Pearson et al., *Proc. Natl. Acad. Sci. USA* 85:2444 (1988); Pearson, *Methods Mol Biol.* 132:185 (2000); and Smith et al., *J. Mol. Biol.* 147:195 (1981)). Programs for quantitating protein structural similarity using Delaunay-based topological mapping have also been developed (Bostick et al., *Biochem Biophys Res Commun.* 304:320 (2003)).

Individual residues and first, second and additional domains can be joined by a covalent or a non-covalent bond. Non-limiting examples of covalent bonds are amide bonds, non-natural and non-amide chemical bonds, which include, for example, glutaraldehyde, N-hydroxysuccinimide esters, bifunctional maleimides, N,N'-dicyclohexylcarbodiimide (DCC) or N,N'-diisopropylcarbodiimide (DIC) Linking groups alternative to amide bonds include, for example, ketomethylene (e.g., —C(=O)—CH$_2$— for —C(=O)—NH—), aminomethylene (CH$_2$—NH), ethylene, olefin (CH=CH), ether (CH$_2$—O), thioether (CH$_2$—S), tetrazole (CN$_4$—), thiazole, retroamide, thioamide, or ester (see, e.g., Spatola (1983) in *Chemistry and Biochemistry of Amino Acids, Peptides and Proteins*, Vol. 7, pp 267-357, "Peptide and Backbone Modifications," Marcel Decker, NY).

First and second domains can be fused or joined immediately adjacent to each other by a covalent or a non-covalent bond. First and second domains can be separated by an intervening region, such as a hinge, spacer or linker positioned between a first and a second domain. In one embodiment, a first and second domain are joined by a carbon chain (e.g., CCCCC (SEQ. ID NO. 16)). Multi-carbon chains include carboxylic acids (e.g., dicarboxylic acids) such as glutaric acid, succinic acid and adipic acid.

In another embodiment, a first and second domain are joined by an amino acid, peptide or a non-peptide hinge, spacer or linker positioned between the first and second domains. Peptide hinge, spacer or linker sequences can be any length, but typically range from about 1-10, 10-20, 20-30, 30-40, or 40-50 amino acid residues. In particular embodiments, a peptide hinge, spacer or linker positioned between a first and second domain is from 1 to 5, 1 to 10, 1 to 20, 1 to 25 L- or D-amino acid residues, or 1 to 6 L- or D-amino acid residues. Particular amino acid residues that are included in sequences positioned between the first and second domains include one or more of or C, A, S or G amino acid residues. Specific non-limiting examples of peptides positioned between the first and second domains include a sequence within or set forth as: GSGGS (SEQ. ID NO. 14), ASAAS (SEQ. ID NO. 15), or a carbon chain such as CCCCCC (SEQ. ID NO. 16). Derivatives of amino acids and peptides can be positioned between the first and second domain. A specific non-limiting example of an amino acid derivative is a lysine derivative, or a 6 carbon linker such as α-amino-caproic acid.

Conjugates with or without a hinge, spacer or linker, or a third, fourth, fifth, sixth, seventh, etc. domain can be entirely composed of natural amino acids or synthetic, non-natural amino acids or amino acid analogues, or can include derivatized forms. In various embodiments, a conjugate includes in a first or second domain one or more D-amino acids substituted for L-amino acids, mixtures of D-amino acids and L-amino acids, or a sequence composed entirely of D-amino acid residues.

Conjugates can contain any combination of non-natural structural components, which are typically from three structural groups: a) residue linkage groups other than the natural amide bond ("peptide bond") linkages; b) non-natural residues in place of naturally occurring amino acid residues; or c) residues which induce secondary structural mimicry, i.e., induce or stabilize a secondary structure, e.g., an alpha helix conformation. Conjugates include cyclic structures such as an end-to-end amide bond between the amino and carboxy-terminus of the molecule or intra- or inter-molecular disulfide bond(s). Conjugates may be modified in vitro or in vivo, e.g., post-translationally modified to include, for example, sugar or carbohydrate residues, phosphate groups, fatty acids, lipids, etc.

Specific examples of an addition include a third, fourth, fifth, sixth or seventh domain. Conjugates with a first and second domain therefore include one or more additional domains (third, fourth, fifth, sixth, seventh, etc.) covalently linked thereto to impart a distinct or complementary function or activity. Exemplary additional domains include domains facilitating isolation, which include, for example, metal chelating peptides such as polyhistidine tracts and histidine-tryptophan modules that allow purification on immobilized metals; protein A domains that allow purification on immobilized immunoglobulin; and domain utilized in the FLAGS extension/affinity purification system (Immunex Corp, Seattle Wash.). Optional inclusion of a cleavable sequence such as Factor Xa or enterokinase between a purification domain and the conjugate can be used to facilitate purification. For example, an expression vector can include a conjugate-encoding nucleic acid sequence linked to six histidine residues followed by a thioredoxin and an enterokinase cleavage site. The histidine residues facilitate detection and purification of the conjugate while the enterokinase cleavage site provides a means for purifying the construct from the remainder of the protein (see e.g., Kroll, *DNA Cell. Biol.* 12:441 (1993)).

Conjugate activity can be affected by various factors and therefore conjugates can be designed or optimized by taking into consideration one or more of these factors. Such factors include, for example, length, which can affect toxicity to cells. Cell killing activity of alpha helix forming lytic peptide domains can also depend on the stability of the helix. Hinge and spacers can affect membrane interaction of a first domain and the helical structure of a peptide lytic domain. The charge of lytic peptide domains, which is determined in part by the particular amino acid residues present in the domain, also affects cell killing potency. The positioning of the ligand that binds to Her2/neu relative to the lytic domain (N- or C-terminus) also can affect cell killing activity of conjugates.

Conjugate in vivo half-life can be increased by constructing peptide domains with one or more non-naturally occurring amino acids or derivatives. For example, conjugates with D-amino acids (e.g., up to 30%, 40%, 50%, 60%, or more of all residues are D-enantiomers) are resistant to serum proteolysis and therefore can be active for longer times thereby increasing in vivo potency. Furthermore, constructing peptide domains with one or more non-naturally occurring amino acids or derivatives can reduce hemolytic activity. Such conjugates with D-enantiomers also have a greater tendency to be monomeric in solution-they do not significantly aggregate.

Peptides and peptidomimetics can be produced and isolated using methods known in the art. Peptides can be synthesized, whole or in part, using chemical methods known in the art (see, e.g., Caruthers (1980). *Nucleic Acids Res. Symp. Ser.* 215; Horn (1980); and Banga, A. K., *Therapeutic Peptides and Proteins, Formulation, Processing and Delivery Systems* (1995) Technomic Publishing Co., Lancaster, Pa.). Peptide synthesis can be performed using various solid-phase techniques (see, e.g., *Roberge Science* 269:202 (1995); *Merrifield, Methods Enzymol.* 289:3(1997)) and automated synthesis may be achieved, e.g., using the ABI 431A Peptide Synthesizer (Perkin Elmer) in accordance with the manufacturer's instructions. Peptides and peptide mimetics can also be synthesized using combinatorial methodologies. Synthetic residues and polypeptides incorporating mimetics can be synthesized using a variety of procedures and methodologies known in the art (see, e.g., *Organic Syntheses* Collective Volumes, Gilman, et al. (Eds) John Wiley & Sons, Inc., NY). Modified peptides can be produced by chemical modification methods (see, for example, Belousov, *Nucleic Acids Res.* 25:3440 (1997); Frenkel, *Free Radic. Biol. Med.* 19:373 (1995); and Blommers, *Biochemistry* 33:7886 (1994).

The invention further provides nucleic acids encoding the conjugates of the invention and vectors that include nucleic acid that encodes conjugates. Nucleic acid, which can also be referred to herein as a gene, polynucleotide, nucleotide sequence, primer, oligonucleotide or probe refers to natural or modified purine- and pyrimidine-containing polymers of any length, either polyribonucleotides or polydeoxyribonucleotides or mixed polyribo-polydeoxyribo nucleotides and α-anomeric forms thereof. The two or more purine- and pyrimidine-containing polymers are typically linked by a phosphoester bond or analog thereof. The terms can be used interchangeably to refer to all forms of nucleic acid, including deoxyribonucleic acid (DNA) and ribonucleic acid (RNA). The nucleic acids can be single strand, double, or triplex, linear or circular. Nucleic acids include genomic DNA, cDNA, and antisense. RNA nucleic acid can be spliced or unspliced mRNA, rRNA, tRNA or antisense. Nucleic acids include naturally occurring, synthetic, as well as nucleotide analogues and derivatives.

As a result of the degeneracy of the genetic code, nucleic acids include sequences degenerate with respect to sequences encoding conjugates of the invention. Thus, degenerate nucleic acid sequences encoding conjugates are provided.

Nucleic acid can be produced using any of a variety of known standard cloning and chemical synthesis methods, and can be altered intentionally by site-directed mutagenesis or other recombinant techniques known to one skilled in the art. Purity of polynucleotides can be determined through sequencing, gel electrophoresis, UV spectrometry.

Nucleic acids may be inserted into a nucleic acid construct in which expression of the nucleic acid is influenced or regulated by an "expression control element," referred to herein as an "expression cassette." The term "expression control element" refers to one or more nucleic acid sequence elements that regulate or influence expression of a nucleic acid sequence to which it is operatively linked. An expression control element can include, as appropriate, promoters, enhancers, transcription terminators, gene silencers, a start codon (e.g., ATG) in front of a protein-encoding gene, etc.

An expression control element operatively linked to a nucleic acid sequence controls transcription and, as appropriate, translation of the nucleic acid sequence. The term "operatively linked" refers to a juxtaposition wherein the referenced components are in a relationship permitting them to function in their intended manner. Typically expression control elements are juxtaposed at the 5' or the 3' ends of the genes but can also be intronic.

Expression control elements include elements that activate transcription constitutively, that are inducible (i.e., require an external signal for activation), or derepressible (i.e., require a signal to turn transcription off; when the signal is no longer present, transcription is activated or "derepressed"). Also included in the expression cassettes of the invention are control elements sufficient to render gene expression controllable for specific cell-types or tissues (i.e., tissue-specific control elements). Typically, such elements are located upstream or downstream (i.e., 5' and 3') of the coding sequence. Promoters are generally positioned 5' of the coding sequence. Promoters, produced by recombinant DNA or synthetic techniques, can be used to provide for transcription of the polynucleotides of the invention. A "promoter" is meant a minimal sequence element sufficient to direct transcription.

Nucleic acids may be inserted into a plasmid for propagation into a host cell and for subsequent genetic manipulation if desired. A plasmid is a nucleic acid that can be stably propagated in a host cell; plasmids may optionally contain expression control elements in order to drive expression of the nucleic acid. A vector is used herein synonymously with a plasmid and may also include an expression control element for expression in a host cell. Plasmids and vectors generally contain at least an origin of replication for propagation in a cell and a promoter. Plasmids and vectors are therefore useful for genetic manipulation of conjugate encoding nucleic acids, producing conjugates or antisense nucleic acid, and expressing conjugates in host cells and organisms, for example.

Bacterial system promoters include T7 and inducible promoters such as pL of bacteriophage λ, plac, ptrp, ptac (ptrp-lac hybrid promoter) and tetracycline responsive promoters. Insect cell system promoters include constitutive or inducible promoters (e.g., ecdysone). Mammalian cell constitutive promoters include SV40, RSV, bovine papilloma virus (BPV) and other virus promoters, or inducible promoters derived from the genome of mammalian cells (e.g., metallothionein IIA promoter; heat shock promoter) or from mammalian viruses (e.g., the adenovirus late promoter; the inducible mouse mammary tumor virus long terminal repeat). Alternatively, a retroviral genome can be genetically modified for introducing and directing expression of a conjugate in appropriate host cells.

Expression systems further include vectors designed for in vivo use. Particular non-limiting examples include adenoviral vectors (U.S. Pat. Nos. 5,700,470 and 5,731,172), adeno-associated vectors (U.S. Pat. No. 5,604,090), herpes simplex virus vectors (U.S. Pat. No. 5,501,979), retroviral vectors (U.S. Pat. Nos. 5,624,820, 5,693,508 and 5,674,703), BPV vectors (U.S. Pat. No. 5,719,054) and CMV vectors (U.S. Pat. No. 5,561,063).

Yeast vectors include constitutive and inducible promoters (see, e.g., Ausubel et al., In: *Current Protocols in Molecular Biology*, Vol. 2, Ch. 13, ed., Greene Publish. Assoc. & Wiley Interscience, 1988; Grant et al. *Methods in Enzymology*, 153:516 (1987), eds. Wu & Grossman; Bitter *Methods in Enzymology*, 152:673 (1987), eds. Berger & Kimmel, Acad. Press, N.Y.; and, Strathern et al., *The Molecular Biology of the Yeast Saccharomyces* (1982) eds. Cold Spring Harbor Press, Vols. I and II). A constitutive yeast promoter such as ADH or LEU2 or an inducible promoter such as GAL may be used (R. Rothstein In: *DNA Cloning, A Practical Approach*, Vol. 11, Ch. 3, ed. D. M. Glover, IRL Press, Wash., D.C., 1986). Vectors that facilitate integration of foreign nucleic acid sequences into a yeast chromosome, via homologous recombination for example, are known in the art. Yeast artificial chromosomes (YAC) are typically used when the inserted polynucleotides are too large for more conventional vectors (e.g., greater than about 12 Kb).

Expression vectors also can contain a selectable marker conferring resistance to a selective pressure or identifiable marker (e.g., beta-galactosidase), thereby allowing cells having the vector to be selected for, grown and expanded. Alternatively, a selectable marker can be on a second vector that is cotransfected into a host cell with a first vector containing a nucleic acid encoding a conjugate.

Selection systems include but are not limited to herpes simplex virus thymidine kinase gene (Wigler et al., *Cell* 11:223 (1977)), hypoxanthine-guanine phosphoribosyltransferase gene (Szybalska et al., *Proc. Natl. Acad. Sci. USA* 48:2026 (1962)), and adenine phosphoribosyltransferase (Lowy et al., *Cell* 22:817 (1980)) genes which can be employed in tk-, hgprt$^-$ or aprt$^-$ cells, respectively. Additionally, antimetabolite resistance can be used as the basis of selection for dhfr, which confers resistance to methotrexate (O'Hare et al., *Proc. Natl. Acad. Sci. USA* 78:1527 (1981)); the gpt gene, which confers resistance to mycophenolic acid (Mulligan et al., *Proc. Natl. Acad. Sci. USA* 78:2072 (1981)); neomycin gene, which confers resistance to aminoglycoside G-418 (Colberre-Garapin et al., *J. Mol. Biol.* 150:1(1981)); puromycin; and hygromycin gene, which confers resistance to hygromycin (Santerre et al., *Gene* 30:147 (1984)). Additional selectable genes include trpB, which allows cells to utilize indole in place of tryptophan; hisD, which allows cells to utilize histinol in place of histidine (Hartman et al., *Proc. Natl. Acad. Sci. USA* 85:8047 (1988)); and ODC (ornithine decarboxylase), which confers resistance to the ornithine decarboxylase inhibitor, 2-(difluoromethyl)-DL-ornithine, DFMO (McConlogue (1987) In: Current Communications in Molecular Biology, Cold Spring Harbor Laboratory).

Host cells that express conjugates, and host cells transformed with nucleic acids encoding conjugates and vectors including a nucleic acid that encodes the conjugates are also provided. In one embodiment, a host cell is a prokaryotic cell. In another embodiment, a host cell is a eukaryotic cell. In various aspects, the eukaryotic cell is a yeast or mammalian (e.g., human, primate, etc.) cell.

As used herein, a "host cell" is a cell into which a nucleic acid is introduced that can be propagated, transcribed, or encoded conjugate expressed. The term also includes any progeny or subclones of the host cell. Host cells include cells that express conjugates.

Host cells include but are not limited to microorganisms such as bacteria and yeast; and plant, insect and mammalian cells. For example, bacteria transformed with recombinant bacteriophage nucleic acid, plasmid nucleic acid or cosmid nucleic acid expression vectors; yeast transformed with recombinant yeast expression vectors; plant cell systems infected with recombinant virus expression vectors (e.g., cauliflower mosaic virus, CaMV; tobacco mosaic virus, TMV) or transformed with recombinant plasmid expression vectors (e.g., Ti plasmid); insect cell systems infected with recombinant virus expression vectors (e.g., baculovirus); and animal cell systems infected with recombinant virus expression vectors (e.g., retroviruses, adenovirus, vaccinia virus), or transformed animal cell systems engineered for transient or stable propagation or expression.

Conjugates, nucleic acids encoding conjugates, vectors and host cells expressing conjugates or transformed with nucleic acids encoding conjugates and antisense include isolated and purified forms. The term "isolated," when used as a modifier of an invention composition, means that the composition is made by the hand of man or is separated, substantially completely or at least in part, from the naturally occurring in vivo environment. Generally, an isolated composition is substantially free of one or more materials with which it normally associates with in nature, for example, one or more protein, nucleic acid, lipid, carbohydrate, cell membrane. The term "isolated" does not exclude alternative physical forms of the composition, such as multimers/oligomers, variants, modifications or derivatized forms, or forms expressed in host cells produced by the hand of man. The term "isolated" also does not exclude forms (e.g., pharmaceutical formulations and combination compositions) in which there are combinations therein, any one of which is produced by the hand of man.

An "isolated" composition can also be "purified" when free of some, a substantial number of, most or all of the materials with which it typically associates with in nature. Thus, an isolated conjugate that also is substantially pure does not include polypeptides or polynucleotides present among millions of other sequences, such as proteins of a protein library or nucleic acids in a genomic or cDNA library, for example. A "purified" composition can be combined with one or more other molecules.

In accordance with the invention, there are provided mixtures of conjugates and combination compositions. In one embodiment, a mixture includes one or more conjugates and a pharmaceutically acceptable carrier or excipient. In another embodiment, a mixture includes one or more conjugates and an anti-cell proliferative, anti-tumor, anti-cancer, or anti-neoplastic treatment or agent. In a further embodiment, a mixture includes one or more conjugates and an immune enhancing agent. Combinations, such as one or more conjugates in a pharmaceutically acceptable carrier or excipient, with one or more of an anti-cell proliferative, anti-tumor, anti-cancer, or anti-neoplastic treatment or agent, and an immune enhancing treatment or agent, are also provided.

Conjugates of the invention, such as polypeptides having an amino acid sequence including a first ligand that binds to Her2/neu (Her2/neu binding moiety) domain and a second lytic domain, can be used to target cells for lysis, cell death or apoptosis. Such cells can be selectively targeted. For example a cell that expresses Her2/neu can be targeted by a conjugate and thereby be preferentially killed compared to cells that express none or less of the Her2/neu.

In accordance with the invention, there are provided methods of reducing or inhibiting proliferation of a cell that expresses Her2/neu and methods of reducing or inhibiting cell proliferation. In one embodiment, a method includes contacting a cell with a conjugate in an amount sufficient to reduce or inhibit proliferation of the cell. In another embodiment, a method includes contacting a cell with a conjugate in an amount sufficient to reduce or inhibit cell proliferation.

Also provided are methods of reducing or inhibiting proliferation of a hyperproliferative cell that expresses Her2/neu, and methods of reducing or inhibiting proliferation of hyperproliferating cells that express Her2/neu. In one embodiment, a method includes contacting a hyperproliferative cell or hyperproliferating cells with a conjugate in an amount sufficient to reduce or inhibit proliferation.

Further provided are methods of reducing or inhibiting proliferation of a non-metastatic or metastatic neoplastic, cancer, tumor and malignant cells that express Her2/neu. In one embodiment, a method includes contacting a neoplastic, cancer, tumor or malignant cell with a conjugate in an amount sufficient to reduce or inhibit proliferation of the cell.

Still further provided are methods of reducing or inhibiting proliferation of a dormant or non-dividing non-metastatic or metastatic neoplastic, cancer, tumor and malignant cells that express Her2/neu. In one embodiment, a method includes contacting a dormant or non-dividing neoplastic, cancer, tumor or malignant cell with a conjugate in an amount sufficient to reduce or inhibit proliferation of the dormant or non-dividing cell.

Additionally provided are methods of selectively reducing or inhibiting proliferation of a cell (e.g., a hyperproliferating cell) that expresses Her2/neu. In one embodiment, a method includes contacting the cell with a conjugate in an amount sufficient to reduce or inhibit proliferation of the cell (e.g., hyperproliferating cell), wherein the conjugate binds to Her2/neu expressed by the cell.

Yet additionally provided are methods of selectively reducing or inhibiting proliferation of a neoplastic, tumor, cancer or malignant cell that expresses that expresses Her2/neu. In one embodiment, a method includes contacting the cell with a conjugate in an amount sufficient to reduce or inhibit proliferation of the neoplastic, tumor, cancer or malignant cell, wherein the conjugate binds to the Her2/neu expressed by the cell.

The term "contacting" means direct or indirect binding or interaction between two or more entities (e.g., between a conjugate and a cell). Contacting as used herein includes in solution, in solid phase, in vitro, ex vivo, in a cell and in vivo. Contacting in vivo can be referred to as administering, or administration or delivery.

Cells to target for reducing or inhibiting proliferation, non-selectively or selectively, include cells that express Her2/neu. Non-limiting exemplary cells include breast, ovarian, uterine, cervical, stomach, lung, gastric, colon, bladder, glial, hematologic and endometrial cells. Thus, target cells include cells that express Her2/neu.

Conjugates and methods of the invention are also applicable to treating undesirable or aberrant cell proliferation and hyperproliferative disorders, which include cells expressing Her2/neu. Thus, in accordance with the invention, methods of treating undesirable or aberrant cell proliferation and hyperproliferative disorders are provided. In one embodiment, a method includes administering to a subject (in need of treatment) an amount of a conjugate sufficient to treat the undesirable or aberrant cell proliferation or the hyperproliferative disorder.

The term "hyperproliferative disorder" refers to any undesirable or aberrant cell survival (e.g., failure to undergo programmed cell death or apoptosis), growth or proliferation. Such disorders include benign hyperplasias, non-metastatic and metastatic neoplasias, cancers, tumors and malignancies. Undesirable or aberrant cell proliferation and hyperproliferative disorders can affect any cell, tissue, organ in a subject. Undesirable or aberrant cell proliferation and hyperproliferative disorders can be present in a subject, locally, regionally or systemically. A hyperproliferative disorder can arise from a multitude of tissues and organs, including but not limited to breast, lung (e.g., small cell or non-small cell), thyroid, head and neck, brain, nasopharynx, throat, nose or sinuses, lymphoid, adrenal gland, pituitary gland, thyroid, lymph, gastrointestinal (mouth, esophagus, stomach, duodenum, ileum, jejunum (small intestine), colon, rectum), genito-urinary tract (uterus, ovary, vagina, cervix, endometrium, fallopian tube, bladder, testicle, penis, prostate), kidney, pancreas, liver, bone, bone marrow, lymph, blood (hematologic), brain (glial), muscle, skin, and stem cells, which may or may not metastasize to other secondary sites, regions or locations.

Conjugates and methods of the invention are also applicable to metastatic or non-metastatic tumor, cancer, malignancy or neoplasia of any cell, organ or tissue origin. Such disorders can affect virtually any cell or tissue type, e.g., carcinoma, sarcoma, melanoma, neural, and reticuloendothelial or hematopoietic neoplastic disorders (e.g., myeloma, lymphoma or leukemia).

As used herein, the terms "neoplasia" and "tumor" refer to a cell or population of cells whose growth, proliferation or survival is greater than growth, proliferation or survival of a normal counterpart cell, e.g. a cell proliferative or differentiative disorder. A tumor is a neoplasia that has formed a distinct mass or growth. A "cancer" or "malignancy" refers to a neoplasia or tumor that can invade adjacent spaces, tissues or organs. A "metastasis" refers to a neoplasia, tumor, cancer or malignancy that has disseminated or spread from its primary site to one or more secondary sites, locations or regions within the subject, in which the sites, locations or regions are distinct from the primary tumor or cancer. All or a portion of such cells can express Her2/neu and can therefore be targeted with conjugates in accordance with the invention.

Neoplastic, tumor, cancer and malignant cells (metastatic or non-metastatic) include dormant or residual neoplastic, tumor, cancer and malignant cells, all or a portion of which express Her2/neu. Such cells typically consist of remnant tumor cells that are not dividing (G0-G1 arrest). These cells can persist in a primary site or as disseminated neoplastic, tumor, cancer or malignant cells as a minimal residual disease. These dormant neoplastic, tumor, cancer or malignant cells remain asymptomatic, but can develop severe symptoms and death once these dormant cells proliferate. Invention methods can be used to reduce or inhibit proliferation of dormant neoplastic, tumor, cancer or malignant cells, which can in turn inhibit or reduce tumor or cancer relapse, or tumor or cancer metastasis or progression.

In accordance with the invention, methods of treating a subject having a metastatic or non-metastatic tumor, cancer, malignancy or neoplasia are provided. In one embodiment, a method includes administering to a subject (in need of treatment) an amount of a conjugate of sufficient to treat (e.g., reduce or inhibit proliferation) the metastatic or non-metastatic tumor, cancer, malignancy or neoplasia.

The metastatic or non-metastatic tumor, cancer, malignancy or neoplasia may be in any stage, e.g., early or advanced, such as a stage I, II, III, IV or V tumor. The metastatic or non-metastatic tumor, cancer, malignancy or neoplasia may have been subject to a prior treatment or be stabilized (non-progressing) or in remission.

In terms of metastasis, invention methods can be used to reduce or inhibit metastasis of a primary tumor or cancer to other sites, or the formation or establishment of metastatic tumors or cancers at other sites distal from the primary tumor or cancer thereby inhibiting or reducing tumor or cancer relapse or tumor or cancer progression. Thus, methods of the invention include, among other things, 1) reducing or inhibiting growth, proliferation, mobility or invasiveness of tumor or cancer cells that potentially or do develop metastases (e.g., disseminated tumor cells, DTC); 2) reducing or inhibiting formation or establishment of metastases arising from a primary tumor or cancer to one or more other sites, locations or regions distinct from the primary tumor or cancer; 3) reducing or inhibiting growth or proliferation of a metastasis at one or more other sites, locations or regions distinct from the primary tumor or cancer after a metastasis has formed or has been established; and 4) reducing or inhibiting formation or establishment of additional metastasis after the metastasis has been formed or established.

Cells of a metastatic or non-metastatic tumor, cancer, malignancy or neoplasia (all or a portion of which express Her2/neu) may be aggregated in a "solid" cell mass or be dispersed or diffused. A "solid" tumor refers to cancer, neoplasia or metastasis that typically aggregates together and forms a mass. Specific non-limiting examples include breast, ovarian, uterine, cervical, stomach, lung, gastric, colon, bladder, glial, and endometrial tumors/cancers.

Carcinomas, which refer to malignancies of epithelial or endocrine tissue, include respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from the uterus, cervix, lung, prostate, breast, head and neck, colon, pancreas, testes, adrenal, kidney, esophagus, stomach, liver and ovary. The term also includes carcinosarcomas, e.g., which include malignant tumors composed of carcinomatous and sarcomatous tissues. Adenocarcinoma includes a carcinoma of a glandular tissue, or in which the tumor forms a gland like structure.

Sarcomas refer to malignant tumors of mesenchymal cell origin. Exemplary sarcomas include for example, lymphosarcoma, liposarcoma, osteosarcoma, chondrosarcoma, leiomyosarcoma, rhabdomyosarcoma and fibrosarcoma.

Neural neoplasias include glioma, glioblastoma, meningioma, neuroblastoma, retinoblastoma, astrocytoma and oligodendrocytoma.

A "liquid tumor," which refers to neoplasia that is dispersed or is diffuse in nature, as they do not typically form a solid mass. Particular examples include neoplasia of the reticuloendothelial or hematopoietic system, such as lymphomas, myelomas and leukemias. Non-limiting examples of leukemias include acute and chronic lymphoblastic, myeolblastic and multiple myeloma. Typically, such diseases arise from poorly differentiated acute leukemias, e.g., erythroblastic leukemia and acute megakaryoblastic leukemia. Specific myeloid disorders include, but are not limited to, acute promyeloid leukemia (APML), acute myelogenous leukemia (AML) and chronic myelogenous leukemia (CML). Lymphoid malignancies include, but are not limited to, acute lymphoblastic leukemia (ALL), which includes B-lineage ALL (B-ALL) and T-lineage ALL (T-ALL), chronic lymphocytic leukemia (CLL), prolymphocytic leukemia (PLL), hairy cell leukemia (HLL) and Waldenstroem's macroglobulinemia (WM). Specific malignant lymphomas include, non-Hodgkin lymphoma and variants, peripheral T cell lymphomas, adult T cell leukemia/lymphoma (ATL), cutaneous T-cell lymphoma (CTCL), large granular lymphocytic leukemia (LGF), Hodgkin's disease and Reed-Sternberg disease.

As disclosed herein, undesirable or aberrant cell proliferation or hyperproliferative disorders can occur in uterus, breast, vagina, cervix, endometrium and fallopian tube. Thus, in accordance with the invention, there are provided methods of treating uterus, breast, vagina, cervix, endometrium and fallopian tube hyperproliferative disorders. In one embodiment, a method includes administering to a subject an amount of a conjugate sufficient to treat a uterus, breast, vagina, cervix, endometrium or fallopian tube hyperproliferative disorder.

Any composition, treatment, protocol, therapy or regimen having an anti-cell proliferative activity or effect can be combined with a conjugate or used in combination in a method of the invention. Conjugates and methods of the invention therefore include anti-proliferative, anti-tumor, anti-cancer, anti-neoplastic and anti-metastatic treatments, protocols and therapies, which include any other composition, treatment, protocol or therapeutic regimen that inhibits, decreases, retards, slows, reduces or prevents a hyperproliferative disorder, such as tumor, cancer, malignant or neoplastic growth, progression, metastasis, proliferation or survival, or worsening in vitro or in vivo. Particular non-limiting examples of an anti-proliferative (e.g., tumor) therapy include chemotherapy, immunotherapy, radiotherapy (ionizing or chemical), local thermal (hyperthermia) therapy, surgical resection and vaccination. A conjugate can be administered prior to, substantially contemporaneously with or following administration of the anti-cell proliferative, anti-neoplastic, anti-tumor, anti-cancer, anti-metastatic or immune-enhancing treatment or therapy. A conjugate can be administered as a combination composition with the anti-cell proliferative, anti-neoplastic, anti-tumor, anti-cancer, anti-metastatic or immune-enhancing treatment or therapy, metastatic or non-metastatic tumor, cancer, malignancy or neoplasia.

Anti-proliferative, anti-neoplastic, anti-tumor, anti-cancer and anti-metastatic compositions, therapies, protocols or treatments include those that prevent, disrupt, interrupt, inhibit or delay cell cycle progression or cell proliferation; stimulate or enhance apoptosis or cell death, inhibit nucleic acid or protein synthesis or metabolism, inhibit cell division, or decrease, reduce or inhibit cell survival, or production or utilization of a necessary cell survival factor, growth factor or signaling pathway (extracellular or intracellular). Non-limiting examples of chemical agent classes having anti-cell proliferative, anti-neoplastic, anti-tumor, anti-cancer and anti-metastatic activities include alkylating agents, antimetabolites, plant extracts, plant alkaloids, nitrosoureas, hormones, nucleoside and nucleotide analogues. Specific examples of drugs having anti-cell proliferative, anti-neoplastic, anti-tumor, anti-cancer and anti-metastatic activities include cyclophosphamide, azathioprine, cyclosporin A, prednisolone, melphalan, chlorambucil, mechlorethamine, busulphan, methotrexate, 6-mercaptopurine, thioguanine, 5-fluorouracil, cytosine arabinoside, AZT, 5-azacytidine (5-AZC) and 5-azacytidine related compounds such as decitabine (5-aza-2'deoxycytidine), cytarabine, 1-beta-D-arabinofuranosyl-5-azacytosine and dihydro-5-azacytidine, bleomycin, actinomycin D, mithramycin, mitomycin C, carmustine, lomustine, semustine, streptozotocin, hydroxyurea, cisplatin, mitotane, procarbazine, dacarbazine, taxol, vinblastine, vincristine, doxorubicin and dibromomannitol etc.

Additional agents that are applicable with conjugates and methods are known in the art and can be employed. For example, biologicals such as antibodies, cell growth factors, cell survival factors, cell differentiative factors, cytokines and chemokines can be administered. Non-limiting examples of monoclonal antibodies include rituximab (Rituxan®), trastuzumab (Herceptin), pertuzumab (Omnitarg), bevacizumab (Avastin), cetuximab (Erbitux), alemtuzumab (Campath), panitumumab (Vectibix), ibritumomab tiuxetan (Zevalin), tositumomab (Bexxar) etc. which can be used in combination with, inter alia, a conjugate in accordance with the invention. Other targeted drugs that are applicable for use with the conjugates are imatinib (Gleevec), gefitinib (Iressa), bortzomib (Velcade), lapatinib (Tykerb), sunitinib (Sutent), sorafenib (Nevaxar), nilotinib (Tasigna) etc. Non-limiting examples of cell growth factors, cell survival factors, cell differentiative factors, cytokines and chemokines include IL-2, IL-1α, IL-1β, IL-3, IL-6, IL-7, granulocyte-macrophage-colony stimulating factor (GMCSF), IFN-γ, IL-12, TNF-α, TNFβ, MIP-1α, MIP-1β, RANTES, SDF-1, MCP-1, MCP-2, MCP-3, MCP-4, eotaxin, eotaxin-2, I-309/TCA3, ATAC, HCC-1, HCC-2, HCC-3, LARC/MIP-3α, PARC, TARC, CKβ, CKβ6, CKβ7, CKβ8, CKβ9, CKβ11, CKβ12, C10, IL-8, GROα, GROβ, ENA-78, GCP-2, PBP/CTAPIIIβ-TG/NAP-2, Mig, PBSF/SDF-1 and lymphotactin.

Additional non-limiting examples include immune-enhancing treatments and therapies, which include cell based therapies. In particular, immune-enhancing treatments and therapies include administering lymphocytes, plasma cells, macrophages, dendritic cells, NK cells and B-cells.

Methods of treating a metastatic or non-metastatic tumor, cancer, malignancy or neoplasia, methods of treating a subject in need of treatment due to having or at risk of having a metastatic or non-metastatic tumor, cancer, malignancy or neoplasia, and methods of increasing effectiveness or improving an anti-proliferative, anti-tumor, anti-cancer, anti-neoplasia or anti-malignancy, therapy are provided. In respective embodiments, a method includes administering to a subject with or at risk of a metastatic or non-metastatic tumor, cancer, malignancy or neoplasia, an amount of a conjugate sufficient to treat the metastatic or non-metastatic tumor, cancer, malignancy or neoplasia; administering to the subject an amount of a conjugate sufficient to treat the subject; and administering to a subject that is undergoing or has undergone metastatic or non-metastatic tumor, cancer, malignancy or neoplasia therapy, an amount of a conjugate sufficient to increase effectiveness of the anti-proliferative, anti-tumor, anti-cancer, anti-neoplasia or anti-malignancy therapy.

Methods of the invention may be practiced prior to (i.e. prophylaxis), concurrently with or after evidence of the presence of undesirable or aberrant cell proliferation or a hyperproliferative disorder, disease or condition begins (e.g., one or more symptoms). Administering a conjugate prior to, concurrently with or immediately following development of a symptom of undesirable or aberrant cell proliferation or a hyperproliferative disorder may decrease the occurrence, frequency, severity, progression, or duration of one or more symptoms of the undesirable or aberrant cell proliferation or a hyperproliferative disorder, disease or condition in the subject. In addition, administering a conjugate prior to, concurrently with or immediately following development of one or more symptoms of the undesirable or aberrant cell proliferation or a hyperproliferative disorder, disease or condition may inhibit, decrease or prevent the spread or dissemination of hyperproliferating cells (e.g., metastasis) to other sites, regions, tissues or organs in a subject, or establishment of hyperproliferating cells (e.g., metastasis) at other sites, regions, tissues or organs in a subject.

Conjugates and the methods of the invention, such as treatment methods, can provide a detectable or measurable therapeutic benefit or improvement to a subject. A therapeutic benefit or improvement is any measurable or detectable, objective or subjective, transient, temporary, or longer-term benefit to the subject or improvement in the condition, disorder or disease, an adverse symptom, consequence or underlying cause, of any degree, in a tissue, organ, cell or cell population of the subject. Therapeutic benefits and improvements include, but are not limited to, reducing or decreasing occurrence, frequency, severity, progression, or duration of one or more symptoms or complications associated with a disorder, disease or condition, or an underlying cause or consequential effect of the disorder, disease or condition. Conjugates and methods of the invention therefore include providing a therapeutic benefit or improvement to a subject.

In a method of the invention in which a therapeutic benefit or improvement is a desired outcome, a conjugate of the invention can be administered in a sufficient or effective amount to a subject in need thereof. An "amount sufficient" or "amount effective" refers to an amount that provides, in single or multiple doses, alone or in combination, with one or more other compositions (therapeutic agents such as a chemotheraputic or immune stimulating drug), treatments, protocols, or therapeutic regimens agents, a detectable response of any duration of time (long or short term), a desired outcome in or a benefit to a subject of any measurable or detectable degree or for any duration of time (e.g., for hours, days, months, years, or cured). The doses or "sufficient amount" or "effective amount" for treatment (e.g., to provide a therapeutic benefit or improvement) typically are effective to ameliorate a disorder, disease or condition, or one, multiple or all adverse symptoms, consequences or complications of the disorder, disease or condition, to a measurable extent, although reducing or inhibiting a progression or worsening of the disorder, disease or condition or a symptom, is considered a satisfactory outcome.

The term "ameliorate" means a detectable objective or subjective improvement in a subject's condition. A detectable improvement includes a subjective or objective reduction in the occurrence, frequency, severity, progression, or duration of a symptom caused by or associated with a disorder, disease or condition, an improvement in an underlying cause or a consequence of the disorder, disease or condition, or a reversal of the disorder, disease or condition.

Treatment can therefore result in inhibiting, reducing or preventing a disorder, disease or condition, or an associated symptom or consequence, or underlying cause; inhibiting, reducing or preventing a progression or worsening of a disorder, disease, condition, symptom or consequence, or underlying cause; or further deterioration or occurrence of one or more additional symptoms of the disorder, disease condition, or symptom. Thus, a successful treatment outcome leads to a "therapeutic effect," or "benefit" or inhibiting, reducing or preventing the occurrence, frequency, severity, progression, or duration of one or more symptoms or underlying causes or consequences of a condition, disorder, disease or symptom in the subject. Treatment methods affecting one or more underlying causes of the condition, disorder, disease or symptom are therefore considered to be beneficial. Stabilizing or inhibiting progression or worsening of a disorder or condition is also a successful treatment outcome.

A therapeutic benefit or improvement therefore need not be complete ablation of any one, most or all symptoms, complications, consequences or underlying causes associated with the condition, disorder or disease. Thus, a satisfactory endpoint is achieved when there is an incremental improvement in a subject's condition, or a partial reduction in the occurrence, frequency, severity, progression, or duration, or inhibition or reversal, of one or more associated adverse symptoms or complications or consequences or underlying causes, worsening or progression (e.g., stabilizing one or more symptoms or complications of the condition, disorder or disease), of one or more of the physiological, biochemical or cellular manifestations or characteristics of the disorder or disease, over a short or long duration of time (hours, days, weeks, months, etc.).

In particular embodiments, a method of treatment results in partial or complete destruction of a metastatic or non-metastatic tumor, cancer, malignant or neoplastic cell mass, volume, size or numbers of cells; results in stimulating, inducing or increasing metastatic or non-metastatic tumor, cancer, malignant or neoplastic cell necrosis, lysis or apoptosis; results in reducing metastatic or non-metastatic tumor, cancer, malignant or neoplastic volume, size, cell mass; results in inhibiting or preventing progression or an increase in metastatic or non-metastatic tumor, cancer, malignant or neoplastic volume, mass, size or cell numbers; results in inhibiting or decreasing the spread or dissemination of hyperproliferating cells (e.g., metastasis) to other (secondary) sites, regions, tissues or organs in a subject, or establishment of hyperproliferating cells (e.g., metastasis) at other (secondary) sites, regions, tissues or organs in a subject; or results in prolonging lifespan of the subject. In additional particular embodiments, a method of treatment results in reducing or decreasing severity, duration or frequency of an adverse symptom or complication associated with or caused by the metastatic or non-metastatic tumor, cancer, malignancy or neoplasia.

An amount sufficient or an amount effective can but need not be provided in a single administration and, can but need not be, administered alone or in combination with another composition (e.g., chemotherapeutic or immune enhancing or stimulating agent), treatment, protocol or therapeutic regimen. For example, the amount may be proportionally increased as indicated by the need of the subject, status of the disorder, disease or condition treated or the side effects of treatment. In addition, an amount sufficient or an amount effective need not be sufficient or effective if given in single or multiple doses without a second composition (e.g., chemotherapeutic or immune stimulating agent), treatment, protocol or therapeutic regimen, since additional doses, amounts or duration above and beyond such doses, or additional compositions (e.g., chemotherapeutic or immune stimulating agents), treatments, protocols or therapeutic regimens may be included in order to be considered effective or sufficient in a given subject. Amounts considered sufficient also include amounts that result in a reduction of the use of another treatment, therapeutic regimen or protocol.

An amount sufficient or an amount effective need not be effective in each and every subject treated, prophylactically or therapeutically, nor a majority of treated subjects in a given group or population. As is typical for treatment or therapeutic methods, some subjects will exhibit greater or less response to a given treatment, therapeutic regimen or protocol. An amount sufficient or an amount effective refers to sufficiency or effectiveness in a particular subject, not a group or the general population. Such amounts will depend in part upon the condition treated, such as the type or stage of undesirable or aberrant cell proliferation or hyperproliferative disorder (e.g., a metastatic or non-metastatic tumor, cancer, malignancy or neoplasia), the therapeutic effect desired, as well as the individual subject (e.g., the bioavailability within the subject, gender, age, etc.).

Particular non-limiting examples of therapeutic benefit or improvement for undesirable or aberrant cell proliferation, such as a hyperproliferative disorder (e.g., a metastatic or non-metastatic tumor, cancer, malignancy or neoplasia) include a reduction in cell size, mass or volume, inhibiting an increase in cell size, mass or volume, a slowing or inhibition of worsening or progression, stimulating cell necrosis, lysis or apoptosis, reducing or inhibiting neoplastic or tumor malignancy or metastasis, reducing mortality, and prolonging lifespan of a subject. Thus, inhibiting or delaying an increase in cell size, mass, volume or metastasis (stabilization) can increase lifespan (reduce mortality) even if only for a few days, weeks or months, even though complete ablation of the metastatic or non-metastatic tumor, cancer, malignancy or neoplasia has not occurred. Adverse symptoms and complications associated with a hyperproliferative disorder (e.g., a metastatic or non-metastatic tumor, cancer, malignancy or neoplasia) that can be reduced or decreased include, for example, pain, nausea, discomfort, lack of appetite, lethargy and weakness. A reduction in the occurrence, frequency, severity, progression, or duration of a symptom of undesirable or aberrant cell proliferation, such as a hyperproliferative disorder (e.g., a metastatic or non-metastatic tumor, cancer, malignancy or neoplasia), such as an improvement in subjective feeling (e.g., increased energy, appetite, reduced nausea, improved mobility or psychological well being, etc.), are therefore all examples of therapeutic benefit or improvement.

For example, a sufficient or effective amount of a conjugate is considered as having a therapeutic effect if administration results in less chemotherapeutic drug, radiation or immunotherapy being required for treatment of undesirable or aberrant cell proliferation, such as a hyperproliferative disorder (e.g., a metastatic or non-metastatic tumor, cancer, malignancy or neoplasia).

The term "subject" refers to animals, typically mammalian animals, such as humans, non human primates (apes, gibbons, chimpanzees, orangutans, macaques), domestic animals (dogs and cats), farm animals (horses, cows, goats, sheep, pigs) and experimental animal (mouse, rat, rabbit, guinea pig). Subjects include animal disease models, for example, animal models of undesirable or aberrant cell proliferation, such as a hyperproliferative disorder (e.g., a metastatic or non-metastatic tumor, cancer, malignancy or neoplasia) for analysis of conjugates in vivo.

Subjects appropriate for treatment include those having or at risk of having a metastatic or non-metastatic tumor, cancer, malignant or neoplastic cell, those undergoing as well as those who are undergoing or have undergone antiproliferative (e.g., metastatic or non-metastatic tumor, cancer, malignancy or neoplasia) therapy, including subjects where the tumor is in remission. "At risk" subjects typically have risk factors associated with undesirable or aberrant cell proliferation, development of hyperplasia (e.g., a tumor).

Particular examples of at risk or candidate subjects include those with cells that express Her2/neu to which a conjugate can bind, particularly where cells targeted for necrosis, lysis, killing or destruction express greater numbers or amounts of Her2/neu than non-target cells. Such cells can be selectively or preferentially targeted for necrosis, lysis or killing At risk subjects also include those that are candidates for and those that have undergone surgical resection, chemotherapy, immunotherapy, ionizing or chemical radiotherapy, local or regional thermal (hyperthermia) therapy, or vaccination. The invention is therefore applicable to treating a subject who is at risk of a metastatic or non-metastatic tumor, cancer, malignancy or neoplasia or a complication associated with a metastatic or non-metastatic tumor, cancer, malignancy or neoplasia, for example, due to metastatic or non-metastatic tumor, cancer, malignancy or neoplasia reappearance or regrowth following a period of stability or remission.

Risk factors include gender, lifestyle (diet, smoking), occupation (medical and clinical personnel, agricultural and livestock workers), environmental factors (carcinogen exposure), family history (autoimmune disorders, diabetes, etc.), genetic predisposition, etc. For example, subjects at risk for developing melanoma include excess sun exposure (ultraviolet radiation), fair skin, high numbers of naevi (dysplastic nevus), patient phenotype, family history, or a history of a previous melanoma. Subjects at risk for developing cancer can therefore be identified by lifestyle, occupation, environmental factors, family history, and genetic screens for tumor associated genes, gene deletions or gene mutations. Subjects at risk for developing breast cancer lack Brca1, for example. Subjects at risk for developing colon cancer have early age or high frequency polyp formation, or deleted or mutated tumor suppressor genes, such as adenomatous polyposis *coli* (APC), for example.

Subjects also include those precluded from other treatments. For example, certain subjects may not be good candidates for surgical resection, chemotherapy, immunotherapy, ionizing or chemical radiotherapy, local or regional thermal (hyperthermia) therapy, or vaccination. Thus, candidate subjects for treatment in accordance with the invention include those that are not a candidate for surgical resection, chemotherapy, immunotherapy, ionizing or chemical radiotherapy, local or regional thermal (hyperthermia) therapy, or vaccination.

Conjugates may be formulated in a unit dose or unit dosage form. In a particular embodiment, a conjugate is in an amount effective to treat a subject having undesirable or aberrant cell proliferation or a hyperproliferative disorder. In an additional particular embodiment, a conjugate is in an amount effective to treat a subject having a metastatic or non-metastatic tumor, cancer, malignancy or neoplasia. Exemplary unit doses range from about 25-250, 250-500, 500-1000, 1000-2500 or 2500-5000, 5000-25,000, 5000-50, 000 ng; and from about 25-250, 250-500, 500-1000, 1000-2500 or 2500-5000, 5000-25,000, 5000-50,000 µg.

Compositions and methods of the invention may be contacted or provided in vitro, ex vivo or in vivo. Compositions can be administered to provide the intended effect as a single or multiple dosages, for example, in an effective or sufficient amount. Exemplary doses range from about 25-250, 250-500, 500-1000, 1000-2500 or 2500-5000, 5000-25,000, 5000-50,000 pg/kg; from about 50-500, 500-5000, 5000-25,000 or 25,000-50,000 ng/kg; and from about 25-250, 250-500, 500-1000, 1000-2500 or 2500-5000, 5000-25,000, 5000-50,000 µg/kg, on consecutive days, or alternating days or intermittently. Single or multiple doses can be administered on consecutive days, alternating days or intermittently.

Compositions can be administered and methods may be practiced via systemic, regional or local administration, by any route. For example, a conjugate can be administered systemically, regionally or locally, intravenously, orally (e.g., ingestion or inhalation), intramuscularly, intraperitoneally, intradermally, subcutaneously, intracavity, intracranially, transdermally (topical), parenterally, e.g. transmucosally or rectally. Compositions and methods of the invention including pharmaceutical formulations can be administered via a (micro)encapsulated delivery system or packaged into an implant for administration.

The invention further provides conjugates and methods wherein the conjugates are included in pharmaceutical compositions. A pharmaceutical composition refers to "pharmaceutically acceptable" and "physiologically acceptable" carriers, diluents or excipients. As used herein, the term "pharmaceutically acceptable" and "physiologically acceptable," when referring to carriers, diluents or excipients includes solvents (aqueous or non-aqueous), detergents, solutions, emulsions, dispersion media, coatings, isotonic and absorption promoting or delaying agents, compatible with pharmaceutical administration and with the other components of the formulation. Such formulations can be contained in a tablet (coated or uncoated), capsule (hard or soft), microbead, emulsion, powder, granule, crystal, suspension, syrup or elixir.

Pharmaceutical compositions can be formulated to be compatible with a particular route of administration. Compositions for parenteral, intradermal, or subcutaneous administration can include a sterile diluent, such as water, saline solution, fixed oils, polyethylene glycols, glycerine, propylene glycol or other synthetic solvents. The preparation may contain one or more preservatives to prevent microorganism growth (e.g., antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose).

Pharmaceutical compositions for injection include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). The carrier can be a solvent or dispersion medium containing, for example, water, ethanol, polyol (e.g., glycerol, propylene glycol, and polyetheylene glycol), and suitable mixtures thereof. Fluidity can be maintained, for example, by the use of a coating such as lecithin, or by the use of surfactants. Antibacterial and antifungal agents include, for example, parabens, chlorobutanol, phenol, ascorbic acid and thimerosal. Including an agent that delays absorption, for example, aluminum monostearate and gelatin can prolonged absorption of injectable compositions.

Additional pharmaceutical formulations and delivery systems are known to the skilled artisan and are applicable in the methods of the invention (see, e.g., *Remington's Pharmaceutical Sciences* (1990) 18th ed., Mack Publishing Co., Easton, Pa.; *The Merck Index* (1996) 12th ed., Merck Publishing Group, Whitehouse, N.J.; *Pharmaceutical Principles of Solid Dosage Forms*, Technonic Publishing Co., Inc., Lancaster, Pa., (1993); and Poznansky, et al., *Drug Delivery Systems*, R. L. Juliano, ed., Oxford, N.Y. (1980), pp. 253-315).

The invention provides kits including conjugates of the invention, combination compositions and pharmaceutical formulations thereof, packaged into suitable packaging material. A kit optionally includes a label or packaging insert including a description of the components or instructions for use in vitro, in vivo, or ex vivo, of the components therein. Exemplary instructions include instructions for reducing or inhibiting proliferation of a cell, reducing or inhibiting proliferation of undesirable or aberrant cells, such as a hyperproliferating cell, reducing or inhibiting proliferation of a metastatic or non-metastatic tumor, cancer, malignant or neoplastic cell, treating a subject having a hyperproliferative disorder, treating a subject having a metastatic or non-metastatic tumor, cancer, malignancy or neoplasia, or reducing fertility of an animal.

A kit can contain a collection of such components, e.g., two or more conjugates alone, or in combination with another therapeutically useful composition (e.g., an anti-proliferative or immune-enhancing drug).

The term "packaging material" refers to a physical structure housing the components of the kit. The packaging material can maintain the components sterilely, and can be made of material commonly used for such purposes (e.g., paper, corrugated fiber, glass, plastic, foil, ampules, vials, tubes, etc.).

Kits of the invention can include labels or inserts. Labels or inserts include "printed matter," e.g., paper or cardboard, or separate or affixed to a component, a kit or packing material (e.g., a box), or attached to an ampule, tube or vial containing a kit component. Labels or inserts can additionally include a computer readable medium, such as a disk (e.g., floppy diskette, hard disk, ZIP disk), optical disk such as CD- or DVD-ROM/RAM, DVD, MP3, magnetic tape, or an electrical storage media such as RAM and ROM or hybrids of these such as magnetic/optical storage media, FLASH media or memory type cards.

Labels or inserts can include identifying information of one or more components therein, dose amounts, clinical pharmacology of the active ingredient(s) including mechanism of action, pharmacokinetics and pharmacodynamics. Labels or inserts can include information identifying manufacturer information, lot numbers, manufacturer location and date.

Labels or inserts can include information on a condition, disorder, disease or symptom for which a kit component may be used. Labels or inserts can include instructions for the clinician or for a subject for using one or more of the kit components in a method, treatment protocol or therapeutic regimen. Instructions can include dosage amounts, frequency or duration, and instructions for practicing any of the methods, treatment protocols or therapeutic regimes set forth herein. Exemplary instructions include, instructions for treating an undesirable or aberrant cell proliferation, hyperproliferating cells and disorders (e.g., metastatic or non-metastatic tumor, cancer, malignancy or neoplasia). Kits of the invention therefore can additionally include labels or instructions for practicing any of the methods of the invention described herein including treatment methods.

Labels or inserts can include information on any benefit that a component may provide, such as a prophylactic or therapeutic benefit. Labels or inserts can include information on potential adverse side effects, such as warnings to the subject or clinician regarding situations where it would not be appropriate to use a particular composition. Adverse side effects could also occur when the subject has, will be or is currently taking one or more other medications that may be incompatible with the composition, or the subject has, will be or is currently undergoing another treatment protocol or therapeutic regimen which would be incompatible with the composition and, therefore, instructions could include information regarding such incompatibilities.

Invention kits can additionally include other components. Each component of the kit can be enclosed within an individual container and all of the various containers can be within a single package. Invention kits can be designed for cold storage. Invention kits can further be designed to contain host cells expressing conjugates of the invention, or that contain nucleic acids encoding conjugates. The cells in the kit can be maintained under appropriate storage conditions until the cells are ready to be used. For example, a kit including one or more cells can contain appropriate cell storage medium so that the cells can be thawed and grown.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

All applications, publications, patents and other references, GenBank citations and ATCC citations cited herein are incorporated by reference in their entirety. In case of conflict, the specification, including definitions, will control.

As used herein, the singular forms "a", "and," and "the" include plural referents unless the context clearly indicates otherwise. Thus, for example, reference to "a conjugate" or a "ligand that binds to Her2/neu," or a "lytic domain" includes a plurality of such conjugates, ligands, or lytic domains, and so forth.

As used herein, numerical values are often presented in a range format throughout this document. The use of a range format is merely for convenience and brevity and should not be construed as an inflexible limitation on the scope of the invention unless the context clearly indicates otherwise. Accordingly, the use of a range expressly includes all possible subranges, all individual numerical values within that range, and all numerical values or numerical ranges including integers within such ranges and fractions of the values or the integers within ranges unless the context clearly indicates otherwise. This construction applies regardless of the breadth of the range and in all contexts throughout this patent document. Thus, for example, reference to a range of 90-100% includes 91-99%, 92-98%, 93-95%, 91-98%, 91-97%, 91-96%, 91-95%, 91-94%, 91-93%, and so forth. Reference to a range of 90-100% also includes 91%, 92%, 93%, 94%, 95%, 95%, 97%, etc., as well as 91.1%, 91.2%, 91.3%, 91.4%, 91.5%, etc., 92.1%, 92.2%, 92.3%, 92.4%, 92.5%, etc., and so forth.

In addition, reference to a range of 1-5,000 fold includes 1, 2, 3, 4, 5, 6, 7, 8, 9, 10, 11, 12, 13, 14, 15, 16, 17, 18, 19, 20, fold, etc., as well as 1.1, 1.2, 1.3, 1.4, 1.5, fold, etc., 2.1, 2.2, 2.3, 2.4, 2.5, fold, etc., and any numerical range within such a ranges, such as 1-2, 5-10, 10-50, 50-100, 100-500, 100-1000, 500-1000, 1000-2000, 1000-5000, etc. In a further example, reference to a range of KD $10^{-5}$ M to about KD $10^{-13}$ M includes any numerical value or range within or encompassing such values.

As also used herein a series of ranges are disclosed throughout this document. The use of a series of ranges include combinations of the upper and lower ranges to provide another range. This construction applies regardless of the breadth of the range and in all contexts throughout this patent document. Thus, for example, reference to a series of ranges such as 5-10, 10-20, 20-30, 30-40, 40-50, 50-75, 75-100, 100-150, and 150-171, includes ranges such as 5-20, 5-30, 5-40, 5-50, 5-75, 5-100, 5-150, 5-171, and 10-30, 10-40, 10-50, 10-75, 10-100, 10-150, 10-171, and 20-40, 20-50, 20-75, 20-100, 20-150, 20-171, and so forth.

The invention is generally disclosed herein using affirmative language to describe the numerous embodiments. The invention also specifically includes embodiments in which particular subject matter is excluded, in full or in part, such as substances or materials, method steps and conditions, protocols, procedures, assays or analysis. Thus, even though the invention is generally not expressed herein in terms of what the invention does not include aspects that are not expressly included in the invention are nevertheless disclosed herein.

A number of embodiments of the invention have been described. Nevertheless, it will be understood that various modifications may be made without departing from the spirit and scope of the invention. Accordingly, the following examples are intended to illustrate but not limit the scope of invention described in the claims.

The Sequence Listing submitted herewith in computer readable form is incorporated herein by reference.

EXAMPLES

Example 1

To determine, in in vitro studies, cytotoxicity of recombinantly produced antibody (as a antibody) scFv-$C_H3$ to Her-2 receptor conjugated to the lytic peptide, Phor-18 (KFAKFAK KFAKFAK KFAK (SEQ. ID NO. 67)) or (KLAKLAK)$_2$KLAK (SEQ. ID NO. 68). Various linkers (GS and NRVRRS (SEQ. ID NO. 57)) and 1 or 2 molecules of lytic peptides per antibody molecule were studied.

Peptides studied were: Phor18-scFv-$C_H3$-Phor-18 (2 molecules of Phor-18 joined at N- and C-terminal ends of the antibody, scFv-$C_H3$-GS-Phor-18 (one molecule of Phor-18 joined to the antibody at the C-terminus by GS linker, scFv-$C_H3$-GS-(KLAKLAK)$_2$KLAK (SEQ. ID NO. 66) (one molecule of (KLAKLAK)$_2$KLAK (SEQ. ID NO. 68) linked to the antibody at the C-terminus by GS linker, scFv-$C_H3$-NRVRRS (SEQ. ID NO. 57)-Phor-18 (one molecule of Phor-18 to the antibody at the C-terminus by NRVRRS (SEQ. ID NO. 57) linker, and scFv-$C_H3$-NRVRRS-(KLAKLAK)$_2$KLAK (SEQ. ID NO. 69) (one molecule of (KLAKLAK)$_2$KLAK (SEQ. ID NO. 68) to the antibody at the C-terminus by NRVRRS (SEQ. ID NO. 57) linker). Cytotoxicity was compared to a naked antibody (antibody without a lytic peptide) in Her-2 receptor positive cells (SKBR-3 and SKOV-3, human breast and ovarian cancer cells, respectively) and Her-2 receptor negative breast cancer cells (MDA-MB-231).

Example 2

This example describes various materials and methods used in the studies described herein.

Materials:

Recombinant DNA technique was used to synthesize anti-Her2 antibody as a recombinant antibody in *Escherichia coli*. The scFv-$C_H3$ antibody (Olafsen T. et al *Protein Engineering, Design & Selection* 17, 315-323, 2004) was conjugated via a peptide linker or without a linker as described in Table 1 to either Phor-18 or an amphipathic, alpha-helical lytic peptide, (KLAKLAK) (SEQ ID NO. 68) and analyzed for cytotoxicity in vitro. The plasmid was acquired through gene codon optimization. The gene was synthesized with a N-His tag sequence and the plasmid was subcloned into an *E. coli* bacteria expression vector pUC57. After expression optimization and evaluation the His-tag product was selected and 1 L of the bacteria expression product was purified in a one-step affinity purification. The sequences of the plasmid gene insertion for each construct is described in Table 1.

TABLE 1

Nucleotide sequence of the plasmid insertion for the production of each recombinant Her2/neu antibody and antibody conjugate.

1. Her2/neu scFv-$C_H3$ (SEQ ID NO: 58):

```
   1 CATATGCATC ACCACCACCA CCACGACGAC GACGACAAAG ATATTCAAAT GACCCAGTCC
  61 CCGAGCAGCC TGAGTGCCTC CGTTGGCGAC CGCGTGACCA TTACGTGCCG TGCGAGCCAG
 121 GATGTCAACA CCGCGGTGGC CTGGTATCAG CAAAAACCGG GCAAAGCGCC GAAACTGCTG
 181 ATCTATTCAG CCTCGTTTCT GTACAGCGGT GTTCCGTCTC GTTTCAGCGG CTCTCGCAGT
 241 GGTACCGATT TTACCCTGAC GATTAGCTCT CTGCAGCCGG AAGACTTTGC GACGTATTAC
 301 TGCCAGCAAC ATTACACCAC GCCGCCGACC TTCGGCCAGG GTACGAAAGT GGAAATCAAA
 361 GGTTCCACCT CAGGCGGTGG CAGTGGTGGC GGTTCCGGCG GTGGCGGTAG TTCCGAAGTT
 421 CAGCTGGTCG AAAGTGGCGG TGGCCTGGTT CAACCGGGTG GCTCACTGCG TCTGTCGTGT
 481 GCAGCAAGCG GTTTCAACAT CAAAGATACC TACATCCACT GGGTTCGTCA GGCGCCGGGC
 541 AAAGGTCTGG AATGGGTCGC CCGCATTTAC CCGACCAATG GCTATACGCG TTACGCAGAT
 601 AGCGTGAAAG GTCGCTTTAC CATCTCTGCG GACACCAGTA AAAACACGGC CTATCTGCAG
 661 ATGAATAGCC TGCGTGCGGA AGATACGGCC GTTTATTACT GCTCTCGCTG GGGTGGCGAT
 721 GGCTTCTATG CTATGGACTA CTGGGGCCAG GGTACCCTGG TGACGGTTTC ATCGGGTCAG
 781 CCGCGTGAAC CGCAAGTGTA TACCCTGCCG CCGTCACGCG ATGAACTGAC GAAAAACCAG
 841 GTGTCGCTGA CGTGTCTGGT TAAAGGCTTT TACCCGAGCG ACATCGCGGT TGAATGGGAA
 901 TCTAATGGTC AACCGGAAAA CAATTATAAA ACCACGCCGC CGGTCCTGGA TAGTGACGGC
 961 TCCTTTTTCC TGTACAGTAA ACTGACCGTG GATAAATCCC GTTGGCAGCA GGGTAACGTC
1021 TTCTCGTGTA GCGTGATGCA TGAAGCCCTG CATAATCACT ATACCCAGAA ATCTCTGAGT
1081 CTGTCCCCGG GCAAAGGTTC AACGTCGGGT GGCGGTTCCG GCGGTGGCTC AGGTGGCGGT
1141 GGCAGCTCTG GCCAACCGCG CGAACCGCAG GTTTACACCC TGCCGCCGAG CCGTGACGAA
1201 CTGACCAAAA ACCAAGTCAG CCTGACGTGC CTGGTGAAAG GCTTTTACCC GAGTGACATT
1261 GCAGTTGAAT GGGAATCCAA TGGTCAGCCG GAAAATAACT ACAAAACGAC GCCGCCGGTT
1321 CTGGATTCAG ACGGCTCGTT TTTCCTGTAC TCAAAACTGA CCGTCGATAA ATCGCGCTGG
1381 CAACAGGGTA ACGTTTTCAG CTGCTCTGTC ATGCACGAAG CCCTGCACAA CCATTATACC
1441 CAGAAAAGTC TGTCCCTGTC ACCGGGCAAA GAAGTGCAGC TGGTTGAATC TGGTGGCGGT
1501 CTGGTGCAAC CGGGCGGTTC GCTGCGTCTG AGCTGTGCAG CTTGTGGCTT TAATATTAAA
1561 GACACGTACA TCCACTGGGT GCGTCAGGCA CCGGGTAAAG GCCTGGAATG GGTTGCTCGT
1621 ATCTATCCGA CGAACGGTTA TACGCGTTAC GCCGATAGCG TCAAAGGCCG TTTTACCATC
```

TABLE 1-continued

Nucleotide sequence of the plasmid insertion for the production of each
recombinant Her2/neu antibody and antibody conjugate.

```
1681 AGTGCAGACA CCTCCAAAAA CACGGCTTAT CTGCAGATGA ATAGTCTGCG TGCAGAAGAT
1741 ACCGCTGTTT ATTACTGCAG CCGCTGGGGC GGTGATGGCT TCTATGCAAT GGATTATTGG
1801 GGTCAAGGTA CCCTGGTCAC CGTGAGTTCC GGTTCGACCA GCGGCGGTGG CTCAGGTGGC
1861 GGTTCGGGCG GTGGCGGTTC ATCGGACATT CAGATGACGC AAAGCCCGAG CTCTCTGTCT
1921 GCGAGTGTTG GCGATCGTGT CACCATCACG TGTCGCGCCT CTCAGGACGT GAATACCGCA
1981 GTTGCTTGGT ACCAACAAAA ACCGGGCAAA GCACCGAAAC TGCTGATTTA CTCCGCTTCA
2041 TTCCTGTACA GCGGTGTGCC GTCTCGTTTT TCGGGCAGCC GCTCTGGTAC CGATTTCACC
2101 CTGACGATTA GTTCCCTGCA ACCGGAAGAT TTCGCCACCT ACTACTGCCA GCAACAGTAT
2161 ACGACCCCGC CGACGTTTGG TCAGGGCACG AAAGTGGAAA TTAAATAATG AAAGCTT
```

2. scFv-C$_H$3-GS-Phor-18 (SEQ ID NO: 59):

```
   1 CATATGCATC ACCACCACCA CCACGACGAC GACGACAAAG ATATTCAAAT GACCCAGTCC
  61 CCGAGCAGCC TGAGTGCCTC CGTTGGCGAC CGCGTGACCA TTACGTGCCG TGCGAGCCAG
 121 GATGTCAACA CCGCGGTGGC CTGGTATCAG CAAAAACCGG GCAAAGCGCC GAAACTGCTG
 181 ATCTATTCAG CCTCGTTTCT GTACAGCGGT GTTCCGTCTC GTTTCAGCGG CTCTCGCAGT
 241 GGTACCGATT TTACCCTGAC GATTAGCTCT CTGCAGCCGG AAGACTTTGC GACGTATTAC
 301 TGCCAGCAAC ATTACACCAC GCCGCCGACC TTCGGCCAGG GTACGAAAGT GGAAATCAAA
 361 GGTTCCACCT CAGGCGGTGG CAGTGGTGGC GGTTCCGGCG GTGGCGGTAG TTCCGAAGTT
 421 CAGCTGGTCG AAAGTGGCGG TGGCCTGGTT CAACCGGGTG GCTCACTGCG TCTGTCGTGT
 481 GCAGCAAGCG GTTTCAACAT CAAAGATACC TACATCCACT GGGTTCGTCA GGCGCCGGGC
 541 AAAGGTCTGG AATGGGTGCC CCGCATTTAC CCGACCAATG GCTATACGCG TTACGCAGAT
 601 AGCGTGAAAG GTCGCTTTAC CATCTCTGCG GACACCAGTA AAAACACGGC CTATCTGCAG
 661 ATGAATAGCC TGCGTGCGGA AGATACGGCC GTTTATTACT GCTCTCGCTG GGGTGGCGAT
 721 GGCTTCTATG CTATGGACTA CTGGGGCCAG GGTACCCTGG TGACGGTTTC ATCGGGTCAG
 781 CCGCGTGAAC CGCAAGTGTA TACCCTGCCG CCGTCACGCG ATGAACTGAC GAAAAACCAG
 841 GTGTCGCTGA CGTGTCTGGT TAAAGGCTTT TACCCGAGCG ACATCGCGGT TGAATGGGAA
 901 TCTAATGGTC AACCGGAAAA CAATTATAAA ACCACGCCGC CGGTCCTGGA TAGTGACGGC
 961 TCCTTTTTCC TGTACAGTAA ACTGACCGTG GATAAATCCC GTTGGCAGCA GGGTAACGTC
1021 TTCTCGTGTA GCGTGATGCA TGAAGCCCTG CATAATCCAT ATACCCAGAA ATCTCTGAGT
1081 CTGTCCCCGG GCAAAGGTTC AACGTCGGGT GGCGGTTCCG GCGGTGGCTC AGGTGGCGGT
1141 GGCAGCTCTG GCCAACCGCG CGAACCGCAG GTTTACACCC TGCCGCCGAG CCGTGACGAA
1201 CTGACCAAAA ACCAAGTCAG CCTGACGTGC CTGGTGAAAG CTTTTTACCC GAGTGACATT
1261 GCAGTTGAAT GGGAATCCAA TGGTCAGCCG GAAAATAACT ACAAAACGAC GCCGCCGGTT
1321 CTGGATTCAG ACGGCTCGTT TTTCCTGTAC TCAAAACTGA CCGTCGATAA ATCGCGCTGG
1381 CAACAGGGTA ACGTTTTCAG CTGCTCTGTC ATGCACGAAG CCCTGCACAA CCATTATACC
1441 CAGAAAAGTC TGTCCCTGTC ACCGGGCAAA GAAGTGCAGC TGGTTAATC TGGTGGCGGT
1501 CTGGTGCAAC CGGGCGGTTC GCTGCGTCTG AGCTGTGCAG CTTCTGGCTT TAATATTAAA
1561 GACACGTACA TCCACTGGGT GCGTCAGGCA CCGGGTAAAG GCCTGGAATG GGTTGCTCGT
1621 ATCTATCCGA CGAACGGTTA TACGCGTTAC GCCGATAGCC TCAAAGGCCG TTTTACCATC
1681 AGTGCAGACA CCTCCAAAAA CACGGCTTAT CTGCAGATGA ATAGTCTGCG TGCAGAAGAT
1741 ACCGCTGTTT ATTACTGCAG CCGCTGGGGC GGTGATGGCT TCTATGCAAT GGATTATTGG
1801 GGTCAAGGTA CCCTGGTCAC CGTGAGTTCC GGTTCGACCA GCGGCGGTGG CTCAGGTGGC
1861 GGTTCGGGCG GTGGCGGTTC ATCGGACATT CAGATGACGC AAAGCCCGAG CTCTCTGTCT
1921 GCGAGTGTTG GCGATCGTGT CACCATCACG TGTCGCGCCT CTCAGGACGT GAATACCGCA
1981 GTTGCTTGGT ACCAACAAAA ACCGGGCAAA GCACCGAAAC TGCTGATTTA CTCCGCTTCA
2041 TTCCTGTACA GCGGTGTGCC GTCTCGTTTT TCGGGCAGCC GCTCTGGTAC CGATTTCACC
2101 CTGACGATTA GTTCCCTGCA ACCGGAAGAT TTCGCCACCT ACTACTGCCA GCAACACTAT
2161 ACGACCCCGC CGACGTTTGG TCAGGGCACG AAAGTGGAAA TTAAAGGCAG CAAATTTGCG
2221 AAATTCGCCA AAAAATTCGC AAAATTCGCG AAAAAATTCG CGAAATAATG AAAGCTT
```

3. scFv-C$_H$3-GS-(KLAKLAK)$_2$KLAK (SEQ ID NO: 60):

```
   1 CATATGGAAA ATCTGTATTT CCAAGGTGAT ATTCAAATGA CCCAGTCCCC GAGCAGCCTG
  61 AGTGCCTCCG TTGGCGACCG CGTGACCATT ACGTGCCGTG CGAGCCAGGA TGTCAACACC
 121 GCGGTGGCCT GGTATCAGCA AAAACCGGGC AAAGCGCCGA AACTGCTGAT CTATTCAGCC
 181 TCGTTTCTGT ACAGCGGTGT TCCGTCTCGT TTCAGCGGCT CTCGCAGTGG TACCGATTTT
 241 ACCCTGACGA TTAGCTCTCT GCAGCCGGAA GACTTTGCGA CGTATTACTG CCAGCAACAT
 301 TACACCACGC CGCCGACCTT CGGCCAGGGT ACGAAAGTGG AAATCAAAGG TTCCACCTCA
 361 GGCGGTGGCA GTGGTGGCGG TTCCGGCGGT GGCGGTAGTT CCGAAGTTCA GCTGGTCGAA
 421 AGTGGCGGTG GCCTGGTTCA ACCGGGTGGC TCACTGCGTC TGTCGTGTGC AGCAAGCGGT
 481 TTCAACATCA AAGATACCTA CATCCACTGG GTTCGTCAGG CGCCGGGCAA AGGTCTGGAA
 541 TGGGTCGCCC GCATTTACCC GACCAATGGC TATACGCGTT ACGCAGATAG CGTGAAAGGT
 601 CGCTTTACCA TCTCTGCGGA CACCAGTAAA AACACGGCCT ATCTGCAGAT GAATAGCCTG
 661 CGTGCGGAAG ATACGGCCGT TTATTACTGC TCTCGCTGGG GTGGCGATGG CTTCTATGCT
 721 ATGGACTACT GGGGCCAGGG TACCCTGGTG ACGGTTTCAT CGGGTCAGCC GCGTGAACCG
 781 CAAGTGTATA CCCTGCCGCC GTCACGCGAT GAACTGACGA AAACCAGGT GTCGCTGACG
 841 TGTCTGGTTA AAGGCTTTTA CCCGAGCGAC ATCGCGGTTG AATGGGAATC TAATGGTCAA
 901 CCGGAAAACA ATTATAAAAC CACGCCGCCG GTCCTGGATA GTGACGGCTC CTTTTTCCTG
 961 TACAGTAAAC TGACCGTGGA TAAATCCCGT TGGCAGCAGG GTAACGTCTT CTCGTGTAGC
1021 GTGATGCATG AAGCCCTGCA TAATCACTAT ACCCAGAAAT CTCTGAGTCT GTCCCCGGGC
1081 AAAGGTTCAA CGTCGGGTGG CGGTTCCGGC GGTGGCTCAG GTGGCGGTGG CAGCTCTGGC
1141 CAACCGCGCG AACCGCAGGT TTACACCCTG CCGCCGAGCC GTGACGAACT GACCAAAAAC
1201 CAAGTCAGCC TGACGTGCCT GGTGAAAGCT TTTACCCGA GTGACATTGC AGTTGAATGG
1261 GAATCCAATG GTCAGCCGGA AAATAACTAC AAAACGACGC CGCCGGTTCT GGATTCAGAC
1321 GGCTCGTTTT TCCTGTACTC AAAACTGACC GTCGATAAAT CGCGCTGGCA ACAGGGTAAC
1381 GTTTTCAGCT GCTCTGTCAT GCACGAAGCC CTGCACAACC ATTATACCCA GAAAAGTCTG
```

TABLE 1-continued

Nucleotide sequence of the plasmid insertion for the production of each recombinant Her2/neu antibody and antibody conjugate.

```
1441 TCCCTGTCAC CGGGCAAAGA AGTGCAGCTG GTTGAATCTG GTGGCGGTCT GGTGCAACCG
1501 GGCGGTTCGC TGCGTCTGAG CTGTGCAGCT TCTGGCTTTA ATATTAAAGA CACGTACATC
1561 CACTGGGTGC GTCAGGCACC GGGTAAAGGC CTGGAATGGG TTGCTCGTAT CTATCCGACG
1621 AACGGTTATA CGCGTTACGC CGATAGCGTC AAAGGCCGTT TTACCATCAG TGCAGACACC
1681 TCCAAAAACA CGGCTTATCT GCAGATGAAT AGTCTGCGTG CAGAAGATAC CGCTGTTTAT
1741 TACTGCAGCC GCTGGGGCGG TGATGGCTTC TATGCAATGG ATTATTGGGG TCAAGGTACC
1801 CTGGTCACCG TGAGTTCCGG TTCGACCAGC GGCGGTGGCT CAGGTGGCGG TTCGGGCGGT
1861 GGCGGTTCAT CGGACATTCA GATGACGCAA AGCCCGAGCT CTCTGTCTGC GAGTGTTGGC
1921 GATCGTGTCA CCATCACGTG TCGCGCCTCT CAGGACGTGA ATACCGCAGT TGCTTGGTAC
1981 CAACAAAAAC CGGGCAAAGC ACCGAAACTG CTGATTTACT CCGCTTCATT CCTGTACAGC
2041 GGTGTGCCGT CTCGTTTTTC GGGCAGCCGC TCTGGTACCG ATTTCACCCT GACGATTAGT
2101 TCCCTGCAAC CGGAAGATTT CGCCACCTAC TACTGCCAGC AACACTATAC GACCCCGCCG
2161 ACGTTTGGTC AGGGCACGAA AGTGGAAATT AAAGGCAGCA AACTGGCGAA ACTGGCCAAA
2221 AAACTGGCAA AACTGGCGAA AAAACTGGCG AAATAATGAA AGCTT
```

4. scFv-C$_H$3-NRVRRS-Phor-18 (SEQ ID NO: 61):

```
   1 CATATGGAAA ATCTGTATTT CCAAGGTGAT ATTCAAATGA CCCAGTCCCC GAGCAGCCTG
  61 AGTGCCTCCG TTGGCGACCG CGTGACCATT ACGTGCCGTG CGAGCCAGGA TGTCAACACC
 121 GCGGTGGCCT GGTATCAGCA AAAACCGGGC AAAGCGCCGA AACTGCTGAT CTATTCAGCC
 181 TCGTTTCTGT ACAGCGGTGT TCCGTCTCGT TTCAGCGGCT CTCGCAGTGG TACCGATTTT
 241 ACCCTGACGA TTAGCTCTCT GCAGCCGGAA GACTTTGCGA CGTATTACTG CCAGCAACAT
 301 TACACCACGC CGCCGACCTT CGGCCAGGGT ACGAAAGTGG AAATCAAAGG TTCCACCTCA
 361 GGCGGTGGCA GTGGTGGCGG TTCCGGCGGT GGCGGTAGTT CCGAAGTTCA GCTGGTCGAA
 421 AGTGGCGGTG GCCTGGTTCA ACCGGGTGGC TCACTGCGTC TGTCGTGTGC AGCAAGCGGT
 481 TTCAACATCA AAGATACCTA CATCCACTGG GTTCGTCAGG CGCCGGGCAA AGGTCTGGAA
 541 TGGGTCGCCC GCATTTACCC GACCAATGGC TATACGCGTT ACGCAGATAG CGTGAAAGGT
 601 CGCTTTACCA TCTCTGCGGA CACCAGTAAA AACACGGCCT ATCTGCAGAT GAATAGCCTG
 661 CGTGCGGAAG ATACGGCCGT TTATTACTGC TCTCGCTGGG GTGGCGATGG CTTCTATGCT
 721 ATGGACTACT GGGGCCAGGG TACCCTGGTG ACGGTTTCAT CGGGTCAGCC GCGTGAACCG
 781 CAAGTGTATA CCCTGCCGCC GTCACGCGAT GAACTGACGA AAAACCAGGT GTCGCTGACG
 841 TGTCTGGTTA AAGGCTTTTA CCCGAGCGAC ATCGCGGTTG AATGGGAATC TAATGGTCAA
 901 CCGGAAAACA ATTATAAAAC CACGCCGCCG GTCCTGGATA GTGACGGCTC CTTTTTCCTG
 961 TACAGTAAAC TGACCGTGGA TAAATCCCGT TGGCAGCAGG GTAACGTCTT CTCGTGTAGC
1021 GTGATGCATG AAGCCCTGCA TAATCACTAT ACCCAGAAAT CTCTGAGTCT GTCCCCGGGC
1081 AAAGGTTCAA CGTCGGGTGG CGGTTCCGGC GGTGGCTCAG GTGGCGGTGG CAGCTCTGGC
1141 CAACCGCGCG AACCGCAGGT TTACACCCTG CCGCCGAGCC GTGACGAACT GACCAAAAAC
1201 CAAGTCAGCC TGACGTGCCT GGTGAAAGGC TTTTACCCGA GTGACATTGC AGTTGAATGG
1261 GAATCCAATG GTCAGCCGGA AAATAACTAC AAAACGACGC CGCCGGTTCT GGATTCAGAC
1321 GGCTCGTTTT TCCTGTACTC AAAACTGACC GTCGATAAAT CGCGCTGGCA ACAGGGTAAC
1381 GTTTTCAGCT GCTCTGTCAT GCACGAAGCC CTGCACAACC ATTATACCCA GAAAAGTCTG
1441 TCCCTGTCAC CGGGCAAAGA AGTGCAGCTG GTTGAATCTG GTGGCGGTCT GGTGCAACCG
1501 GGCGGTTCGC TGCGTCTGAG CTGTGCAGCT TCTGGCTTTA ATATTAAAGA CACGTACATC
1561 CACTGGGTGC GTCAGGCACC GGGTAAAGGC CTGGAATGGG TTGCTCGTAT CTATCCGACG
1621 AACGGTTATA CGCGTTACGC CGATAGCGTC AAAGGCCGTT TTACCATCAG TGCAGACACC
1681 TCCAAAAACA CGGCTTATCT GCAGATGAAT AGTCTGCGTG CAGAAGATAC CGCTGTTTAT
1741 TACTGCAGCC GCTGGGGCGG TGATGGCTTC TATGCAATGG ATTATTGGGG TCAAGGTACC
1801 CTGGTCACCG TGAGTTCCGG TTCGACCAGC GGCGGTGGCT CAGGTGGCGG TTCGGGCGGT
1861 GGCGGTTCAT CGGACATTCA GATGACGCAA AGCCCGAGCT CTCTGTCTGC GAGTGTTGGC
1921 GATCGTGTCA CCATCACGTG TCGCGCCTCT CAGGACGTGA ATACCGCAGT TGCTTGGTAC
1981 CAACAAAAAC CGGGCAAAGC ACCGAAACTG CTGATTTACT CCGCTTCATT CCTGTACAGC
2041 GGTGTGCCGT CTCGTTTTTC GGGCAGCCGC TCTGGTACCG ATTTCACCCT GACGATTAGT
2101 TCCCTGCAAC CGGAAGATTT CGCCACCTAC TACTGCCAGC AACACTATAC GACCCCGCCG
2161 ACGTTTGGTC AGGGCACGAA AGTGGAAATT AAAACCGTG TGCGTCGCAG CAAATTTGCG
2221 AAATTCGCCA AAAATTTGC AAAATTCGCT AAAAAATTTG CGAAATAATG AAAGCTT
```

5. scFv-C$_H$3-NRVRRS-(KLAKLAK)$_2$KLAK (SEQ ID NO: 62):

```
   1 CATATGCATC ACCACCACCA CCACGACGAC GACGACAAAG ATATTCAAAT GACCCAGTCC
  61 CCGAGCAGCC TGAGTGCCTC CGTTGGCGAC CGCGTGACCA TTACGTGCCG TGCGAGCCAG
 121 GATGTCAACA CCGCGGTGGC CTGGTATCAG CAAAAACCGG GCAAAGCGCC GAAACTGCTG
 181 ATCTATTCAG CCTCGTTTCT GTACAGCGGT GTTCCGTCTC GTTTCAGCGG CTCTCGCAGT
 241 GGTACCGATT TTACCCTGAC GATTAGCTCT CTGCAGCCGG AAGACTTTGC GACGTATTAC
 301 TGCCAGCAAC ATTACACCAC GCCGCCGACC TTCGGCCAGG GTACGAAAGT GGAAATCAAA
 361 GGTTCCACCT CAGGCGGTGG CAGTGGTGGC GGTTCCGGCG TGGCGGTAG TTCCGAAGTT
 421 CAGCTGGTCG AAAGTGGCGG TGGCCTGGTT CAACCGGGTG GCTCACTGCG TCTGTCGTGT
 481 GCAGCAAGCG GTTTCAACAT CAAAGATACC TACATCCACT GGGTTCGTCA GGCGCCGGGC
 541 AAAGGTCTGG AATGGGTCGC CCGCATTTAC CCGACCAATG GCTATACGCG TTACGCAGAT
 601 AGCGTGAAAG GTCGCTTTAC CATCTCTGCG GACACCAGTA AAAACACGGC CTATCTGCAG
 661 ATGAATAGCC TGCGTGCGGA AGATACGGCC GTTTATTACT GCTCTCGCTG GGGTGGCGAT
 721 GGCTTCTATG CTATGGACTA CTGGGGCCAG GGTACCCTGG TGACGGTTTC ATCGGGTCAG
 781 CCGCGTGAAC CGCAAGTGTA TACCCTGCCG CCGTCACGCG ATGAACTGAC GAAAAACCAG
 841 GTGTCGCTGA CGTGTCTGGT TAAAGGCTTT TACCCGAGCG ACATCGCGGT TGAATGGGAA
 901 TCTAATGGTC AACCGGAAAA CAATTATAAA ACCACGCCGC CGGTCCTGGA TAGTGACGGC
 961 TCCTTTTTCC TGTACAGTAA ACTGACCGTG GATAAATCCC GTTGGCAGCA GGGTAACGTC
1021 TTCTCGTGTA GCGTGATGCA TGAAGCCCTG CATAATCACT ATACCCAGAA ATCTCTGAGT
1081 CTGTCCCCGG GCAAAGGTTC AACGTCGGGT GGCGGTTCCG GCGGTGGCTC AGGTGGCGGT
```

TABLE 1-continued

Nucleotide sequence of the plasmid insertion for the production of each recombinant Her2/neu antibody and antibody conjugate.

```
1141 GGCAGCTCTG GCCAACCGCG CGAACCGCAG GTTTACACCC TGCCGCCGAG CCGTGACGAA
1201 CTGACCAAAA ACCAAGTCAG CCTGACGTGC CTGGTGAAAG GCTTTTACCC GAGTGACATT
1261 GCAGTTGAAT GGGAATCCAA TGGTCAGCCG GAAAATAACT ACAAAACGAC GCCGCCGGTT
1321 CTGGATTCAG ACGGCTCGTT TTTCCTGTAC TCAAAACTGA CCGTCGATAA ATCGCGCTGG
1381 CAACAGGGTA ACGTTTTCAG CTGCTCTGTC ATGCACGAAG CCCTGCACAA CCATTATACC
1441 CAGAAAAGTC TGTCCCTGTC ACCGGGCAAA GAAGTGCAGC TGGTTGAATC TGGTGGCGGT
1501 CTGGTGCAAC CGGGCGGTTC GCTGCGTCTG AGCTGTGCAG CTTCTGGCTT TAATATTAAA
1561 GACACGTACA TCCACTGGGT GCGTCAGGCA CCGGGTAAAG GCCTGGAATG GGTTGCTCGT
1621 ATCTATCCGA CGAACGGTTA TACGCGTTAC GCCGATAGCG TCAAAGGCCG TTTTACCATC
1681 AGTGCAGACA CCTCCAAAAA CACGGCTTAT CTGCAGATGA ATAGTCTGCG TGCAGAAGAT
1741 ACCGCTGTTT ATTACTGCAG CCGCTGGGGC GGTGATGGCT TCTATGCAAT GGATTATTGG
1801 GGTCAAGGTA CCCTGGTCAC CGTGAGTTCC GGTTCGACCA GCGGCGGTGG CTCAGGTGGC
1861 GGTTCGGGCG GTGGCGGTTC ATCGGACATT CAGATGACGC AAAGCCCGAG CTCTCTGTCT
1921 GCGAGTGTTG GCGATCGTGT CACCATCACG TGTCGCGCCT CTCAGGACGT GAATACCGCA
1981 GTTGCTTGGT ACCAACAAAA ACCGGGCAAA GCACCGAAAC TGCTGATTTA CTCCGCTTCA
2041 TTCCTGTACA GCGGTGTGCC GTCTCGTTTT TCGGGCAGCC GCTCTGGTAC CGATTTCACC
2101 CTGACGATTA GTTCCCTGCA ACCGGAAGAT TTCGCCACCT ACTACTGCCA GCAACACTAT
2161 ACGACCCCGC CGACGTTTGG TCAGGGCACG AAAGTGGAAA TTAAAACCG TGTGCGTCGC
2221 AGCAAACTGG CGAAACTGGC CAAAAAACTG GCAAAACTGG CTAAAAAACT GTGGAAATAA
2281 TGAAAGCTT
```

6. Phor18-scFv-C<sub>H</sub>3-Phor-18 (SEQ ID NO: 63):

```
   1 CATATGGAAA ATCTGTATTT CCAAGGTAAA TTTGCGAAAT TCGCCAAAAA ATTCGCAAAA
  61 TTCGCGAAAA AATTCGCGAA   GATATTCAA ATGACCCAGT CCCCGAGCAG CCTGAGTGCC
 121 TCCGTTGGCG ACCGCGTGAC CATTACGTGC CGTGCGAGCC AGGATGTCAA CACCGCGGTG
 181 GCCTGGTATC AGCAAAAACC GGGCAAAGCG CCGAAACTGC TGATCTATTC AGCCTCGTTT
 241 CTGTACAGCG GTGTTCCGTC TCGTTTCAGC GGCTCTGCA GTGGTACCGA TTTTACCCTG
 301 ACGATTAGCT CTCTGCAGCC GGAAGACTTT GCGACGTATT ACTGCCAGCA ACATTACACC
 361 ACGCCGCCGA CCTTCGGCCA GGGTACGAAA GTGGAAATCA AAGGTTCCAC CTCAGGCGGT
 421 GGCAGTGGTG GCGGTTCCGG CGGTGGCGGT AGTTCCGAAG TTCAGCTGGT CGAAAGTGGC
 481 GGTGGCCTGG TTCAACCGGG TGGCTCACTG CGTCTGTCGT GTGCAGCAAG CGGTTTCAAC
 541 ATCAAAGATA CCTACATCCA CTGGGTTCGT CAGGCGCCGG GCAAAGGTCT GGAATGGGTC
 601 GCCCGCATTT ACCCGACCAA TGGCTATACG CGTTACGCAG ATAGCGTGAA AGGTCGCTTT
 661 ACCATCTCTG CGGACACCAG TAAAAACACG GCCTATCTGC AGATGAATAG CCTGCGTGCG
 721 GAAGATACGG CCGTTTATTA CTGCTCTCGC TGGGGTGGCG ATGGCTTCTA TGCTATGGAC
 781 TACTGGGGCC AGGGTACCCT GGTGACGGTT TCATCGGGTC AGCCGCGTGA ACCGCAAGTG
 841 TATACCCTGC CGCCGTCACG CGATGAACTG ACGAAAAACC AGGTGTCGCT GACGTGTCTG
 901 GTTAAAGGCT TTTACCCGAG CGACATCGCG GTTGAATGGG AATCTAATGG TCAACCGGAA
 961 AACAATTATA AAACCACGCC GCCGGTCCTG GATAGTGACG GCTCCTTTTT CCTGTACAGT
1021 AAACTGACCG TGGATAAATC CCGTTGGCAG CAGGGTAACG TCTTCTCGTG TAGCGTGATG
1081 CATGAAGCCC TGCATAATCA CTATACCCAG AAATCTCTGA GTCTGTCCCC GGGCAAAGGT
1141 TCAACGTCGG GTGGCGGTTC CGGCGGTGGC TCAGGTGGCG GTGGCAGCTC TGGCCAACCG
1201 CGCGAACCGC AGGTTTACAC CCTGCCGCCG AGCCGTGACG AACTGACCAA AAACCAAGTC
1261 AGCCTGACGT GCCTGGTGAA AGGCTTTTAC CCGAGTGACA TTGCAGTTGA ATGGGAATCC
1321 AATGGTCAGC CGGAAAATAA CTACAAAACG ACGCCGCCGG TTCTGGATTC AGACGGCTCG
1381 TTTTTCCTGT ACTCAAAACT GACCGTCGAT AAATCGCGCT GGCAACAGGG TAACGTTTTC
1441 AGCTGCTCTG TCATGCACGA AGCCCTGCAC AACCATTATA CCCAGAAAAG TCTGTCCCTG
1501 TCACCGGGCA AAGAAGTGCA GCTGGTTGAA TCTGGTGGCG GTCTGGTGCA ACCGGGCGGT
1561 TCGCTGCGTC TGAGCTGTGC AGCTTCTGGC TTTAATATTA AAGACACGTA CATCCACTGG
1621 GTGCGTCAGG CACCGGGTAA AGGCCTGGAA TGGGTTGCTC GTATCTATCC GACGAACGGT
1681 TATACGCGTT ACGCCGATAG CGTCAAAGGC CGTTTTACCA TCAGTGCAGA CACCTCCAAA
1741 AACACGGCTT ATCTGCAGAT GAATAGTCTG CGTGCAGAAG ATACCGCTGT TTATTACTGC
1801 AGCCGCTGGG GCGGTGATGG CTTCTATGCA ATGGATTATT GGGGTCAAGG TACCCTGGTC
1861 ACCGTGAGTT CCGGTTCGAC CAGCGGCGGT GGCTCAGGTG GCGGTTCGGG CGGTGGCGGT
1921 TCATCGGACA TTCAGATGAC GCAAAGCCCG AGCTCTCTGT CTGCGAGTGT TGGCGATCGT
1981 GTCACCATCA CGTGTCGCGC CTCTCAGGAC GTGAATACCG CAGTTGCTTG GTACCAACAA
2041 AAACCGGGCA AAGCACCGAA ACTGCTGATT TACTCCGCTT CATTCCTGTA CAGCGGTGTG
2101 CCGTCTCGTT TTTCGGGCAG CCGCTCTGGT ACCGATTTCA CCCTGACGAT TAGTTCCCTG
2161 CAACCGGAAG ATTTCGCCAC CTACTACTGC CAGCAACACT ATACGACCCC GCCGACGTTT
2221 GGTCAGGGCA CGAAAGTGGA AATTAAAAAA TTTGCGAAAT TCGCCAAAAA ATTCGCAAAA
2281 TTCGCGAAAA AATTCGCGAA ATAATGAAAG CTT
```

Chemical Conjugation of Phor-18 to a Monoclonal Anti-Her2 Antibody IgG1 (MAb):

Purified antibody in phosphate buffered saline (PBS) is concentrated to a concentration of approximately 2 mg/mL. A 20 mM solution of N-succinidyl-3-(2-pyridylothio)propionate (SPDP) is freshly prepared in dimethylsulfoxide (DMSO), and added to the antibody solution in 20-fold excess. The mixture is incubated at room temperature for about 30 minutes to produce the antibody-linker intermediate. Excess unreacted SPDP is removed by size exclusion. The cytotoxic molecule containing cysteine is thoroughly reduced by reaction with a 10-fold excess of reductacryl reagent before mixing in 10-fold excess with the antibody-linker construct. The reaction is allowed to incubate at room temperature for 18 hours, then desalted to remove unreacted cytotoxin molecule. The solution is filter-sterilized before storage.

In Vitro:

In vitro cytotoxicity studies were performed to determine the cytotoxicity of the recombinant antibody preparations (conjugated and unconjugated) and lytic peptide, Phor-18, was used in control incubations. Cells were prepared in 96 well plates using 2,000 cells/well and were allowed to attach for 48 hours. Phor-18 in lyophilized form was freshly dissolved in saline and added into the multi-well plates at antibody-lytic peptide conjugates were due to the presence of lytic peptide payload and sequence of the lytic peptide. Again, as expected, unconjugated Phor-18 showed very minimal non-specific cytotoxicity in all cell lines (Table 2).

TABLE 2

In vitro cytotoxicity of anti-Her2-Phor-18 antibody conjugates (scFv-$C_H$3-Phor-18 and -scFv-$C_H$3-(KLAKLAK)$_2$KLAK (SEQ ID NO. 68) conjugates, Her2/neu scFv-$C_H$3 and unconjugated Phor-18 in Her2 receptor positive SKOV-3, SKBR-3 and Her2 receptor negative MDA-MB-231 cancer cells. Values are $IC_{50}$ expressed in nM.

| Recombinant Antibody Conjugate | $IC_{50}$ [nM] SKOV-3 | $IC_{50}$ [nM] SKBR-3 | $IC_{50}$ [nM] MDA-MB-231 |
|---|---|---|---|
| Phor-18-scFv-$C_H$3-Phor-18 | 44.33 ± 9.2 | 51.56 ± 6.1 | >1000 |
| scFv-$C_H$3-GS-Phor-18 | 27 ± 2.5 | 30 ± 1.9 | >1000 |
| scFv-$C_H$3-GS-(KLAKLAK)$_2$KLAK | 235 ± 6.5 | 246 ± 41 | >1000 |
| scFv-$C_H$3-NRVRRS-Phor18 | 29.3 ± 3.5 | 76.3 ± 16 | >1000 |
| scFv-$C_H$3-NRVRRS-(KLAKLAK)$_2$KLAK | 247 ± 40.5 | 338 ± 8.7 | >1000 |
| Her2/neu scFv-$C_H$3 | >1000 | >1000 | >1000 |
| Phor-18 | 18,180 | 11,455 | 9,258 | increasing concentrations of 0, 0.00001, 0.0001, 0.001, 0.01, 0.1, 1, 10, 25, and 100 μM. The Her2-antibody-Phor-18 conjugates (Phor18-scFv-$C_H$3-Phor-18, scFv-$C_H$3-GS-Phor-18, scFv-$C_H$3-NRVRRS (SEQ. ID NO. 57)-Phor-18, the Her2-antibody-(KLAKLAK)$_2$KLAK (SEQ. ID NO. 68) (scFv-$C_H$3-GS-(KLAKLAK)$_2$KLAK (SEQ. ID NO. 66), and scFv-$C_H$3-NRVRRS-(KLAKLAK)$_2$KLAK (SEQ. ID NO. 69), or scFv-$C_H$3-receptor antibody (naked) in Tris/HCL-buffer were diluted with saline and added to cells at increasing concentrations of 0, 0.0012, 0.012, 0.12, 1.2, 6.0, 12.0, 120, 360 and 720 nM. Incubations were conducted for 48 h at 37° C. Cell viability was determined using formazan conversion assays (MTT assays). Controls contained USP saline or 0.1% TritonX-100™ as reference for 0 and 100% cell death, respectively. All data were processed and analyzed using Graph Pad Prizm 4™ software (Graph Pad Prizm, Inc).

Example 3

This example describes studies indicating that anti-Her2-Phor-18 antibody conjugate killed her2 expressing breast cancer cells.

As shown in Table 2, the anti-Her2-Phor-18 antibody conjugates (Phor18-scFv-$C_H$3-Phor-18, scFv-$C_H$3-GS-Phor-18, scFv-CH$_3$-NRVRRS (SEQ. ID NO. 57)-Phor-18) killed Her2 positive human breast cancer SKBR-3 and ovarian cancer SKOV-3 cell lines by 48 hours, whereas the Her2 negative human breast cancer MDA-MB-231 cell line was not killed. Evidence of cytotoxicity was observed microscopically at as early as 24 hours of incubation. As expected, unconjugated Phor-18 showed only modest cytotoxicity.

The HER2 antibody conjugated to the Phor-18 was significantly more cytotoxic than antibody conjugated to the lytic peptide (KLAKLAK)$_2$KLAK (SEQ. ID NO. 68). (FIG. 1, Table 2). The Her2 negative MDA-MB-231 cells were not killed by any of the recombinant antibody-lytic peptide conjugates indicating that the cytotoxicity of the antibodies was mediated via Her2/neu receptors. The "naked" (unconjugated) antibody (scFv-$C_H$3) was not cytotoxic in all 3 cell lines indicating that the cell-killing properties of the The results indicate that recombinantly produced Her2 antibody scFv-$C_H$3-Phor-18 and Her2 antibody scFv-$C_H$3-(KLAKLAK)$_2$KLAK (SEQ. ID NO. 68) conjugates are active in the nanomolar range against Her2/neu receptor expressing cell lines. The unconjugated antibody or free lytic peptide (Phor-18) were without effect indicating that conjugation of lytic peptides to ligands (e.g., antibodies) that bind to Her2/neu receptor to enhances cell cytotoxic potency.

Example 4

This example includes a description of in vitro cytotoxicity studies of recombinantly produced antibody to Her-2 receptor conjugated to lytic peptide, Phor-18 (KFAKFAK KFAKFAK KFAK (SEQ. ID NO. 67)) (scFv-$C_H$3-GS-Phor-18), and a chemically conjugated MAb-Phor18 conjugate against Her2 positive ovarian cancer cell line SKOV-3.

Cells were prepared in 96 well plates using 5,000 cells/well and were allowed to attach for 48 hours. MAb-Phor18, scFv-$C_H$3-GS-Phor-18, scFv-$C_H$3 were diluted in saline and added at increasing concentrations of 0, 0.0012, 0.012, 0.12, 1.2, 6.0, 12, 120, 360 and 720 nM, N=8 data points per concentration. Incubations were conducted for 24 h at 37° C. Cell viability was determined using formazan conversion assays (MTT assays). Controls contained USP saline or 0.1% TritonX-100™ as reference for 0 and 100% cell death, respectively.

Data were processed and analyzed using Graph Pad Prizm 4™ software (Graph Pad Prizm, Inc). Statistical analysis for significance was determined by a two-tailed Student's T-test. The whole MAb-Phor-18 resulted in $IC_{50}$ values of 60.53±3.8 nM and scFv-$C_H$3-GS-Phor-18 was 59.8±3.8 nM. The "naked" (unconjugated) antibodies (MAb and scFv-$C_H$3) were not cytotoxic. In vitro chemically linked HER2 antibody (MAb-Phor18) and recombinant Phor18 conjugate (scFv-$C_H$3-GS-Phor-18) showed similar toxicity to SKOV-3 cells, whereas the naked recombinant antibody (scFv-$C_H$3) was not toxic.

Example 5

This example describes an in vivo study in a mouse xenograft model of human ovarian cancer with various doses of anti-Her2-Phor-18 antibody conjugates (scFv-$C_H$3-

GS-Phor-18, MAb-Phor18), naked whole antibody (MAb) and naked recombinant antibody (scFv-$C_H$3) treatments.

Female Nu/Nu mice were injected subcutaneously with a SKOV-3/Matrigel suspension (4×10⁶ cells). Tumor weights from mice that were killed on day 42 served as baseline. In brief, treatment started on day 43 after tumor cell injection on tumors of median tumor volume of 130.3±10.25 mm³ and continued on days 47, 50, 54, 57 and 60 as a single bolus injection into the lateral tail vein.

During the entire study tumor volumes were measured twice per week and body weights were determined. Final necropsy was conducted on day 64 after tumor cell injection where tumors were excised, weighed and fixed in formalin for histological evaluation.

Treatments were saline control, whole naked monoclonal anti-Her2-antibody, MAb, (3 mg/kg), recombinant naked-Her2-antibody (scFv-$C_H$3) (3 mg/kg), scFv-$C_H$3-GS-Phor-18 (0.3 and 3 mg/kg), MAb-Phor-18 (0.3 and 3 mg/kg). Tumors from mice sacrificed at treatment start underwent immunohistochemistry evaluation of Her2/neu receptors. Each group consisted of 8-9 mice.

All groups of mice tolerated the injections well. No mice died as a consequence of injection.

Figure 4:
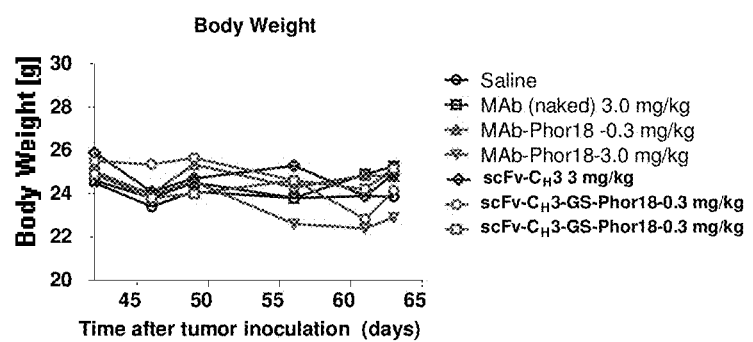
FIG. 4 shows mean body weights from mice treated with MAb (naked), MAb-Phor18 and recombinantly scFv-$C_H3$ naked antibody and scFv-$C_H3$-Phor-18 conjugates during the study period of 64 days in SKOV-3 xenografted mice in comparison with saline injected mice.

The effect of antibody conjugated Phor-18 injections and naked antibodies on the primary tumors (volume and tumor weights, FIGS. 2A, 2B, and 3) and body weight is illustrated in FIG. 4. FIGS. 2A and 2B show median tumor volumes during the course of the study and mean tumor weights on day 64 for each individual treatment group for saline controls, and mice treated with MAb (naked) (3 mg/kg), scFv-$C_H$3 (3 mg/kg), scFv-$C_H$3-GS-Phor-18 (0.3 and 3 mg/kg), MAb-Phor-18 (0.3 and 3 mg/kg).

Tumor volumes and weights decreased significantly in all animals treated with 3 mg/kg MAb-Phor-18 chemically linked (p<0.04) or recombinantly produced scFv-$CH_3$-Phor-18 conjugates (p<0.02). Naked MAb or scFv-$C_H$3 were not decreasing tumor volumes or tumor weights compared to saline controls at doses of 3 mg/kg (FIGS. 2A, 2B, and 3). Statistical analysis was conducted in Graphpad prizm 4 using the Wilcoxon signed rank test. Body weights were stable in all treatment groups and control animals (FIG. 4).

Example 6

This example describes in vitro cytotoxicity studies of recombinantly produced antibody to Her-2 receptor conjugated to lytic peptide, Phor-18 (KFAKFAK KFAKFAK KFAK (SEQ. ID NO. 67)) against ovarian cancer cells.

scFv-$C_H$2-$C_H$3-GS-Phor-18 (one molecule of Phor-18 joined to the antibody at the C-terminus by GS linker, consisting of $V_L$-G linker-$V_H$—$C_H$2-$C_H$3-G linker $C_H$3-$C_H$2-$V_H$-G linker-$V_L$-GS-(Phor-18). Cytotoxicity was compared to a naked antibody (scFv-$C_H$2-$C_H$3; antibody without a lytic peptide) in Her-2 receptor positive cells (SKOV-3, human ovarian cancer cells).

Materials:

Recombinant DNA technique was used to synthesize anti-Her2 antibody as an scFv-$C_H$2-$C_H$3 antibody in *Escherichia coli*. The antibody (Olafsen T. et al *Protein Engineering, Design & Selection* 17, 315-323, 2004) was conjugated via a peptide linker to either Phor-18 and analyzed for cytotoxicity in vitro. The plasmid was acquired through gene codon optimization. The gene was synthesized with a N-His tag sequence and the plasmid was subcloned into an *E. coli* bacteria expression vector pUC57. After expression optimization and evaluation the His-tag product was selected and 1 L of the bacteria expression product was purified in a one-step affinity purification. The amino acid sequence of for each construct is described in Table 3.

TABLE 3

Amino Acid sequence for the production of each recombinant antibody,
(A)
scFv-$C_H$2—$C_H$3; and antibody conjugate (B) scFv-$C_H$2—$C_H$3-GS-Phor-18.

A)

(SEQ ID NO: 64)

```
DIQMTQSPSSLSASVGDRVTITCRASQDVNTAVAWYQQKPGKAPKLLIYSASFLYSGVPSRFSGS
RSGTDFTLTISSLQPEDFATYYCQQHYTTPPTFGQGTKVEIK

--------------------GSTSGGGSGGGSGGGGSS----------------------

EVQLVESGGGLVQPGGSLRLSCAASGFNIKDTYIHWVRQAPGKGLEWVARIYPTNGYTRYADS
VKGRFTISADTSKNTAYLQMNSLRAEDTAVYYCSRWGGDGFYAMDYVVGQGTLVTVSS
PCPAPELLGGPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPAPIEKTISKAK

GQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK
--------------------GSTSGGGSGGGSGGGGSS----------------------
GQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK
PCPAPELLGGPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPAPIEKTISKAK

EVQLVESGGGLVQPGGSLRLSCAASGFNIKDTYIHVVVRQAPGKGLEWVARIYPTNGYTRYADS
VKGRFTISADTSKNTAYLQMNSLRAEDTAVYYCSRWGGDGFYAMDYWGQGTLVTVSS
--------------------GSTSGGGSGGGSGGGGSS----------------------
DIQMTQSPSSLSASVGDRVTITCRASQDVNTAVAWYQQKPGKAPKLLIYSASFLYSGVPS
RFSGSRSGTDFTLTISSLQPEDFATYYCQQHYTTPPTFGQGTKVEIK
```

TABLE 3-continued

Amino Acid sequence for the production of each recombinant antibody,
(A)
scFv-$C_H$2-$C_H$3; and antibody conjugate (B) scFv-$C_H$2-$C_H$3-GS-Phor-18.

B)

(SEQ ID NO: 65)
DIQMTQSPSSLSASVGDRVTITCRASQDVNTAVAWYQQKPGKAPKLLIYSASFLYSGVPSRFSGS
RSGTDFTLTISSLQPEDFATYYCQQHYTTPPTFGQGTKVEIK

---------------------GSTSGGGSGGGSGGGGSS----------------------

EVQLVESGGGLVQPGGSLRLSCAASGFNIKDTYIHWVRQAPGKGLEWVARIYPTNGYTRYADS
VKGRFTISADTSKNTAYLQMNSLRAEDTAVYYCSRWGGDGFYAMDYWGQGTLVTVSS
PCPAPELLGGPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPAPIEKTISKAK

GQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK
---------------------GSTSGGGSGGGSGGGSS---------------------
GQPREPQVYTLPPSRDELTKNQVSLTCLVKGFYPSDIAVEWESNGQPENNYKTTPPVLD
SDGSFFLYSKLTVDKSRWQQGNVFSCSVMHEALHNHYTQKSLSLSPGK
PCPAPELLGGPSVFLFPPKPKDTLMISRTPEVTCVVVDVSHEDPEVKFNWYVDGV
EVHNAKTKPREEQYNSTYRVVSVLTVLHQDWLNGKEYKCKVSNKALPAPIEKTISKAK

EVQLVESGGGLVQPGGSLRLSCAASGFNIKDTYIHWVRQAPGKGLEWVARIYPTNGYTRYADS
VKGRFTISADTSKNTAYLQMNSLRAEDTAVYYCSRWGGDGFYAMDYWGQGTLVTVSS
---------------------GSTSGGGSGGGSGGGGSS---------------------

DIQMTQSPSSLSASVGDRVTITCRASQDVNTAVAWYQQKPGKAPKLLIYSASFLYSGVPSRFSGS
RSGTDFTLTISSLQPEDFATYYCQQHYTTPPTFGQGTKVEIK

GS KFAKFAKKFAKFAKKFAK

In vitro cytotoxicity studies were performed to determine cytotoxicity of the recombinant antibody preparations (scFv-$C_H$2-$C_H$3, scFv-$C_H$3, and scFv-$C_H$2-$C_H$3-GS-Phor-18, scFv-$C_H$3-GS-Phor-18). Her-2 receptor positive SKOV-3 cells were prepared in 96 well plates using 2,000 cells/well and were allowed to attach for 48 hours. The Her2-antibody-Phor-18 conjugates (scFv-$C_H$2-$C_H$3-GS-Phor-18, scFv-$C_H$3 GS-Phor-18) or the naked antibodies (scFv-$C_H$2-$C_H$3, scFv-$C_H$3) in Tris/HCL-buffer were diluted with saline and added to cells at increasing concentrations of 0, 0.0012, 0.012, 0.12, 1.2, 6.0, 12.0, 120, 360 and 720 nM. Incubations were conducted for 48 h at 37° C. Cell viability was determined using Cell Titer Glo luminescent cell viability assay (Promega). Controls contained USP saline or 0.1% TritonX-100™ as reference for 0 and 100% cell death, respectively. All data were processed and analyzed using Graph Pad Prizm 4™ software (Graph Pad Prizm, Inc).

The Her2 antibody (scFv-$C_H$2-$C_H$3, scFv-$C_H$3) conjugated to the Phor-18 resulted in $IC_{50}$ values of 53.7±0.63 nM for scFv-$C_H$3-Phor18 and 56.7±0.92 nM for scFv-$CH_2$—$CH_3$—Fv-Phor-18. The "naked" (unconjugated) antibodies, scFv-$C_H$2-$C_H$3, scFv-$C_H$3, were not cytotoxic. In vitro recombinantly Phor-18 conjugates show similar toxicity to SKOV-3 cells.

What is claimed:

1. A conjugate comprising an antibody or an antibody fragment that binds to Her2/neu and a second domain, wherein said second domain consists of a 15 to 20 amino acid sequence that includes a peptide selected from the group consisting of KFAKFAKKFAKFAKK (SEQ. ID NO. 1), KFAKFAKKFAKFAKKF (SEQ. ID NO. 2), KFAKFAK-KFAKFAKKFA (SEQ. ID NO. 3), KFAKFAKKFAKFAK-KFAK (SEQ. ID NO. 4), KFAKFAKKFAKFAKKFAKF (SEQ. ID NO. 5) and KFAKFAKKFAKFAKKFAKFA (SEQ. ID NO. 6).

2. A conjugate comprising an antibody or an antibody fragment that binds to Her2/neu and a second domain, wherein said second domain consists of an amino acid sequence selected from the group consisting of KFAKFAK-KFAKFAKK (SEQ. ID NO. 1), KFAKFAKKFAKFAKKF (SEQ. ID NO. 2), KFAKFAKKFAKFAKKFA (SEQ. ID NO. 3), KFAKFAKKFAKFAKKFAK (SEQ. ID NO. 4), KFAK-FAKKFAKFAKKFAKF (SEQ. ID NO. 5) and KFAKFAK-KFAKFAKKFAKFA (SEQ. ID NO. 6).

3. The conjugate of claim 1 or 2, wherein said antibody fragment comprises an Fab, Fab', F(ab)$_2$, Fv, Fd, single-chain Fv (scFv), disulfide-linked Fvs (sdFv), V$_L$, V$_H$, Camel Ig, V-NAR, VHH, trispecific (Fab$_3$), bispecific (Fab$_2$), diabody ((V$_L$-V$_H$)$_2$ or (V$_H$-V$_L$)$_2$), triabody (trivalent), tetrabody (tetravalent), minibody ((scF$_v$-C$_H$3)$_2$), bispecific single-chain Fv (Bis-scFv), IgGdeltaC$_H$2, scFv-Fc, (scFv)$_2$-Fc, affibody, aptamer, avimer or nanobody.

4. The conjugate of claim 1 or 2, wherein said antibody or antibody fragment comprises a monoclonal antibody.

5. The conjugate of claim 1 or 2, wherein said antibody or antibody fragment comprises a mammalian antibody or antibody fragment.

6. The conjugate of claim 1 or 2, wherein said antibody or antibody fragment comprises a human, humanized, primatized, or chimeric antibody or antibody fragment.

7. The conjugate of claim 1 or 2, wherein said antibody comprises trastuzumab or pertuzumab.

8. The conjugate of claim 1 or 2, wherein said Her2/neu is expressed on a cell.

9. The conjugate of claim 8, wherein said cell is a hyperproliferative cell.

10. The conjugate of claim 8, wherein said cell is a breast, ovarian, uterine, cervical, prostate, stomach, lung, gastric, colon, bladder, glial, hematologic or endometrial cell.

11. The conjugate of claim 1 or 2, wherein said second domain is positioned at the NH$_2$-terminus relative to said antibody or antibody fragment that binds to Her2/neu, or wherein said second domain is positioned at the C-terminus relative to said antibody or antibody fragment that binds to Her2/neu, or wherein said antibody or antibody fragment that binds to Her2/neu is positioned at the NH$_2$-terminus relative to said second domain, or wherein said antibody or antibody fragment that binds to Her2/neu is positioned at the C-terminus relative to said second domain.

12. The conjugate of claim 1 or 2, wherein said second domain has one or more D-amino acids.

13. The conjugate of claim 1 or 2, wherein said second domain forms an amphipathic alpha-helix.

14. The conjugate of claim 1 or 2, wherein said antibody or antibody fragment that binds to Her2/neu and said second domain are joined by a covalent bond.

15. The conjugate of claim 1 or 2, wherein said antibody or antibody fragment that binds to Her2/neu and said second domain are joined by a peptide linker.

16. The conjugate of claim 1 or 2, wherein said antibody or antibody fragment that binds to Her2/neu and said second domain are joined by a peptide sequence having from 1 to 25 amino acid residues.

17. The conjugate of claim 1 or 2, further comprising a third, fourth, fifth, sixth or seventh domain.

18. The conjugate of claim 1 or 2, wherein said conjugate is isolated or purified.

19. The conjugate of claim 1 or 2, wherein said conjugate comprises a mixture.

20. A composition comprising the conjugate of claim 1 or 2.

21. A pharmaceutical composition comprising the conjugate of claim 1 or 2.

22. A composition comprising the conjugate of claim 1 or 2, and an anti-cell proliferative or immune stimulating agent.

23. A unit dosage, comprising the conjugate of claim 1 or 2 in an amount effective to treat a subject having a neoplasia, tumor or cancer.

24. A kit comprising the conjugate of claim 1 or 2 and instructions for reducing or inhibiting proliferation of a cell, reducing or inhibiting proliferation of a hyperproliferating cell, reducing or inhibiting proliferation of a neoplastic, tumor or cancer cell, treating a subject having a hyperproliferative disorder, or treating a subject having a neoplasia, tumor or cancer.

25. A nucleic acid molecule that encodes the conjugate of claim 1 or 2.

26. A method of reducing or inhibiting proliferation of a cell, comprising contacting a cell with the conjugate of claim 1 or 2 in an amount sufficient to reduce or inhibit proliferation of the cell.

27. A method of reducing or inhibiting proliferation of a hyperproliferating cell, comprising contacting a cell with the conjugate of claim 1 or 2 in an amount sufficient to reduce or inhibit proliferation of the hyperproliferating cell.

28. A method of reducing or inhibiting proliferation of a neoplastic, tumor, cancer or malignant cell, comprising contacting the cell with the conjugate of claim 1 or 2 in an amount sufficient to reduce or inhibit proliferation of the neoplastic, tumor, cancer or malignant cell.

29. The method of any of claims 26 or 28, wherein the cell expresses Her2/neu.

30. A method of selectively reducing or inhibiting proliferation of a cell that expresses Her2/neu, comprising contacting the cell with the conjugate of claim 1 or 2 in an amount sufficient to reduce or inhibit proliferation of the cell that expresses Her2/neu.

31. A method of selectively reducing or inhibiting proliferation of a neoplastic, tumor, cancer or malignant cell that expresses a receptor or antigen, comprising contacting the cell with the conjugate of claim 1 or 2 in an amount sufficient to reduce or inhibit proliferation of the neoplastic, tumor, cancer or malignant cell that expresses Her2/neu.

32. A method of treating a subject having a hyperproliferative disorder, comprising administering to the subject an amount of the conjugate of claim 1 or 2 sufficient to treat the hyperproliferative disorder.

33. A method of treating a subject having a neoplasia, tumor, cancer or malignancy, comprising administering to the subject an amount of the conjugate of claim 1 or 2 sufficient to reduce or inhibit proliferation of the neoplasia, tumor, cancer or malignancy.

34. The method of claim 31 or 33, wherein the neoplasia, tumor, cancer or malignancy is metastatic, non-metastatic or benign.

35. The method of claim 31 or 33, wherein the neoplasia, tumor, cancer or malignancy comprises a solid cellular mass.

36. The method of claim 31 or 33, wherein the neoplasia, tumor, cancer or malignancy comprises hematopoietic cells.

37. The method of claim 31 or 33, wherein the neoplasia, tumor, cancer or malignancy comprises a carcinoma, sarcoma, lymphoma, leukemia, adenoma, adenocarcinoma, melanoma, glioma, glioblastoma, meningioma, neuroblastoma, retinoblastoma, astrocytoma, oligodendrocytoma, mesothelioma, reticuloendothelial, lymphatic or haematopoietic neoplasia, tumor, cancer or malignancy.

38. The method of claim 37, wherein the sarcoma comprises a lymphosarcoma, liposarcoma, osteosarcoma, chondrosarcoma, leiomyosarcoma, rhabdomyosarcoma or fibrosarcoma.

39. The method of claim 37, wherein the haematopoietic neoplasia, tumor, cancer or malignancy comprises a myeloma, lymphoma or leukemia.

40. The method of claim 31 or 33, wherein the neoplasia, tumor, cancer or malignancy comprises a lung, thyroid, head or neck, nasopharynx, throat, nose or sinuses, brain, spine, breast, adrenal gland, pituitary gland, thyroid, lymph, gastrointestinal (mouth, esophagus, stomach, duodenum, ileum, jejunum (small intestine), colon, rectum), genito-urinary tract (uterus, ovary, cervix, endometrial, bladder, testicle, penis, prostate), kidney, pancreas, liver, bone, bone marrow, lymph, blood, muscle, or skin, wilm's, biliary tract, B-ALL, or hematologic neoplasia, tumor, cancer, or cancer.

41. The method of claim 40, wherein the lung neoplasia, tumor, cancer or malignancy comprises small cell lung or non-small cell lung cancer.

42. The method of claim 31 or 33, further comprising administering an anti-cell proliferative, anti-neoplastic, anti-tumor, anti-cancer or immune-enhancing treatment or therapy.

43. The method of claim 31 or 33, wherein the treatment results in partial or complete destruction of the neoplastic, tumor, cancer or malignant cell mass, volume, size or numbers of cells, stimulating, inducing or increasing neoplastic, tumor, cancer or malignant cell necrosis, lysis or apoptosis, reducing neoplasia, tumor, cancer or malignancy volume size, cell mass, inhibiting or preventing progression or an increase in neoplasia, tumor, cancer or malignancy volume, mass, size or cell numbers, or prolonging lifespan.

44. The method of claim 31 or 33, wherein the subject is a mammal.

45. The method of claim 31 or 33, wherein the subject is a human.

46. The conjugate of claim 15, wherein the peptide linker comprises a GS linker.

47. The conjugate of claim 1 or 2, wherein said ligand that binds to Her2/neu and said second domain are joined by a linear carbon chain.

* * * * *

SEQUENCE LISTING

```
<160> NUMBER OF SEQ ID NOS: 69

<210> SEQ ID NO 1
<211> LENGTH: 15
<212> TYPE: PRT
<213> ORGANISM: Artificial Sequence
<220> FEATURE:
<223> OTHER INFORMATION: Description of Artificial Sequence: Lytic
      peptide

<400> SEQUENCE: 1

Lys Phe Ala Lys Phe Ala Lys Lys Phe Ala Lys Phe Ala Lys Lys
1               5                   10                  15

<210> SEQ ID NO 2
<211> LENGTH: 16
<212> TYPE: PRT
<213> ORGANISM: Artificial Sequence
<220> FEATURE:
<223> OTHER INFORMATION: Description of Artificial Sequence: Lytic
      peptide
```

```
<400> SEQUENCE: 2

Lys Phe Ala Lys Phe Ala Lys Lys Phe Ala Lys Phe Ala Lys Lys Phe
1               5                   10                  15

<210> SEQ ID NO 3
<211> LENGTH: 17
<212> TYPE: PRT
<213> ORGANISM: Artificial Sequence
<220> FEATURE:
<223> OTHER INFORMATION: Description of Artificial Sequence: Lytic
      peptide

<400> SEQUENCE: 3

Lys Phe Ala Lys Phe Ala Lys Lys Phe Ala Lys Phe Ala Lys Lys Phe
1               5                   10                  15

Ala

<210> SEQ ID NO 4
<211> LENGTH: 18
<212> TYPE: PRT
<213> ORGANISM: Artificial Sequence
<220> FEATURE:
<223> OTHER INFORMATION: Description of Artificial Sequence: Lytic
      peptide

<400> SEQUENCE: 4

Lys Phe Ala Lys Phe Ala Lys Lys Phe Ala Lys Phe Ala Lys Lys Phe
1               5                   10                  15

Ala Lys

<210> SEQ ID NO 5
<211> LENGTH: 19
<212> TYPE: PRT
<213> ORGANISM: Artificial Sequence
<220> FEATURE:
<223> OTHER INFORMATION: Description of Artificial Sequence: Lytic
      peptide

<400> SEQUENCE: 5

Lys Phe Ala Lys Phe Ala Lys Lys Phe Ala Lys Phe Ala Lys Lys Phe
1               5                   10                  15

Ala Lys Phe

<210> SEQ ID NO 6
<211> LENGTH: 20
<212> TYPE: PRT
<213> ORGANISM: Artificial Sequence
<220> FEATURE:
<223> OTHER INFORMATION: Description of Artificial Sequence: Lytic
      peptide

<400> SEQUENCE: 6

Lys Phe Ala Lys Phe Ala Lys Lys Phe Ala Lys Phe Ala Lys Lys Phe
1               5                   10                  15

Ala Lys Phe Ala
            20

<210> SEQ ID NO 7
<211> LENGTH: 28
<212> TYPE: PRT
<213> ORGANISM: Artificial Sequence
<220> FEATURE:
<223> OTHER INFORMATION: Description of Artificial Sequence: Lytic
      peptide
```

```
<400> SEQUENCE: 7

Lys Phe Ala Lys Phe Ala Lys Lys Phe Ala Lys Phe Ala Lys Lys Phe
1               5                   10                  15

Ala Lys Phe Ala Lys Lys Phe Ala Lys Phe Ala Lys
            20                  25

<210> SEQ ID NO 8
<211> LENGTH: 15
<212> TYPE: PRT
<213> ORGANISM: Artificial Sequence
<220> FEATURE:
<223> OTHER INFORMATION: Description of Artificial Sequence: Lytic
      peptide

<400> SEQUENCE: 8

Lys Phe Ala Lys Phe Ala Lys Lys Phe Ala Lys Phe Ala Lys Lys
1               5                   10                  15

<210> SEQ ID NO 9
<211> LENGTH: 16
<212> TYPE: PRT
<213> ORGANISM: Artificial Sequence
<220> FEATURE:
<223> OTHER INFORMATION: Description of Artificial Sequence: Lytic
      peptide

<400> SEQUENCE: 9

Lys Phe Ala Lys Phe Ala Lys Lys Phe Ala Lys Phe Ala Lys Lys Phe
1               5                   10                  15

<210> SEQ ID NO 10
<211> LENGTH: 17
<212> TYPE: PRT
<213> ORGANISM: Artificial Sequence
<220> FEATURE:
<223> OTHER INFORMATION: Description of Artificial Sequence: Lytic
      peptide

<400> SEQUENCE: 10

Lys Phe Ala Lys Phe Ala Lys Lys Phe Ala Lys Phe Ala Lys Lys Phe
1               5                   10                  15

Ala

<210> SEQ ID NO 11
<211> LENGTH: 18
<212> TYPE: PRT
<213> ORGANISM: Artificial Sequence
<220> FEATURE:
<223> OTHER INFORMATION: Description of Artificial Sequence: Lytic
      peptide

<400> SEQUENCE: 11

Lys Phe Ala Lys Phe Ala Lys Lys Phe Ala Lys Phe Ala Lys Lys Phe
1               5                   10                  15

Ala Lys

<210> SEQ ID NO 12
<211> LENGTH: 19
<212> TYPE: PRT
<213> ORGANISM: Artificial Sequence
<220> FEATURE:
<223> OTHER INFORMATION: Description of Artificial Sequence: Lytic
      peptide

<400> SEQUENCE: 12
```

Lys Phe Ala Lys Phe Ala Lys Lys Phe Ala Lys Phe Ala Lys Lys Phe
1               5                   10                  15

Ala Lys Phe

<210> SEQ ID NO 13
<211> LENGTH: 20
<212> TYPE: PRT
<213> ORGANISM: Artificial Sequence
<220> FEATURE:
<223> OTHER INFORMATION: Description of Artificial Sequence: Lytic
      peptide

<400> SEQUENCE: 13

Lys Phe Ala Lys Phe Ala Lys Lys Phe Ala Lys Phe Ala Lys Lys Phe
1               5                   10                  15

Ala Lys Phe Ala
            20

<210> SEQ ID NO 14
<211> LENGTH: 5
<212> TYPE: PRT
<213> ORGANISM: Artificial Sequence
<220> FEATURE:
<223> OTHER INFORMATION: Description of Artificial Sequence: Linker
      peptide

<400> SEQUENCE: 14

Gly Ser Gly Gly Ser
1               5

<210> SEQ ID NO 15
<211> LENGTH: 5
<212> TYPE: PRT
<213> ORGANISM: Artificial Sequence
<220> FEATURE:
<223> OTHER INFORMATION: Description of Artificial Sequence: Linker
      peptide

<400> SEQUENCE: 15

Ala Ser Ala Ala Ser
1               5

<210> SEQ ID NO 16
<211> LENGTH: 6
<212> TYPE: PRT
<213> ORGANISM: Artificial Sequence
<220> FEATURE:
<223> OTHER INFORMATION: Description of Artificial Sequence: Linker
      peptide

<400> SEQUENCE: 16

Cys Cys Cys Cys Cys Cys
1               5

<210> SEQ ID NO 17
<211> LENGTH: 6
<212> TYPE: PRT
<213> ORGANISM: Artificial Sequence
<220> FEATURE:
<223> OTHER INFORMATION: Description of Artificial Sequence: Linker
      peptide

<400> SEQUENCE: 17

Gly Ser Gly Arg Ser Ala
1               5

```
<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Linker
      peptide

<400> SEQUENCE: 18

Arg Val Arg Arg Ser Val
1               5

<210> SEQ ID NO 19
<211> LENGTH: 7
<212> TYPE: PRT
<213> ORGANISM: Artificial Sequence
<220> FEATURE:
<223> OTHER INFORMATION: Description of Artificial Sequence: Motif

<400> SEQUENCE: 19

Pro Asn Asn Pro Asn Asn Pro
1               5

<210> SEQ ID NO 20
<211> LENGTH: 58
<212> TYPE: PRT
<213> ORGANISM: Artificial Sequence
<220> FEATURE:
<223> OTHER INFORMATION: Description of Artificial Sequence: Mammalian
      humanized antibody

<400> SEQUENCE: 20

Val Asp Asn Lys Phe Asn Lys Glu Gln Gln Asn Ala Phe Tyr Glu Ile
1               5                   10                  15

Leu His Leu Pro Asn Leu Asn Glu Glu Gln Arg Asn Ala Phe Ile Gln
            20                  25                  30

Ser Leu Lys Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 21
<211> LENGTH: 58
<212> TYPE: PRT
<213> ORGANISM: Artificial Sequence
<220> FEATURE:
<223> OTHER INFORMATION: Description of Artificial Sequence: Mammalian
      humanized antibody

<400> SEQUENCE: 21

Val Asp Asn Lys Phe Asn Lys Glu Leu Arg Gln Ala Tyr Trp Glu Ile
1               5                   10                  15

Gln Ala Leu Pro Asn Leu Asn Trp Thr Gln Ser Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 22
<211> LENGTH: 58
<212> TYPE: PRT
<213> ORGANISM: Artificial Sequence
<220> FEATURE:
<223> OTHER INFORMATION: Description of Artificial Sequence: Mammalian
```

-continued humanized antibody

<400> SEQUENCE: 22

Val Asp Asn Lys Phe Asn Lys Glu Pro Lys Thr Ala Tyr Trp Glu Ile
1               5                   10                  15

Val Lys Leu Pro Asn Leu Asn Pro Glu Gln Arg Arg Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 23
<211> LENGTH: 58
<212> TYPE: PRT
<213> ORGANISM: Artificial Sequence
<220> FEATURE:
<223> OTHER INFORMATION: Description of Artificial Sequence: Mammalian
      humanized antibody

<400> SEQUENCE: 23

Val Asp Asn Lys Phe Asn Lys Glu Pro Arg Glu Ala Tyr Trp Glu Ile
1               5                   10                  15

Gln Arg Leu Pro Asn Leu Asn Asn Lys Gln Lys Ala Ala Phe Ile Arg
            20                  25                  30

Ser Leu Tyr Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 24
<211> LENGTH: 58
<212> TYPE: PRT
<213> ORGANISM: Artificial Sequence
<220> FEATURE:
<223> OTHER INFORMATION: Description of Artificial Sequence: Mammalian
      humanized antibody

<400> SEQUENCE: 24

Val Asp Asn Lys Phe Asn Lys Glu Trp Met Thr Ala Gly Lys Glu Ile
1               5                   10                  15

Tyr Arg Leu Pro Asn Leu Asn Gly Thr Gln Val Arg Ala Phe Ile Gln
            20                  25                  30

Ser Leu Ser Asp Asp Pro Ser Gln Ser Ala Asn Leu Leu Ala Glu Ala
        35                  40                  45

Lys Lys Leu Asn Asp Ala Gln Ala Pro Lys
    50                  55

<210> SEQ ID NO 25
<211> LENGTH: 58
<212> TYPE: PRT
<213> ORGANISM: Artificial Sequence
<220> FEATURE:
<223> OTHER INFORMATION: Description of Artificial Sequence: Mammalian
      humanized antibody

<400> SEQUENCE: 25

Val Asp Asn Lys Phe Asn Lys Glu Trp Val Gln Ala Gly Ser Glu Ile
1               5                   10                  15

Tyr Asn Leu Pro Asn Leu Asn Arg Ala Gln Met Arg Ala Phe Ile Arg
            20                  25                  30

Ser Leu Ser Asp Asp Pro Ser Gln Ser Ala Asn Leu Leu Ala Glu Ala
            35                  40                  45

Lys Lys Leu Asn Asp Ala Gln Ala Pro Lys
 50                  55

<210> SEQ ID NO 26
<211> LENGTH: 58
<212> TYPE: PRT
<213> ORGANISM: Artificial Sequence
<220> FEATURE:
<223> OTHER INFORMATION: Description of Artificial Sequence: Mammalian
      humanized antibody

<400> SEQUENCE: 26

Val Asp Asn Lys Phe Asn Lys Glu Ile Lys Gln Ala Phe His Glu Ile
 1               5                  10                  15

Val Arg Leu Pro Asn Leu Asn Ala Asp Gln Val Arg Ala Phe Ile Tyr
                20                  25                  30

Ser Leu Gly Asp Asp Pro Ser Gln Ser Ala Asn Leu Leu Ala Glu Ala
            35                  40                  45

Lys Lys Leu Asn Asp Ala Gln Ala Pro Lys
 50                  55

<210> SEQ ID NO 27
<211> LENGTH: 57
<212> TYPE: PRT
<213> ORGANISM: Artificial Sequence
<220> FEATURE:
<223> OTHER INFORMATION: Description of Artificial Sequence: Mammalian
      humanized antibody

<400> SEQUENCE: 27

Val Asp Asn Lys Phe Asn Lys Glu Met Val Asp Ala Gly Ala Glu Ile
 1               5                  10                  15

Trp Arg Leu Pro Asn Leu Asn Ala Lys Gln Met Ala Phe Ile Asp Ser
                20                  25                  30

Leu Gly Asp Asp Pro Ser Gln Ser Ala Asn Leu Leu Ala Glu Ala Lys
            35                  40                  45

Lys Leu Asn Asp Ala Gln Ala Pro Lys
 50                  55

<210> SEQ ID NO 28
<211> LENGTH: 107
<212> TYPE: PRT
<213> ORGANISM: Artificial Sequence
<220> FEATURE:
<223> OTHER INFORMATION: Description of Artificial Sequence: Light chain
      mammalian humanized antibody

<400> SEQUENCE: 28

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Glu Ser Gly Val Pro Ser Arg Phe Ser Gly
         50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro

```
                    85                  90                  95

Thr Phe Gly Gln Gly Thr Lys Val Glu Ile Lys
                100                 105

<210> SEQ ID NO 29
<211> LENGTH: 120
<212> TYPE: PRT
<213> ORGANISM: Artificial Sequence
<220> FEATURE:
<223> OTHER INFORMATION: Description of Artificial Sequence: Heavy
      chain mammalian humanized antibody

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Arg Asp Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Gly Asp Gly Phe Tyr Ala Met Asp Val Trp Gly Gln
            100                 105                 110

Gly Thr Leu Val Thr Val Ser Ser
        115                 120

<210> SEQ ID NO 30
<211> LENGTH: 107
<212> TYPE: PRT
<213> ORGANISM: Artificial Sequence
<220> FEATURE:
<223> OTHER INFORMATION: Description of Artificial Sequence: Light
      chain mammalian humanized antibody

<400> SEQUENCE: 30

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
                100                 105

<210> SEQ ID NO 31
<211> LENGTH: 120
<212> TYPE: PRT
<213> ORGANISM: Artificial Sequence
<220> FEATURE:
<223> OTHER INFORMATION: Description of Artificial Sequence: Heavy
``` chain mammalian humanized antibody

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Asp Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Trp Gly Gly Asp Gly Phe Tyr Ala Met Asp Val Trp Gly Gln
            100                 105                 110

Gly Thr Leu Val Thr Val Ser Ser
        115                 120

<210> SEQ ID NO 32
<211> LENGTH: 107
<212> TYPE: PRT
<213> ORGANISM: Artificial Sequence
<220> FEATURE:
<223> OTHER INFORMATION: Description of Artificial Sequence: Light
      chain mammalian humanized antibody

<400> SEQUENCE: 32

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Glu Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 33
<211> LENGTH: 120
<212> TYPE: PRT
<213> ORGANISM: Artificial Sequence
<220> FEATURE:
<223> OTHER INFORMATION: Description of Artificial Sequence: Heavy
      chain mammalian humanized antibody

<400> SEQUENCE: 33

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

```
Ala Arg Ile Tyr Pro Thr Asn Gly Tyr Thr Tyr Ala Asp Ser Val
        50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Val Trp Gly Gln
            100                 105                 110

Gly Thr Leu Val Thr Val Ser Ser
            115                 120

<210> SEQ ID NO 34
<211> LENGTH: 107
<212> TYPE: PRT
<213> ORGANISM: Artificial Sequence
<220> FEATURE:
<223> OTHER INFORMATION: Description of Artificial Sequence: Light
      chain mammalian humanized antibody

<400> SEQUENCE: 34

Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Glu Ser Gly Val Pro Ser Arg Phe Ser Gly
    50                  55                  60

Ser Arg Ser Gly Thr Asp Phe Thr Leu Thr Ile Ser Ser Leu Gln Pro
 65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 35
<211> LENGTH: 120
<212> TYPE: PRT
<213> ORGANISM: Artificial Sequence
<220> FEATURE:
<223> OTHER INFORMATION: Description of Artificial Sequence: Heavy
      chain mammalian humanized antibody

<400> SEQUENCE: 35

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Tyr Ala Asp Ser Val
        50                  55                  60

Lys Gly Arg Phe Thr Ile Ser Ala Asp Thr Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Val Trp Gly Gln
            100                 105                 110
```

Gly Thr Leu Val Thr Val Ser Ser
        115                 120

<210> SEQ ID NO 36
<211> LENGTH: 107
<212> TYPE: PRT
<213> ORGANISM: Artificial Sequence
<220> FEATURE:
<223> OTHER INFORMATION: Description of Artificial Sequence: Light
      chain mammalian humanized antibody

<400> SEQUENCE: 36

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Glu Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 37
<211> LENGTH: 120
<212> TYPE: PRT
<213> ORGANISM: Artificial Sequence
<220> FEATURE:
<223> OTHER INFORMATION: Description of Artificial Sequence: Heavy
      chain mammalian humanized antibody

<400> SEQUENCE: 37

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Val Trp Gly Gln
            100                 105                 110

Gly Thr Leu Val Thr Val Ser Ser
        115                 120

<210> SEQ ID NO 38
<211> LENGTH: 107
<212> TYPE: PRT
<213> ORGANISM: Artificial Sequence
<220> FEATURE:
<223> OTHER INFORMATION: Description of Artificial Sequence: Light chain
      mammalian humanized antibody -continued

```
<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 39
<211> LENGTH: 120
<212> TYPE: PRT
<213> ORGANISM: Artificial Sequence
<220> FEATURE:
<223> OTHER INFORMATION: Description of Artificial Sequence: Heavy chain
      mammalian humanized antibody

<400> SEQUENCE: 39

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Val Trp Gly Gln
            100                 105                 110

Gly Thr Leu Val Thr Val Ser Ser
        115                 120

<210> SEQ ID NO 40
<211> LENGTH: 107
<212> TYPE: PRT
<213> ORGANISM: Artificial Sequence
<220> FEATURE:
<223> OTHER INFORMATION: Description of Artificial Sequence: Light chain
      mammalian humanized antibody

<400> SEQUENCE: 40

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45
```

```
Tyr Ser Ala Ser Phe Leu Glu Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
                100                 105

<210> SEQ ID NO 41
<211> LENGTH: 120
<212> TYPE: PRT
<213> ORGANISM: Artificial Sequence
<220> FEATURE:
<223> OTHER INFORMATION: Description of Artificial Sequence: Heavy chain
      mammalian humanized antibody

<400> SEQUENCE: 41

Glu Val Gln Leu Val Glu Ser Gly Gly Leu Val Gln Pro Gly Gly
1               5                   10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
                100                 105                 110

Gly Thr Leu Val Thr Val Ser Ser
            115                 120

<210> SEQ ID NO 42
<211> LENGTH: 107
<212> TYPE: PRT
<213> ORGANISM: Artificial Sequence
<220> FEATURE:
<223> OTHER INFORMATION: Description of Artificial Sequence: Light chain
      mammalian humanized antibody

<400> SEQUENCE: 42

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
                20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
                100                 105
```

-continued

```
<210> SEQ ID NO 43
<211> LENGTH: 120
<212> TYPE: PRT
<213> ORGANISM: Artificial Sequence
<220> FEATURE:
<223> OTHER INFORMATION: Description of Artificial Sequence: Heavy chain
      mammalian humanized antibody

<400> SEQUENCE: 43

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 44
<211> LENGTH: 107
<212> TYPE: PRT
<213> ORGANISM: Artificial Sequence
<220> FEATURE:
<223> OTHER INFORMATION: Description of Artificial Sequence: Light chain
      mammalian humanized antibody

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 45
<211> LENGTH: 120
<212> TYPE: PRT
<213> ORGANISM: Artificial Sequence
<220> FEATURE:
<223> OTHER INFORMATION: Description of Artificial Sequence: Heavy chain
      mammalian humanized antibody

<400> SEQUENCE: 45

Glu Val Gln Leu Val Glu Ser Gly Gly Gly Leu Val Gln Pro Gly Gly
```

```
                1               5                  10                  15
Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser
        115                 120

<210> SEQ ID NO 46
<211> LENGTH: 107
<212> TYPE: PRT
<213> ORGANISM: Artificial Sequence
<220> FEATURE:
<223> OTHER INFORMATION: Description of Artificial Sequence: Light chain
      mammalian humanized antibody

<400> SEQUENCE: 46

Asp Ile Gln Met Thr Gln Ser Pro Ser Ser Leu Ser Ala Ser Val Gly
1               5                  10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys
            100                 105

<210> SEQ ID NO 47
<211> LENGTH: 120
<212> TYPE: PRT
<213> ORGANISM: Artificial Sequence
<220> FEATURE:
<223> OTHER INFORMATION: Description of Artificial Sequence:  Heavy chain
      mammalian humanized antibody

<400> SEQUENCE: 47

Glu Val Gln Leu Val Glu Ser Gly Gly Gly Leu Val Gln Pro Gly Gly
1               5                  10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
```

```
              65                  70                  75                  80
Leu Gln Met Asn Ser Leu Arg Ala Glu Asp Thr Ala Val Tyr Tyr Cys
                    85                  90                  95

Ser Arg Trp Gly Gly Asp Gly Phe Tyr Ala Met Asp Tyr Trp Gly Gln
                100                 105                 110

Gly Thr Leu Val Thr Val Ser Ser
        115                 120

<210> SEQ ID NO 48
<211> LENGTH: 108
<212> TYPE: PRT
<213> ORGANISM: Artificial Sequence
<220> FEATURE:
<223> OTHER INFORMATION: Description of Artificial Sequence: Light chain
      mammalian humanized antibody

<400> SEQUENCE: 48

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Ser Ala
                20                  25                  30

Val Ala Trp Tyr Gln Gln Lys Pro Gly Lys Ala Pro Lys Leu Leu Ile
            35                  40                  45

Asp Trp Ser Ala Ser Phe Leu Tyr Ser Gly Val Pro Ser Arg Phe Ser
        50                  55                  60

Gly Ser Arg Ser Gly Thr Asp Phe Thr Leu Thr Ile Ser Ser Leu Gln
65                  70                  75                  80

Pro Glu Asp Phe Ala Thr Tyr Tyr Cys Gln Gln His Tyr Thr Thr Pro
                85                  90                  95

Pro Thr Phe Gly Gln Gly Thr Lys Val Glu Ile Lys
            100                 105

<210> SEQ ID NO 49
<211> LENGTH: 121
<212> TYPE: PRT
<213> ORGANISM: Artificial Sequence
<220> FEATURE:
<223> OTHER INFORMATION: Description of Artificial Sequence: Heavy chain
      mammalian humanized antibody

<400> SEQUENCE: 49

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
                20                  25                  30

Tyr Ile His Trp Val Arg Gln Ala Pro Gly Lys Gly Leu Glu Trp Val
            35                  40                  45

Ala Arg Ile Tyr Pro Thr Asn Gly Tyr Thr Arg Tyr Ala Asp Ser Val
        50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Trp Gly Pro Lys Leu Ala Met Asp Tyr Trp Gly
                100                 105                 110

Gln Gly Thr Leu Val Thr Val Ser Ser
            115                 120
```

```
<210> SEQ ID NO 50
<211> LENGTH: 216
<212> TYPE: PRT
<213> ORGANISM: Artificial Sequence
<220> FEATURE:
<223> OTHER INFORMATION: Description of Artificial Sequence: Light chain
      mammalian humanized antibody

<400> SEQUENCE: 50

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Asn Phe Tyr Pro Arg Glu
    130                 135                 140

Ala Lys Val Gln Trp Lys Val Asp Asn Ala Leu Gln Ser Gly Glu Asn
145                 150                 155                 160

Ser Gln Glu Ser Val Thr Glu Gln Asp Ser Lys Asp Ser Thr Tyr Ser
                165                 170                 175

Leu Ser Ser Thr Leu Thr Leu Ser Lys Ala Asp Tyr Glu Lys His Lys
            180                 185                 190

Val Tyr Ala Cys Glu Val Thr His Gln Gly Leu Ser Ser Pro Val Thr
        195                 200                 205

Lys Ser Phe Asn Arg Gly Glu Cys
    210                 215

<210> SEQ ID NO 51
<211> LENGTH: 448
<212> TYPE: PRT
<213> ORGANISM: Artificial Sequence
<220> FEATURE:
<223> OTHER INFORMATION: Description of Artificial Sequence: Heavy chain
      mammalian humanized antibody

<400> SEQUENCE: 51

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
```

```
                    85                  90                  95

Ala Arg Asn Leu Gly Pro Ser Phe Tyr Phe Asp Tyr Trp Gly Gln Gly
                100                 105                 110

Thr Leu Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 52
<211> LENGTH: 217
<212> TYPE: PRT
<213> ORGANISM: Artificial Sequence
<220> FEATURE:
<223> OTHER INFORMATION: Description of Artificial Sequence: Light
      chain mammalian humanized antibody

<400> SEQUENCE: 52
```

Val His Ser Asp Ile Gln Met Thr Gln Ser Pro Ser Ser Leu Ser Ala
1               5                   10                  15

Ser Val Gly Asp Arg Val Thr Ile Thr Cys Lys Ala Ser Gln Asp Val
            20                  25                  30

Ser Ile Gly Val Ala Trp Tyr Gln Gln Lys Pro Gly Lys Ala Pro Lys
        35                  40                  45

Leu Leu Ile Tyr Ser Ala Ser Tyr Arg Tyr Thr Gly Val Pro Ser Arg
    50                  55                  60

Phe Ser Gly Ser Gly Ser Gly Thr Asp Phe Thr Leu Thr Ile Ser Ser
65              70                  75                  80

Leu Gln Pro Glu Asp Phe Ala Thr Tyr Tyr Cys Gln Gln Tyr Tyr Ile
            85                  90                  95

Tyr Pro Tyr Thr Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145             150                 155                 160

Asn Ser Gln Glu Ser Val Thr Glu Gln Asp Ser Lys Asp Ser Thr Tyr
            165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
        210                 215

<210> SEQ ID NO 53
<211> LENGTH: 448
<212> TYPE: PRT
<213> ORGANISM: Artificial Sequence
<220> FEATURE:
<223> OTHER INFORMATION: Description of Artificial Sequence: Heavy
      chain mammalian humanized antibody

<400> SEQUENCE: 53

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65              70                  75                  80

Leu Gln Met Asn Ser Leu Arg Ala Glu Asp Thr Ala Val Tyr Tyr Cys
            85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
            165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
            195                 200                 205

Ser Asn Thr Lys Val Asp Lys Lys Val Glu Pro Lys Ser Cys Asp Lys
        210                 215                 220

Thr His Thr Cys Pro Pro Cys Pro Ala Pro Glu Leu Leu Gly Gly Pro
225                 230                 235                 240

Ser Val Phe Leu Val Pro Pro Lys Pro Lys Asp Thr Leu Met Ile Ser
                245                 250                 255

Arg Thr Pro Glu Val Thr Cys Val Val Val Asp Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu Asn His Tyr Thr Gln Lys Ser Leu Ser Leu Ser Pro Gly Lys
            435                 440                 445

<210> SEQ ID NO 54
<211> LENGTH: 216
<212> TYPE: PRT
<213> ORGANISM: Artificial Sequence
<220> FEATURE:
<223> OTHER INFORMATION: Description of Artificial Sequence: Light
      chain mammalian humanized antibody

<400> SEQUENCE: 54

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly

```
                50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys Arg Thr Val Ala Ala
               100                 105                 110

Pro Ser Val Phe Ile Phe Pro Pro Ser Asp Glu Gln Leu Lys Ser Gly
               115                 120                 125

Thr Ala Ser Val Val Cys Leu Leu Asn Asn Asn Phe Tyr Pro Arg Glu
           130                 135                 140

Ala Lys Val Gln Trp Lys Val Asp Asn Ala Leu Gln Ser Gly Glu Asn
145                 150                 155                 160

Ser Gln Glu Ser Val Thr Glu Gln Asp Ser Lys Asp Ser Thr Tyr Ser
               165                 170                 175

Leu Ser Ser Thr Leu Thr Leu Ser Lys Ala Asp Tyr Glu Lys His Lys
           180                 185                 190

Val Tyr Ala Cys Glu Val Thr His Gln Gly Leu Ser Ser Pro Val Thr
           195                 200                 205

Lys Ser Phe Asn Arg Gly Glu Cys
       210                 215
```

<210> SEQ ID NO 55
<211> LENGTH: 448
<212> TYPE: PRT
<213> ORGANISM: Artificial Sequence
<220> FEATURE:
<223> OTHER INFORMATION: Description of Artificial Sequence: Heavy
      chain mammalian humanized antibody

<400> SEQUENCE: 55

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Thr Asp Tyr
             20                  25                  30

Thr Met Asp Trp Val Arg Gln Ala Pro Gly Lys Gly Leu Glu Trp Val
         35                  40                  45

Ala Asp Val Asn Pro Asn Ser Gly Gly Ser Ile Tyr Asn Gln Arg Phe
     50                  55                  60

Lys Gly Arg Phe Thr Leu Ser Val Asp Arg Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
               100                 105                 110

Thr Leu Val Thr Val Ser Ser Ala Ser Thr Lys Gly Pro Ser Val Phe
           115                 120                 125

Pro Leu Ala Pro Ser Ser Lys Ser Thr Ser Gly Gly Thr Ala Ala Leu
       130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
               165                 170                 175

Gln Ser Ser Gly Leu Tyr Ser Leu Ser Ser Val Val Thr Val Pro Ser
           180                 185                 190
```

```
Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 56
<211> LENGTH: 12
<212> TYPE: PRT
<213> ORGANISM: Artificial Sequence
<220> FEATURE:
<223> OTHER INFORMATION: Description of Artificial Sequence: Lytic
      peptide

<400> SEQUENCE: 56

Lys Leu Ala Lys Leu Ala Lys Lys Leu Ala Lys
1               5                   10

<210> SEQ ID NO 57
<211> LENGTH: 6
<212> TYPE: PRT
<213> ORGANISM: Artificial Sequence
<220> FEATURE:
<223> OTHER INFORMATION: Description of Artificial Sequence: Linker

<400> SEQUENCE: 57

Asn Arg Val Arg Arg Ser
1               5

<210> SEQ ID NO 58
<211> LENGTH: 2217
<212> TYPE: DNA
```

<213> ORGANISM: Artificial Sequence
<220> FEATURE:
<223> OTHER INFORMATION: Description of Artificial Sequence: Mammalian humanized antibody

<400> SEQUENCE: 58

```
catatgcatc accaccacca ccacgacgac gacgacaaag atattcaaat gacccagtcc      60
ccgagcagcc tgagtgcctc cgttggcgac cgcgtgacca ttacgtgccg tgcgagccag     120
gatgtcaaca ccgcggtggc ctggtatcag caaaaaccgg gcaaagcgcc gaaactgctg     180
atctattcag cctcgtttct gtacagcggt gttccgtctc gtttcagcgg ctctcgcagt     240
ggtaccgatt tacccctgac gattagctct ctgcagccgg aagactttgc gacgtattac     300
tgccagcaac attacaccac gccgccgacc ttcggccagg gtacgaaagt ggaaatcaaa     360
ggttccacct caggcggtgg cagtggtggc ggttccggcg gtggcggtag ttccgaagtt     420
cagctggtcg aaagtggcgg tggcctggtt caaccgggtg gctcactgcg tctgtcgtgt     480
gcagcaagcg gtttcaacat caaagatacc tacatccact gggttcgtca ggcgccgggc     540
aaaggtctgg aatgggtcgc ccgcatttac ccgaccaatg gctatacgcg ttacgcagat     600
agcgtgaaag gtcgctttac catctctgcg gacaccagta aaaacacggc ctatctgcag     660
atgaatagcc tgcgtgcgga agatacggcc gtttattact gctctcgctg gggtggcgat     720
ggcttctatg ctatggacta ctggggccag ggtaccctgg tgacggtttc atcgggtcag     780
ccgcgtgaac cgcaagtgta taccctgccg ccgtcacgcg atgaactgac gaaaaaccag     840
gtgtcgctga cgtgtctggt taaaggcttt tacccgagcg acatcgcggt tgaatgggaa     900
tctaatggtc aaccggaaaa caattataaa accacgccgc cggtcctgga tagtgacggc     960
tccttttttcc tgtacagtaa actgaccgtg gataaatccc gttggcagca gggtaacgtc    1020
ttctcgtgta gcgtgatgca tgaagccctg cataatcact atacccagaa atctctgagt    1080
ctgtccccgg gcaaaggttc aacgtcgggt ggcggttccg gcggtggctc aggtggcggt    1140
ggcagctctg gccaaccgcg cgaaccgcag gtttacaccc tgccgccgag ccgtgacgaa    1200
ctgaccaaaa accaagtcag cctgacgtgc ctggtgaaag ctttttaccc gagtgacatt    1260
gcagttgaat gggaatccaa tggtcagccg gaaaataact acaaaacgac gccgccggtt    1320
ctggattcag acggctcgtt tttcctgtac tcaaaactga ccgtcgataa atcgcgctgg    1380
caacagggta cgttttcag ctgctctgtc atgcacgaag ccctgcacaa ccattatacc    1440
cagaaaagtc tgtccctgtc accgggcaaa gaagtgcagc tggttgaatc tggtggcggt    1500
ctggtgcaac cggcggttc gctgcgtctg agctgtgcag cttctggctt taatattaaa    1560
gacacgtaca tccactgggt gcgtcaggca ccgggtaaag gcctggaatg ggttgctcgt    1620
atctatccga cgaacggtta tacgcgttac gccgatagcc tcaaaggccg ttttaccatc    1680
agtgcagaca cctccaaaaa cacggcttat ctgcagatga atagtctgcg tgcagaagat    1740
accgctgttt attactgcag ccgctggggc ggtgatggct ctatgcaat ggattattgg     1800
ggtcaaggta ccctggtcac cgtgagttcc ggttcgacca gcggcggtgg ctcaggtggc    1860
ggttcgggcg gtggcggttc atcggacatt cagatgacgc aaagcccgag ctctctgtct    1920
gcgagtgttg gcgatcgtgt caccatcacg tgtcgcgcct cgcaggacgt gaataccgca    1980
gttgcttggt accaacaaaa accgggcaaa gcaccgaaac tgctgattta ctccgcttca    2040
ttcctgtaca gcggtgtgcc gtctcgtttt tcgggcagcc gctctggtac cgatttcacc    2100
ctgacgatta gttccctgca accggaagat ttcgccacct actactgcca gcaacactat    2160
```
acgaccccgc cgacgtttgg tcagggcacg aaagtggaaa ttaaataatg aaagctt    2217

<210> SEQ ID NO 59
<211> LENGTH: 2277
<212> TYPE: DNA
<213> ORGANISM: Artificial Sequence
<220> FEATURE:
<223> OTHER INFORMATION: Description of Artificial Sequence: Mammalian humanized antibody

<400> SEQUENCE: 59

| | | | | | |
|---|---|---|---|---|---|
| catatgcatc | accaccacca | ccacgacgac | gacgacaaag | atattcaaat | gacccagtcc | 60 |
| ccgagcagcc | tgagtgcctc | cgttggcgac | cgcgtgacca | ttacgtgccg | tgcgagccag | 120 |
| gatgtcaaca | ccgcggtggc | ctggtatcag | caaaaaccgg | gcaaagcgcc | gaaactgctg | 180 |
| atctattcag | cctcgtttct | gtacagcggt | gttccgtctc | gtttcagcgg | ctctcgcagt | 240 |
| ggtaccgatt | ttaccctgac | gattagctct | ctgcagccgg | aagactttgc | gacgtattac | 300 |
| tgccagcaac | attacaccac | gccgccgacc | ttcggccagg | gtacgaaagt | ggaaatcaaa | 360 |
| ggttccacct | caggcggtgg | cagtggtggc | ggttccggcg | gtggcggtag | ttccgaagtt | 420 |
| cagctggtcg | aaagtggcgg | tggcctggtt | caaccgggtg | gctcactgcg | tctgtcgtgt | 480 |
| gcagcaagcg | gtttcaacat | caaagatacc | tacatccact | gggttcgtca | ggcgccgggc | 540 |
| aaaggtctgg | aatgggtcgc | cgcatttac | ccgaccaatg | gctatacgcg | ttacgcagat | 600 |
| agcgtgaaag | gtcgctttac | catctctgcg | gacaccagta | aaaacacggc | ctatctgcag | 660 |
| atgaatagcc | tgcgtgcgga | agatacggcc | gtttattact | gctctcgctg | gggtggcgat | 720 |
| ggcttctatg | ctatggacta | ctggggccag | ggtaccctgg | tgacggtttc | atcgggtcag | 780 |
| ccgcgtgaac | cgcaagtgta | taccctgccg | ccgtcacgcg | atgaactgac | gaaaaaccag | 840 |
| gtgtcgctga | cgtgtctggt | taaggctttt | tacccgagcg | acatcgcggt | tgaatgggaa | 900 |
| tctaatggtc | aaccggaaaa | caattataaa | accacgccgc | cggtcctgga | tagtgacggc | 960 |
| tccttttttcc | tgtacagtaa | actgaccgtg | gataaatccc | gttggcagca | gggtaacgtc | 1020 |
| ttctcgtgta | gcgtgatgca | tgaagccctg | cataatcact | atacccagaa | atctctgagt | 1080 |
| ctgtccccgg | gcaaaggttc | aacgtcgggt | ggcggttccg | gcggtggctc | aggtggcggt | 1140 |
| ggcagctctg | gccaaccgcg | cgaaccgcag | gtttacaccc | tgccgccgag | ccgtgacgaa | 1200 |
| ctgaccaaaa | accaagtcag | cctgacgtgc | ctggtgaaag | gctttttaccc | gagtgacatt | 1260 |
| gcagttgaat | gggaatccaa | tggtcagccg | gaaaataact | acaaaacgac | gccgccggtt | 1320 |
| ctggattcag | acggctcgtt | tttcctgtac | tcaaaactga | ccgtcgataa | atcgcgctgg | 1380 |
| caacagggta | acgttttcag | ctgctctgtc | atgcacgaag | ccctgcacaa | ccattatacc | 1440 |
| cagaaaagtc | tgtccctgtc | accgggcaaa | gaagtgcagc | tggttgaatc | tggtggcggt | 1500 |
| ctggtgcaac | cgggcggttc | gctgcgtctg | agctgtgcag | cttctggctt | taatattaaa | 1560 |
| gacacgtaca | tccactgggt | gcgtcaggca | ccgggtaaag | gcctgaaatg | ggttgctcgt | 1620 |
| atctatccga | cgaacggtta | tacgcgttac | gccgatagcg | tcaaaggccg | ttttaccatc | 1680 |
| agtgcagaca | cctccaaaaa | cacggcttat | ctgcagatga | atagtctgcg | tgcagaagat | 1740 |
| accgctgttt | attactgcag | ccgctggggc | ggtgatggct | ctatgcaat | ggattattgg | 1800 |
| ggtcaaggta | ccctggtcac | cgtgagttcc | ggttcgacca | gcggcggtgg | ctcaggtggc | 1860 |
| ggttcgggcg | gtggcggttc | atcggacatt | cagatgacgc | aaagcccgag | ctctctgtct | 1920 |
| gcgagtgttg | gcgatcgtgt | caccatcacg | tgtcgcgcct | ctcaggacgt | gaataccgca | 1980 |

| | |
|---|---|
| gttgcttggt accaacaaaa accgggcaaa gcaccgaaac tgctgattta ctccgcttca | 2040 |
| ttcctgtaca gcggtgtgcc gtctcgtttt cgggcagcc gctctggtac cgatttcacc | 2100 |
| ctgacgatta gttccctgca accggaagat ttcgccacct actactgcca gcaacactat | 2160 |
| acgaccccgc cgacgtttgg tcagggcacg aaagtggaaa ttaaaggcag caaatttgcg | 2220 |
| aaattcgcca aaaattcgc aaaattcgcg aaaaaattcg cgaaataatg aaagctt | 2277 |

<210> SEQ ID NO 60
<211> LENGTH: 2265
<212> TYPE: DNA
<213> ORGANISM: Artificial Sequence
<220> FEATURE:
<223> OTHER INFORMATION: Description of Artificial Sequence: Mammalian
      humanized antibody

<400> SEQUENCE: 60

| | |
|---|---|
| catatggaaa atctgtattt ccaaggtgat attcaaatga cccagtcccc gagcagcctg | 60 |
| agtgcctccg ttggcgaccg cgtgaccatt acgtgccgtg cgagccagga tgtcaacacc | 120 |
| gcggtggcct ggtatcagca aaaccgggc aaagcgccga actgctgat ctattcagcc | 180 |
| tcgtttctgt acagcggtgt tccgtctcgt ttcagcggct ctcgcagtgg taccgatttt | 240 |
| accctgacga ttagctctct gcagccggaa gactttgcga cgtattactg ccagcaacat | 300 |
| tacaccacgc cgccgacctt cggccagggt acgaaagtgg aaatcaaagg ttccacctca | 360 |
| ggcggtggca gtggtggcgg ttccggcggt ggcggtagtt ccgaagttca gctggtcgaa | 420 |
| agtggcggtg gcctggttca accgggtggc tcactgcgtc tgtcgtgtgc agcaagcggt | 480 |
| ttcaacatca agataccta catccactgg gttcgtcagg cgccgggcaa aggtctggaa | 540 |
| tgggtcgccc gcatttaccc gaccaatggc tatacgcgtt acgcagatag cgtgaaaggt | 600 |
| cgctttacca tctctgcgga caccagtaaa aacacggcct atctgcagat gaatagcctg | 660 |
| cgtgcggaag atacggccgt ttattactgc tctcgctggg gtggcgatgg cttctatgct | 720 |
| atggactact ggggccaggg taccctggtg acggtttcat cgggtcagcc gcgtgaaccg | 780 |
| caagtgtata ccctgccgcc gtcacgcgat gaactgacga aaaaccaggt gtcgctgacg | 840 |
| tgtctggtta aaggctttta cccgagcgac atcgcggttg aatgggaatc taatggtcaa | 900 |
| ccggaaaaca attataaaac cacgccgccg gtcctggata tgacggctc cttttttcctg | 960 |
| tacagtaaac tgaccgtgga taaatcccgt tggcagcagg gtaacgtctt ctcgtgtagc | 1020 |
| gtgatgcatg aagccctgca taatcactat acccagaaat ctctgagtct gtccccgggc | 1080 |
| aaaggttcaa cgtcgggtgg cggttccggc ggtggctcag gtggcggtgg cagctctggc | 1140 |
| caaccgcgcg aaccgcaggt ttacaccctg ccgccgagcc gtgacgaact gaccaaaaac | 1200 |
| caagtcagcc tgacgtgcct ggtgaaaggc ttttacccga gtgacattgc agttgaatgg | 1260 |
| gaatccaatg gtcagccgga aaataactac aaaacgacgc cgccggttct ggattcagac | 1320 |
| ggctcgtttt tcctgtactc aaaactgacc gtcgataaat cgcgctggca acagggtaac | 1380 |
| gttttcagct gctctgtcat gcacgaagcc ctgcacaacc attataccca gaaaagtctg | 1440 |
| tccctgtcac cgggcaaaga agtgcagctg gttgaatctg gtggcggtct ggtgcaaccg | 1500 |
| ggcggttcgc tgcgtctgag ctgtgcagct tctggcttta atattaaaga cacgtacatc | 1560 |
| cactgggtgc gtcaggcacc gggtaaaggc ctggaatggg ttgctcgtat ctatccgacg | 1620 |
| aacggttata cgcgttacgc cgatagcgtc aaaggccgtt ttaccatcag tgcagacacc | 1680 |
| tccaaaaaca cggcttatct gcagatgaat agtctgcgtg cagaagatac cgctgtttat | 1740 |

| | |
|---|---|
| tactgcagcc gctggggcgg tgatggcttc tatgcaatgg attattgggg tcaaggtacc | 1800 |
| ctggtcaccg tgagttccgg ttcgaccagc ggcggtggct caggtggcgg ttcgggcggt | 1860 |
| ggcggttcat cggacattca gatgacgcaa agcccgagct ctctgtctgc gagtgttggc | 1920 |
| gatcgtgtca ccatcacgtg tcgcgcctct caggacgtga ataccgcagt tgcttggtac | 1980 |
| caacaaaaac cgggcaaagc accgaaactg ctgatttact ccgcttcatt cctgtacagc | 2040 |
| ggtgtgccgt ctcgttttc gggcagccgc tctggtaccg atttcaccct gacgattagt | 2100 |
| tccctgcaac cggaagattt cgccacctac tactgccagc aacactatac gaccccgccg | 2160 |
| acgtttggtc agggcacgaa agtggaaatt aaaggcagca actggcgaa actggccaaa | 2220 |
| aaactggcaa aactggcgaa aaaactggcg aaataatgaa agctt | 2265 |

<210> SEQ ID NO 61
<211> LENGTH: 2277
<212> TYPE: DNA
<213> ORGANISM: Artificial Sequence
<220> FEATURE:
<223> OTHER INFORMATION: Description of Artificial Sequence: Mammalian humanized antibody

<400> SEQUENCE: 61

| | |
|---|---|
| catatggaaa atctgtattt ccaaggtgat attcaaatga cccagtcccc gagcagcctg | 60 |
| agtgcctccg ttggcgaccg cgtgaccatt acgtgccgtg cgagccagga tgtcaacacc | 120 |
| gcggtggcct ggtatcagca aaaccgggc aaagcgccga aactgctgat ctattcagcc | 180 |
| tcgtttctgt acagcggtgt tccgtctcgt ttcagcggct ctcgcagtgg taccgatttt | 240 |
| accctgacga ttagctctct gcagccggaa gactttgcga cgtattactg ccagcaacat | 300 |
| tacaccacgc cgccgacctt cggccagggt acgaaagtgg aaatcaaagg ttccacctca | 360 |
| ggcggtggca gtggtggcgg ttccggcggt ggcggtagtt ccgaagttca gctggtcgaa | 420 |
| agtggcggtg gcctggttca accgggtggc tcactgcgtc tgtcgtgtgc agcaagcggt | 480 |
| ttcaacatca agatacccta catccactgg gttcgtcagg cgccgggcaa aggtctggaa | 540 |
| tgggtcgccc gcatttaccc gaccaatggc tatacgcgtt acgcagatag cgtgaaaggt | 600 |
| cgctttacca tctctgcgga caccagtaaa aacacggcct atctgcagat gaatagcctg | 660 |
| cgtgcggaag atacggccgt ttattactgc tctcgctggg gtggcgatgg cttctatgct | 720 |
| atggactact ggggccaggg taccctggtg acggtttcat cgggtcagcc gcgtgaaccg | 780 |
| caagtgtata ccctgccgcc gtcacgcgat gaactgacga aaaccaggt gtcgctgacg | 840 |
| tgtctggtta aggctttta cccgagcgac atcgcggttg aatgggaatc taatggtcaa | 900 |
| ccggaaaaca attataaaac cacgccgccg gtcctggata tgacggctc ctttttcctg | 960 |
| tacagtaaac tgaccgtgga taatcccgt tggcagcagg gtaacgtctt ctcgtgtagc | 1020 |
| gtgatgcatg aagccctgca taatcactat acccagaaat ctctgagtct gtccccgggc | 1080 |
| aaaggttcaa cgtcgggtgg cggttccggc ggtggctcag gtggcggtgg cagctctggc | 1140 |
| caaccgcgcg aaccgcaggt ttacaccctg ccgccgagcc gtgacgaact gaccaaaaac | 1200 |
| caagtcagcc tgacgtgcct ggtgaaaggc ttttacccga gtgacattgc agttgaatgg | 1260 |
| gaatccaatg gtcagccgga aaataactac aaaacgacgc cgccggttct ggattcagac | 1320 |
| ggctcgtttt tcctgtactc aaaactgacc gtcgataaat cgcgctggca cagggtaac | 1380 |
| gttttcagct gctctgtcat gcacgaagcc ctgcacaacc attataccca gaaaagtctg | 1440 |
| tccctgtcac cgggcaaaga gtgcagctg gttgaatctg gtggcggtct ggtgcaaccg | 1500 |

```
ggcggttcgc tgcgtctgag ctgtgcagct tctggcttta atattaaaga cacgtacatc    1560
cactgggtgc gtcaggcacc gggtaaaggc ctggaatggg ttgctcgtat ctatccgacg    1620
aacggttata cgcgttacgc cgatagcgtc aaaggccgtt ttaccatcag tgcagacacc    1680
tccaaaaaca cggcttatct gcagatgaat agtctgcgtg cagaagatac cgctgtttat    1740
tactgcagcc gctggggcgg tgatggcttc tatgcaatgg attattgggg tcaaggtacc    1800
ctggtcaccg tgagttccgg ttcgaccagc ggcggtggct caggtggcgg ttcgggcggt    1860
ggcggttcat cggacattca gatgacgcaa agcccgagct ctctgtctgc gagtgttggc    1920
gatcgtgtca ccatcacgtg tcgcgcctct caggacgtga ataccgcagt tgcttggtac    1980
caacaaaaac cgggcaaagc accgaaactg ctgatttact ccgcttcatt cctgtacagc    2040
ggtgtgccgt ctcgtttttc gggcagccgc tctggtaccg atttcaccct gacgattagt    2100
tccctgcaac cggaagattt cgccacctac tactgccagc aacactatac gaccccgccg    2160
acgtttggtc agggcacgaa agtggaaatt aaaaaccgtg tgcgtcgcag caaatttgcg    2220
aaattcgcca aaaatttgc aaaattcgct aaaaatttg cgaataatg aaagctt    2277
```

<210> SEQ ID NO 62
<211> LENGTH: 2289
<212> TYPE: DNA
<213> ORGANISM: Artificial Sequence
<220> FEATURE:
<223> OTHER INFORMATION: Description of Artificial Sequence: Mammalian
      humanized antibody

<400> SEQUENCE: 62

```
catatgcatc accaccacca ccacgacgac gacgacaaag atattcaaat gacccagtcc      60
ccgagcagcc tgagtgcctc cgttggcgac cgcgtgacca ttacgtgccg tgcgagccag     120
gatgtcaaca ccgcggtggc ctggtatcag caaaaaccgg gcaaagcgcc gaaactgctg     180
atctattcag cctcgttcct gtacagcggt gttccgtctc gtttcagcgg ctctcgcagt     240
ggtaccgatt ttaccctgac gattagctct ctgcagccgg aagactttgc gacgtattac     300
tgccagcaac attacaccac gccgccgacc ttcggccagg gtacgaaagt ggaaatcaaa     360
ggttccacct caggcggtgg cagtggtggc ggttccggcg gtggcggtag ttccgaagtt     420
cagctggtcg aaagtggcgg tggcctggtt caaccgggtg gctcactgcg tctgtcgtgt     480
gcagcaagcg gtttcaacat caagatacc tacatccact gggttcgtca ggcgccgggc     540
aaaggtctgg aatgggtcgc ccgcatttac ccgaccaatg gctatacgcg ttacgcagat     600
agcgtgaaag tcgctttac catctctgcg gacaccagta aaaacacggc ctatctgcag     660
atgaatagcc tgcgtgcgga agatacggcc gtttattact gctctcgctg gggtggcgat     720
ggcttctatg ctatggacta ctggggccag ggtaccctgg tgacggtttc atcgggtcag     780
ccgcgtgaac cgcaagtgta taccctgccg ccgtcacgcg atgaactgac gaaaaaccag     840
gtgtcgctga cgtgtctggt taaaggcttt taccccgagcg acatcgcggt tgaatgggaa     900
tctaatggtc aaccggaaaa caattataaa accacgccgc cggtcctgga tagtgacggc     960 tccttttcc tgtacagtaa actgaccgtg gataaatccc gttggcagca gggtaacgtc    1020
ttctcgtgta gcgtgatgca tgaagccctg cataatcact ataccagaa atctctgagt    1080 ctgtccccgg gcaaaggttc aacgtcgggt ggcggttccg gcggtggctc aggtggcgt    1140 ggcagctctg gccaaccgcg cgaaccgcag gtttacaccc tgccgccgag ccgtgacgaa    1200
ctgaccaaaa accaagtcag cctgacgtgc ctggtgaaag cttttacccc gagtgacatt    1260
```

-continued

```
gcagttgaat gggaatccaa tggtcagccg gaaaataact acaaaacgac gccgccggtt    1320
ctggattcag acggctcgtt tttcctgtac tcaaaactga ccgtcgataa atcgcgctgg    1380
caacagggta acgttttcag ctgctctgtc atgcacgaag ccctgcacaa ccattatacc    1440
cagaaaagtc tgtccctgtc accgggcaaa gaagtgcagc tggttgaatc tggtggcggt    1500
ctggtgcaac cggcggttc gctgcgtctg agctgtgcag cttctggctt taatattaaa    1560
gacacgtaca tccactgggt gcgtcaggca ccgggtaaag gcctggaatg ggttgctcgt    1620
atctatccga cgaacggtta tacgcgttac gccgatagcg tcaaaggccg ttttaccatc    1680
agtgcagaca cctccaaaaa cacggcttat ctgcagatga atagtctgcg tgcagaagat    1740
accgctgttt attactgcag ccgctggggc ggtgatggct ctatgcaat ggattattgg    1800 ggtcaaggta ccctggtcac cgtgagttcc ggttcgacca cgggcggtgg ctcaggtggc    1860
ggttcgggcg gtggcggttc atcggacatt cagatgacgc aaagcccgag ctctctgtct    1920
gcgagtgttg gcgatcgtgt caccatcacg tgtcgcgcct ctcaggacgt gaataccgca    1980
gttgcttggt accaacaaaa accgggcaaa gcaccgaaac tgctgattta ctccgcttca    2040
ttcctgtaca gcggtgtgcc gtctcgtttt tcgggcagcc gctctggtac cgatttcacc    2100
ctgacgatta gttccctgca accggaagat ttcgccacct actactgcca gcaacactat    2160
acgaccccgc cgacgtttgg tcagggcacg aaagtggaaa ttaaaaaccg tgtgcgtcgc    2220
agcaaactgg cgaaactggc caaaaaactg gcaaaactgg ctaaaaaact ggcgaaataa    2280
tgaaagctt                                                            2289
```

<210> SEQ ID NO 63
<211> LENGTH: 2313
<212> TYPE: DNA
<213> ORGANISM: Artificial Sequence
<220> FEATURE:
<223> OTHER INFORMATION: Description of Artificial Sequence: Mammalian humanized antibody

<400> SEQUENCE: 63

```
catatggaaa atctgtattt ccaaggtaaa tttgcgaaat cgccaaaaaa attcgcaaaa      60
ttcgcgaaaa aattcgcgaa agatattcaa atgacccagt ccccgagcag cctgagtgcc     120
tccgttggcg accgcgtgac cattacgtgc cgtgcgagcc aggatgtcaa caccgcggtg     180
gcctggtatc agcaaaaacc gggcaaagcg ccgaaactgc tgatctattc agcctcgttt     240
ctgtacagcg gtgttccgtc tcgtttcagc ggctctcgca gtggtaccga ttttaccctg     300
acgattagct ctctgcagcc ggaagacttt gcgacgtatt actgccagca acattacacc     360
acgccgccga ccttcggcca gggtacgaaa gtggaaatca aggttccac tcaggcggt     420 ggcagtggtg gcggttccgg cggtggcggt agttccgaag ttcagctggt cgaaagtggc     480
ggtggcctgg ttcaaccggg tggctcactg cgtctgtcgt gtgcagcaag cggtttcaac     540
atcaaagata cctacatcca ctgggttcgt caggcgccgg gcaaaggtct ggaatgggtc     600
gcccgcattt acccgaccaa tggctatacg cgttacgcag atagcgtgaa aggtcgcttt     660
accatctctg cggacaccag taaaaacacg gcctatctgc agatgaatag cctgcgtgcg     720
gaagatacgg ccgtttatta ctgctctcgc tggggtggca tggcttcta tgctatggac     780 tactggggcc agggtaccct ggtgacggtt tcatcgggtc agccgcgtga accgcaagtg     840 tatacctgc cgccgtcacg cgatgaactg acgaaaaacc aggtgtcgct gacgtgtctg     900
gttaaaggct ttacccgag cgacatcgcg gttgaatggg aatctaatgg tcaaccggaa     960
```

```
aacaattata aaaccacgcc gccggtcctg gatagtgacg gctccttttt cctgtacagt   1020
aaactgaccg tggataaatc ccgttggcag cagggtaacg tcttctcgtg tagcgtgatg   1080
catgaagccc tgcataatca ctatacccag aaatctctga gtctgtcccc gggcaaaggt   1140
tcaacgtcgg gtggcggttc cggcggtggc tcaggtggcg gtggcagctc tggccaaccg   1200
cgcgaaccgc aggtttacac cctgccgccg agccgtgacg aactgaccaa aaaccaagtc   1260
agcctgacgt gcctggtgaa aggcttttac ccgagtgaca ttgcagttga atgggaatcc   1320
aatggtcagc cggaaaataa ctacaaaacg acgccgccgg ttctggattc agacggctcg   1380
tttttcctgt actcaaaact gaccgtcgat aaatcgcgct ggcaacaggg taacgttttc   1440
agctgctctg tcatgcacga agccctgcac aaccattata cccagaaaag tctgtccctg   1500
tcaccgggca agaagtgca gctggttgaa tctggtggcg gtctggtgca accgggcggt   1560
tcgctgcgtc tgagctgtgc agcttctggc tttaatatta agacacgta catccactgg   1620 gtgcgtcagg caccgggtaa aggcctgaa tggttgctc gtatctatcc gacgaacggt   1680
tatacgcgtt acgccgatag cgtcaaaggc cgttttacca tcagtgcaga cacctccaaa   1740
aacacggctt atctgcagat gaatagtctg cgtgcagaag ataccgctgt ttattactgc   1800
agccgctggg gcggtgatgg cttctatgca atggattatt ggggtcaagg taccctggtc   1860
accgtgagtt ccggttcgac cagcggcggt ggctcaggtg gcggttcggg cggtggcggt   1920
tcatcggaca ttcagatgac gcaaagcccg agctctctgt ctgcgagtgt tggcgatcgt   1980
gtcaccatca cgtgtcgcgc ctctcaggac gtgaataccg cagttgcttg gtaccaacaa   2040
aaaccgggca agcaccgaa actgctgatt tactccgctt cattcctgta cagcggtgtg   2100
ccgtctcgtt tttcgggcag ccgctctggt accgatttca ccctgacgat tagttccctg   2160
caaccggaag atttcgccac ctactactgc cagcaacact atacgacccc gccgacgttt   2220
ggtcagggca cgaaagtgga aattaaaaaa tttgcgaaat cgccaaaaaa attcgcaaaa   2280
ttcgcgaaaa aattcgcgaa ataatgaaag ctt                                2313
```

<210> SEQ ID NO 64
<211> LENGTH: 948
<212> TYPE: PRT
<213> ORGANISM: Artificial Sequence
<220> FEATURE:
<223> OTHER INFORMATION: Description of Artificial Sequence: Recombinant
      anti-Her2 antibody

<400> SEQUENCE: 64

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Ser Thr Ser Gly
            100                 105                 110

Gly Gly Ser Gly Gly Gly Ser Gly Gly Gly Gly Ser Ser Glu Val Gln
```

```
            115                 120                 125
Leu Val Glu Ser Gly Gly Leu Val Gln Pro Gly Gly Ser Leu Arg
130                 135                 140

Leu Ser Cys Ala Ala Ser Gly Phe Asn Ile Lys Asp Thr Tyr Ile His
145                 150                 155                 160

Trp Val Arg Gln Ala Pro Gly Lys Gly Leu Glu Trp Val Ala Arg Ile
                165                 170                 175

Tyr Pro Thr Asn Gly Tyr Thr Arg Tyr Ala Asp Ser Val Lys Gly Arg
                180                 185                 190

Phe Thr Ile Ser Ala Asp Thr Ser Lys Asn Thr Ala Tyr Leu Gln Met
            195                 200                 205

Asn Ser Leu Arg Ala Glu Asp Thr Ala Val Tyr Tyr Cys Ser Arg Trp
210                 215                 220

Gly Gly Asp Gly Phe Tyr Ala Met Asp Tyr Trp Gly Gln Gly Thr Leu
225                 230                 235                 240

Val Thr Val Ser Ser Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
                260                 265                 270

Arg Thr Pro Glu Val Thr Cys Val Val Val Asp Val Ser His Glu Asp
            275                 280                 285

Pro Glu Val Lys Phe Asn Trp Tyr Val Asp Gly Val Glu Val His Asn
290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
                340                 345                 350

Thr Ile Ser Lys Ala Lys Gly Gln Pro Arg Glu Pro Gln Val Tyr Thr
            355                 360                 365

Leu Pro Pro Ser Arg Asp Glu Leu Thr Lys Asn Gln Val Ser Leu Thr
370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
                420                 425                 430

Ser Arg Trp Gln Gln Gly Asn Val Phe Ser Cys Ser Val Met His Glu
            435                 440                 445

Ala Leu His Asn His Tyr Thr Gln Lys Ser Leu Ser Leu Ser Pro Gly
450                 455                 460

Lys Gly Ser Thr Ser Gly Gly Ser Gly Gly Gly Ser Gly Gly Gly
465                 470                 475                 480

Gly Ser Ser Gly Gln Pro Arg Glu Pro Gln Val Tyr Thr Leu Pro Pro
                485                 490                 495

Ser Arg Asp Glu Leu Thr Lys Asn Gln Val Ser Leu Thr Cys Leu Val
                500                 505                 510

Lys Gly Phe Tyr Pro Ser Asp Ile Ala Val Glu Trp Glu Ser Asn Gly
            515                 520                 525

Gln Pro Glu Asn Asn Tyr Lys Thr Thr Pro Pro Val Leu Asp Ser Asp
530                 535                 540
```

```
Gly Ser Phe Phe Leu Tyr Ser Lys Leu Thr Val Asp Lys Ser Arg Trp
545                 550                 555                 560

Gln Gln Gly Asn Val Phe Ser Cys Ser Val Met His Glu Ala Leu His
                565                 570                 575

Asn His Tyr Thr Gln Lys Ser Leu Ser Leu Ser Pro Gly Lys Pro Cys
            580                 585                 590

Pro Ala Pro Glu Leu Leu Gly Gly Pro Ser Val Phe Leu Phe Pro Pro
        595                 600                 605

Lys Pro Lys Asp Thr Leu Met Ile Ser Arg Thr Pro Glu Val Thr Cys
    610                 615                 620

Val Val Val Asp Val Ser His Glu Asp Pro Glu Val Lys Phe Asn Trp
625                 630                 635                 640

Tyr Val Asp Gly Val Glu Val His Asn Ala Lys Thr Lys Pro Arg Glu
                645                 650                 655

Glu Gln Tyr Asn Ser Thr Tyr Arg Val Val Ser Val Leu Thr Val Leu
            660                 665                 670

His Gln Asp Trp Leu Asn Gly Lys Glu Tyr Lys Cys Lys Val Ser Asn
        675                 680                 685

Lys Ala Leu Pro Ala Pro Ile Glu Lys Thr Ile Ser Lys Ala Lys Glu
    690                 695                 700

Val Gln Leu Val Glu Ser Gly Gly Leu Val Gln Pro Gly Gly Ser
705                 710                 715                 720

Leu Arg Leu Ser Cys Ala Ala Ser Gly Phe Asn Ile Lys Asp Thr Tyr
                725                 730                 735

Ile His Trp Val Arg Gln Ala Pro Gly Lys Gly Leu Glu Trp Val Ala
            740                 745                 750

Arg Ile Tyr Pro Thr Asn Gly Tyr Thr Arg Tyr Ala Asp Ser Val Lys
        755                 760                 765

Gly Arg Phe Thr Ile Ser Ala Asp Thr Ser Lys Asn Thr Ala Tyr Leu
    770                 775                 780

Gln Met Asn Ser Leu Arg Ala Glu Asp Thr Ala Val Tyr Tyr Cys Ser
785                 790                 795                 800

Arg Trp Gly Gly Asp Gly Phe Tyr Ala Met Asp Tyr Trp Gly Gln Gly
                805                 810                 815

Thr Leu Val Thr Val Ser Ser Gly Ser Thr Ser Gly Gly Gly Ser Gly
            820                 825                 830

Gly Gly Ser Gly Gly Gly Ser Asp Ile Gln Met Thr Gln Ser
        835                 840                 845

Pro Ser Ser Leu Ser Ala Ser Val Gly Asp Arg Val Thr Ile Thr Cys
    850                 855                 860

Arg Ala Ser Gln Asp Val Asn Thr Ala Val Ala Trp Tyr Gln Gln Lys
865                 870                 875                 880

Pro Gly Lys Ala Pro Lys Leu Leu Ile Tyr Ser Ala Ser Phe Leu Tyr
                885                 890                 895

Ser Gly Val Pro Ser Arg Phe Ser Gly Ser Arg Ser Gly Thr Asp Phe
            900                 905                 910

Thr Leu Thr Ile Ser Ser Leu Gln Pro Glu Asp Phe Ala Thr Tyr Tyr
        915                 920                 925

Cys Gln Gln His Tyr Thr Thr Pro Pro Thr Phe Gly Gln Gly Thr Lys
    930                 935                 940

Val Glu Ile Lys
945
```

<210> SEQ ID NO 65
<211> LENGTH: 968
<212> TYPE: PRT
<213> ORGANISM: Artificial Sequence
<220> FEATURE:
<223> OTHER INFORMATION: Description of Artificial Sequence: Lytic peptide conjugate

<400> SEQUENCE: 65

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Gly Ser Thr Ser Gly
            100                 105                 110

Gly Gly Ser Gly Gly Gly Ser Gly Gly Gly Ser Ser Glu Val Gln
        115                 120                 125

Leu Val Glu Ser Gly Gly Gly Leu Val Gln Pro Gly Gly Ser Leu Arg
    130                 135                 140

Leu Ser Cys Ala Ala Ser Gly Phe Asn Ile Lys Asp Thr Tyr Ile His
145                 150                 155                 160

Trp Val Arg Gln Ala Pro Gly Lys Gly Leu Glu Trp Val Ala Arg Ile
                165                 170                 175

Tyr Pro Thr Asn Gly Tyr Thr Arg Tyr Ala Asp Ser Val Lys Gly Arg
            180                 185                 190

Phe Thr Ile Ser Ala Asp Thr Ser Lys Asn Thr Ala Tyr Leu Gln Met
        195                 200                 205

Asn Ser Leu Arg Ala Glu Asp Thr Ala Val Tyr Tyr Cys Ser Arg Trp
    210                 215                 220

Gly Gly Asp Gly Phe Tyr Ala Met Asp Tyr Trp Gly Gln Gly Thr Leu
225                 230                 235                 240

Val Thr Val Ser Ser Pro Cys Pro Ala Pro Glu Leu Leu Gly Gly Pro
                245                 250                 255

Ser Val Phe Leu Phe Pro Pro Lys Pro Lys Asp Thr Leu Met Ile Ser
            260                 265                 270

Arg Thr Pro Glu Val Thr Cys Val Val Val Asp Val Ser His Glu Asp
        275                 280                 285

Pro Glu Val Lys Phe Asn Trp Tyr Val Asp Gly Val Glu Val His Asn
    290                 295                 300

Ala Lys Thr Lys Pro Arg Glu Glu Gln Tyr Asn Ser Thr Tyr Arg Val
305                 310                 315                 320

Val Ser Val Leu Thr Val Leu His Gln Asp Trp Leu Asn Gly Lys Glu
                325                 330                 335

Tyr Lys Cys Lys Val Ser Asn Lys Ala Leu Pro Ala Pro Ile Glu Lys
            340                 345                 350

Thr Ile Ser Lys Ala Lys Gly Gln Pro Arg Glu Pro Gln Val Tyr Thr
        355                 360                 365
```

```
Leu Pro Pro Ser Arg Asp Glu Leu Thr Lys Asn Gln Val Ser Leu Thr
    370                 375                 380

Cys Leu Val Lys Gly Phe Tyr Pro Ser Asp Ile Ala Val Glu Trp Glu
385                 390                 395                 400

Ser Asn Gly Gln Pro Glu Asn Asn Tyr Lys Thr Thr Pro Pro Val Leu
                405                 410                 415

Asp Ser Asp Gly Ser Phe Phe Leu Tyr Ser Lys Leu Thr Val Asp Lys
            420                 425                 430

Ser Arg Trp Gln Gln Gly Asn Val Phe Ser Cys Ser Val Met His Glu
        435                 440                 445

Ala Leu His Asn His Tyr Thr Gln Lys Ser Leu Ser Leu Ser Pro Gly
    450                 455                 460

Lys Gly Ser Thr Ser Gly Gly Gly Ser Gly Gly Gly Ser Gly Gly Gly
465                 470                 475                 480

Gly Ser Ser Gly Gln Pro Arg Glu Pro Gln Val Tyr Thr Leu Pro Pro
                485                 490                 495

Ser Arg Asp Glu Leu Thr Lys Asn Gln Val Ser Leu Thr Cys Leu Val
            500                 505                 510

Lys Gly Phe Tyr Pro Ser Asp Ile Ala Val Glu Trp Glu Ser Asn Gly
        515                 520                 525

Gln Pro Glu Asn Asn Tyr Lys Thr Thr Pro Pro Val Leu Asp Ser Asp
    530                 535                 540

Gly Ser Phe Phe Leu Tyr Ser Lys Leu Thr Val Asp Lys Ser Arg Trp
545                 550                 555                 560

Gln Gln Gly Asn Val Phe Ser Cys Ser Val Met His Glu Ala Leu His
                565                 570                 575

Asn His Tyr Thr Gln Lys Ser Leu Ser Leu Ser Pro Gly Lys Pro Cys
            580                 585                 590

Pro Ala Pro Glu Leu Leu Gly Gly Pro Ser Val Phe Leu Phe Pro Pro
        595                 600                 605

Lys Pro Lys Asp Thr Leu Met Ile Ser Arg Thr Pro Glu Val Thr Cys
    610                 615                 620

Val Val Val Asp Val Ser His Glu Asp Pro Glu Val Lys Phe Asn Trp
625                 630                 635                 640

Tyr Val Asp Gly Val Glu Val His Asn Ala Lys Thr Lys Pro Arg Glu
                645                 650                 655

Glu Gln Tyr Asn Ser Thr Tyr Arg Val Val Ser Val Leu Thr Val Leu
            660                 665                 670

His Gln Asp Trp Leu Asn Gly Lys Glu Tyr Lys Cys Lys Val Ser Asn
        675                 680                 685

Lys Ala Leu Pro Ala Pro Ile Glu Lys Thr Ile Ser Lys Ala Lys Glu
    690                 695                 700

Val Gln Leu Val Glu Ser Gly Gly Gly Leu Val Gln Pro Gly Gly Ser
705                 710                 715                 720

Leu Arg Leu Ser Cys Ala Ala Ser Gly Phe Asn Ile Lys Asp Thr Tyr
                725                 730                 735

Ile His Trp Val Arg Gln Ala Pro Gly Lys Gly Leu Glu Trp Val Ala
            740                 745                 750

Arg Ile Tyr Pro Thr Asn Gly Tyr Thr Arg Tyr Ala Asp Ser Val Lys
        755                 760                 765

Gly Arg Phe Thr Ile Ser Ala Asp Thr Ser Lys Asn Thr Ala Tyr Leu
    770                 775                 780
```

```
Gln Met Asn Ser Leu Arg Ala Glu Asp Thr Ala Val Tyr Tyr Cys Ser
785                 790                 795                 800

Arg Trp Gly Gly Asp Gly Phe Tyr Ala Met Asp Tyr Trp Gly Gln Gly
            805                 810                 815

Thr Leu Val Thr Val Ser Ser Gly Ser Thr Gly Gly Gly Ser Gly
            820                 825                 830

Gly Gly Ser Gly Gly Gly Ser Asp Ile Gln Met Thr Gln Ser
            835                 840                 845

Pro Ser Ser Leu Ser Ala Ser Val Gly Asp Arg Val Thr Ile Thr Cys
    850                 855                 860

Arg Ala Ser Gln Asp Val Asn Thr Ala Val Ala Trp Tyr Gln Gln Lys
865                 870                 875                 880

Pro Gly Lys Ala Pro Lys Leu Leu Ile Tyr Ser Ala Ser Phe Leu Tyr
            885                 890                 895

Ser Gly Val Pro Ser Arg Phe Ser Gly Ser Arg Ser Gly Thr Asp Phe
            900                 905                 910

Thr Leu Thr Ile Ser Ser Leu Gln Pro Glu Asp Phe Ala Thr Tyr Tyr
            915                 920                 925

Cys Gln Gln His Tyr Thr Thr Pro Pro Thr Phe Gly Gln Gly Thr Lys
    930                 935                 940

Val Glu Ile Lys Gly Ser Lys Phe Ala Lys Phe Ala Lys Phe Ala
945                 950                 955                 960

Lys Phe Ala Lys Lys Phe Ala Lys
                965

<210> SEQ ID NO 66
<211> LENGTH: 20
<212> TYPE: PRT
<213> ORGANISM: Artificial Sequence
<220> FEATURE:
<223> OTHER INFORMATION: Description of Artificial Sequence: Lytic
      peptide conjugate

<400> SEQUENCE: 66

Gly Ser Lys Leu Ala Lys Leu Ala Lys Lys Leu Ala Lys Leu Ala Lys
1               5                   10                  15

Lys Leu Ala Lys
            20

<210> SEQ ID NO 67
<211> LENGTH: 18
<212> TYPE: PRT
<213> ORGANISM: Artificial Sequence
<220> FEATURE:
<223> OTHER INFORMATION: Description of Artificial Sequence: Lytic
      peptide conjugate

<400> SEQUENCE: 67

Lys Phe Ala Lys Phe Ala Lys Lys Phe Ala Lys Phe Ala Lys Lys Phe
1               5                   10                  15

Ala Lys

<210> SEQ ID NO 68
<211> LENGTH: 18
<212> TYPE: PRT
<213> ORGANISM: Artificial Sequence
<220> FEATURE:
<223> OTHER INFORMATION: Description of Artificial Sequence: Lytic
      peptide conjugate

<400> SEQUENCE: 68
```

```
Lys Leu Ala Lys Leu Ala Lys Lys Leu Ala Lys Leu Ala Lys Lys Leu
1               5                   10                  15

Ala Lys

<210> SEQ ID NO 69
<211> LENGTH: 24
<212> TYPE: PRT
<213> ORGANISM: Artificial Sequence
<220> FEATURE:
<223> OTHER INFORMATION: Description of Artificial Sequence: Lytic
      peptide conjugate

<400> SEQUENCE: 69

Asn Arg Val Arg Arg Ser Lys Leu Ala Lys Leu Ala Lys Lys Leu Ala
1               5                   10                  15

Lys Leu Ala Lys Lys Leu Ala Lys
            20
```